US010052203B2

(12) United States Patent
Spenser et al.

(10) Patent No.: US 10,052,203 B2
(45) Date of Patent: Aug. 21, 2018

(54) PROSTHETIC HEART VALVE AND METHOD

(71) Applicant: Edwards Lifesciences PVT, Inc., Irvine, CA (US)

(72) Inventors: Benjamin Spenser, D.N. Hof HaCarmel (IL); Netanel Benichou, D.N. Hof HaCarmel (IL); Assaf Bash, Benyamina-Givat Ada (IL); Avraham Zakai, Zichron-Yakov (IL)

(73) Assignee: Edwards Lifesciences PVT, Inc., Irvine, CA (US)

( * ) Notice: Subject to any disclaimer, the term of this patent is extended or adjusted under 35 U.S.C. 154(b) by 0 days.

(21) Appl. No.: 15/467,622

(22) Filed: Mar. 23, 2017

(65) Prior Publication Data

US 2017/0189183 A1 Jul. 6, 2017

Related U.S. Application Data

(60) Continuation of application No. 14/918,297, filed on Oct. 20, 2015, now Pat. No. 9,629,717, which is a (Continued)

(51) Int. Cl.
*A61F 2/24* (2006.01)
*A61F 2/82* (2013.01)
*A61F 2/95* (2013.01)

(52) U.S. Cl.
CPC .......... *A61F 2/2418* (2013.01); *A61F 2/2409* (2013.01); *A61F 2/2412* (2013.01);
(Continued)

(58) Field of Classification Search
CPC ........ A61F 2/24; A61F 2/2409; A61F 2/2412; A61F 2/2418; A61F 2/2427; A61F 2/243; A61F 2/2433; A61F 2/2436
See application file for complete search history.

(56) References Cited

U.S. PATENT DOCUMENTS 1,264,472 A 4/1918 Artzt
2,832,078 A 4/1958 Williams
(Continued)

FOREIGN PATENT DOCUMENTS

DE 2246526 A1 3/1973
DE 19532846 A1 3/1997
(Continued)

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.
(Continued)

*Primary Examiner* — Howie Matthews
(74) *Attorney, Agent, or Firm* — Klarquist Sparkman LLP

(57) ABSTRACT

A prosthetic heart valve comprises a radially crimpable and radially expandable, net-like, annular support frame and a valve assembly disposed therein, the valve assembly comprising a conduit tapering from an inlet towards an outlet thereof. Some embodiments or the support frame comprise a proximal portion and a distal portion, a diameter of the proximal portion smaller than a diameter of the distal portion. The proximal portion is dimensioned for deployment in an annulus of a native aortic valve and a distal portion for deployment in an ascending aorta. Some embodiments of the conduit comprise a support construction with a three-cusp, crown-shaped cut line, the support construction sutured to the support frame around a bottom portion thereof and around the cut line. A method for using the prosthetic heart valve to replace a defective native aortic valve uses a minimally invasive procedure.

15 Claims, 53 Drawing Sheets

Related U.S. Application Data continuation of application No. 14/716,714, filed on May 19, 2015, now Pat. No. 9,168,133, which is a continuation of application No. 14/159,327, filed on Jan. 20, 2014, now Pat. No. 9,132,006, which is a continuation of application No. 13/529,909, filed on Jun. 21, 2012, now Pat. No. 8,632,586, which is a continuation of application No. 13/168,016, filed on Jun. 24, 2011, now abandoned, which is a continuation of application No. 11/692,889, filed on Mar. 28, 2007, now abandoned, which is a continuation of application No. 10/637,882, filed on Aug. 8, 2003, now Pat. No. 7,510,575, which is a division of application No. 10/270,252, filed on Oct. 11, 2002, now Pat. No. 6,730,118, which is a continuation-in-part of application No. 09/975,750, filed on Oct. 11, 2001, now Pat. No. 6,893,460.

(52) U.S. Cl.
CPC .......... *A61F 2/2433* (2013.01); *A61F 2/2436* (2013.01); *A61F 2/2463* (2013.01); *A61F 2/2403* (2013.01); *A61F 2/2415* (2013.01); *A61F 2/2427* (2013.01); *A61F 2/82* (2013.01); *A61F 2002/9522* (2013.01); *A61F 2220/0008* (2013.01); *A61F 2220/0016* (2013.01); *A61F 2220/0075* (2013.01); *A61F 2220/0083* (2013.01); *A61F 2230/0054* (2013.01); *A61F 2230/0069* (2013.01); *A61F 2250/001* (2013.01); *A61F 2250/0098* (2013.01)

(56) References Cited

U.S. PATENT DOCUMENTS

| | | | |
|---|---|---|---|
| 3,409,013 A | 11/1968 | Berry |
| 3,472,230 A | 10/1969 | Fogarty |
| 3,548,417 A | 12/1970 | Kisher |
| 3,570,014 A | 3/1971 | Hancock |
| 3,587,115 A | 6/1971 | Shiley |
| 3,608,097 A | 9/1971 | Bellhouse |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,857,744 A | 12/1974 | Moss |
| 3,983,581 A | 10/1976 | Angell et al. |
| 4,035,849 A | 7/1977 | Angell et al. |
| 4,056,854 A | 11/1977 | Boretos et al. |
| 4,084,268 A | 4/1978 | Ionescu et al. |
| 4,106,129 A | 8/1978 | Carpentier et al. |
| 4,172,295 A | 10/1979 | Batten |
| 4,192,020 A | 3/1980 | Davis et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,491,986 A | 1/1985 | Gabbay |
| 4,501,030 A | 2/1985 | Lane |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,725,274 A | 2/1988 | Lane et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,141,494 A | 8/1992 | Danforth et al. |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,197,978 A | 3/1993 | Hess |
| 5,232,446 A | 8/1993 | Arney |
| 5,266,073 A | 11/1993 | Wall |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Troll |
| 5,411,552 A | 5/1995 | Andersen et al. |
| 5,443,446 A | 8/1995 | Shturman |
| 5,480,424 A | 1/1996 | Cox |
| 5,489,298 A | 2/1996 | Love et al. |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,195 A | 1/1997 | Taheri et al. |
| 5,599,305 A | 2/1997 | Hermann et al. |
| 5,607,464 A | 3/1997 | Trescony et al. |
| 5,609,626 A | 3/1997 | Quijano et al. |
| 5,636,641 A | 6/1997 | Fariabi |
| 5,639,274 A | 6/1997 | Fischell et al. |
| 5,665,115 A | 9/1997 | Cragg |
| 5,679,905 A | 10/1997 | Wardle |
| 5,681,345 A | 10/1997 | Euteneuer |
| 5,707,376 A | 1/1998 | Kavteladze et al. |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,853,419 A | 12/1998 | Imran |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 5,968,068 A | 10/1999 | Dehdashtian et al. |
| 5,980,570 A | 11/1999 | Simpson |
| 5,984,959 A | 11/1999 | Robertson et al. |

(56) References Cited

U.S. PATENT DOCUMENTS

| | | |
|---|---|---|
| 6,027,525 A | 2/2000 | Suh et al. |
| 6,132,473 A | 10/2000 | Williams et al. |
| 6,159,227 A | 12/2000 | Di Caprio et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,254,636 B1 | 7/2001 | Peredo |
| 6,299,637 B1 | 10/2001 | Shaolian et al. |
| 6,302,906 B1 | 10/2001 | Goecoechea et al. |
| 6,309,417 B1 | 10/2001 | Spence et al. |
| 6,350,277 B1 | 2/2002 | Kocur |
| 6,371,983 B1 | 4/2002 | Lane |
| 6,379,372 B1 | 4/2002 | Dehdashtian et al. |
| 6,419,695 B1 | 7/2002 | Gabbay |
| 6,425,916 B1 | 7/2002 | Garrison et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Marred |
| 6,488,704 B1 | 12/2002 | Connelly et al. |
| 6,494,909 B2 | 12/2002 | Greenhalgh |
| 6,527,979 B2 | 3/2003 | Constantz |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,767,362 B2 | 7/2004 | Schreck |
| 6,830,584 B1 | 12/2004 | Seguin |
| 6,869,444 B2 | 3/2005 | Gabbay |
| 6,893,460 B2 | 5/2005 | Spenser et al. |
| 6,896,690 B1 | 5/2005 | Lambrecht et al. |
| 6,908,481 B2 | 6/2005 | Cribier |
| 6,964,682 B2 | 11/2005 | Nguyen-Thien-Nhon et al. |
| 7,018,406 B2 | 3/2006 | Seguin et al. |
| 7,160,322 B2 | 1/2007 | Gabbay |
| 7,276,078 B2 | 10/2007 | Spenser et al. |
| 7,276,084 B2 | 10/2007 | Yang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 9,629,717 B2 | 4/2017 | Spenser et al. |
| 2001/0021872 A1 | 9/2001 | Bailey et al. |
| 2002/0032481 A1 | 3/2002 | Gabbay |
| 2002/0052651 A1 | 5/2002 | Myers et al. |
| 2002/0173842 A1 | 11/2002 | Buchanan |
| 2002/0198594 A1 | 12/2002 | Schreck |
| 2003/0014105 A1 | 1/2003 | Cao |
| 2003/0027332 A1 | 2/2003 | Lafrance et al. |
| 2003/0050694 A1 | 3/2003 | Yang et al. |
| 2003/0130729 A1 | 7/2003 | Paniagua et al. |
| 2003/0158597 A1 | 8/2003 | Quiachon et al. |
| 2004/0039436 A1 | 2/2004 | Spenser et al. |
| 2004/0133263 A1 | 7/2004 | Dusbabek et al. |
| 2004/0186565 A1 | 9/2004 | Schreck |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0143246 A2 | 6/1985 |
| EP | 0144167 A2 | 6/1985 |
| EP | 0150608 A1 | 8/1985 |
| EP | 0155245 A2 | 9/1985 |
| EP | 0196116 A2 | 10/1986 |
| EP | 0515324 A1 | 11/1992 |
| EP | 0541215 A1 | 5/1993 |
| EP | 0350302 B1 | 6/1993 |
| EP | 0592410 A1 | 4/1994 |
| EP | 0597967 A1 | 5/1994 |
| EP | 0850607 A1 | 7/1998 |
| EP | 0856300 A1 | 8/1998 |
| EP | 0788802 A3 | 4/2000 |
| EP | 1057460 A1 | 12/2000 |
| EP | 1088529 A2 | 4/2001 |
| EP | 1264582 A2 | 12/2002 |
| EP | 1267753 B1 | 10/2005 |
| EP | 1328215 B1 | 11/2005 |
| EP | 1406561 A4 | 3/2008 |
| EP | 1353612 B1 | 11/2009 |
| EP | 2055266 A3 | 3/2010 |
| FR | 2788217 A1 | 7/2000 |
| FR | 2815844 A1 | 5/2002 |
| GB | 2056023 A | 3/1981 |
| NL | 1017275 C2 | 8/2002 |
| SU | 1271508 A1 | 11/1986 |
| WO | 8300617 A1 | 3/1983 |
| WO | 8900840 A1 | 2/1989 |
| WO | 90/11738 A1 | 10/1990 |
| WO | 91/17720 A1 | 11/1991 |
| WO | 92/09247 A1 | 6/1992 |
| WO | 9212690 A1 | 8/1992 |
| WO | 9213502 A1 | 8/1992 |
| WO | 92/17118 A1 | 10/1992 |
| WO | 9219184 A1 | 11/1992 |
| WO | 93001768 A1 | 2/1993 |
| WO | 94/01060 A1 | 1/1994 |
| WO | 94/04099 A1 | 3/1994 |
| WO | 95/16412 A1 | 6/1995 |
| WO | 9602212 A1 | 2/1996 |
| WO | 9640008 A1 | 12/1996 |
| WO | 97/24080 A1 | 7/1997 |
| WO | 97/24082 A1 | 7/1997 |
| WO | 98/29057 A1 | 7/1998 |
| WO | 98/32400 A1 | 7/1998 |
| WO | 98/43557 A1 | 10/1998 |
| WO | 98043556 A1 | 10/1998 |
| WO | 9916387 A1 | 4/1999 |
| WO | 9930646 A1 | 6/1999 |
| WO | 99/33414 A1 | 7/1999 |
| WO | 99/40964 A1 | 8/1999 |
| WO | 99/47075 A1 | 9/1999 |
| WO | 9949817 A1 | 10/1999 |
| WO | 99/66863 A2 | 12/1999 |
| WO | 0000107 A1 | 1/2000 |
| WO | 00/18333 A1 | 4/2000 |
| WO | 00/21469 A1 | 4/2000 |
| WO | 00/41652 A1 | 7/2000 |
| WO | 200042950 A2 | 7/2000 |
| WO | 00/44313 A1 | 8/2000 |
| WO | 00/47139 A1 | 8/2000 |
| WO | 00/53125 A1 | 9/2000 |
| WO | 00/62714 A1 | 10/2000 |
| WO | 00/62716 A1 | 10/2000 |
| WO | 01/05334 A1 | 1/2001 |
| WO | 0064381 A3 | 2/2001 |
| WO | 0119285 A1 | 3/2001 |
| WO | 0128459 A1 | 4/2001 |
| WO | 01/35870 A1 | 5/2001 |
| WO | 01/41679 A1 | 6/2001 |
| WO | 0141652 A1 | 6/2001 |
| WO | 01/49213 A2 | 7/2001 |
| WO | 0152775 A1 | 7/2001 |
| WO | 01/62189 A1 | 8/2001 |
| WO | 0154624 A1 | 8/2001 |
| WO | 0154625 A1 | 8/2001 |
| WO | 0156512 A1 | 8/2001 |

(56) References Cited

FOREIGN PATENT DOCUMENTS

| | | |
|---|---|---|
| WO | 01/64137 A1 | 9/2001 |
| WO | 01/64138 A2 | 9/2001 |
| WO | 01/76510 A2 | 10/2001 |
| WO | 0182840 A1 | 11/2001 |
| WO | 02/22054 A1 | 3/2002 |
| WO | 0224118 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 02076348 A1 | 10/2002 |
| WO | 03007795 A2 | 1/2003 |
| WO | 2003003949 A2 | 1/2003 |
| WO | 0249545 A3 | 3/2003 |
| WO | 03/047468 A1 | 6/2003 |

OTHER PUBLICATIONS

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Al Zaibag, Muayed, et al., "Percutaneous Balloon Valvotomy in Tricuspid Stenosis," British Heart Journal, Jan. 1987, vol. 57, No. 1, pp. 51-53.

Andersen, et al., "Transluminal implantation of artificial heart valves. Description of a new expandable aortic valve and initial results with implantation by catheter technique in closed chest pigs." European Heart Journal (1992), 13, 704-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dake, Transluminal Placement of Endovascular Stent-Grafts for the Treatment of Descending Thoracic Aortic Aneurysms, New Engl. J.Med., 1994; 331:1729-34.

Dotter, M.D., Charles T., "Transluminal Treatment of Arteriosclerotic Obstruction," University of Oregon's Minthom Memorial Laboratory for Cardiovascular Research through Radiology, Circulation, vol. XXX, Nov. 1964, pp. 654-670.

Kolata, Gina, "Device That Opens Clogged Arteries Gets a Failing Grade in a New Study," nytimes.com, <http://www.nytimes.com/1991/01/03/health/device-that-opens-clogged-arteries-gets-a-faili>. . . , Jul. 29, 2009, 2 pages.

Inoue, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., M.D., David D., "Percutaneous Endovascular Graft: Experimental Evaluation," Radiology 1897; 163: 357-360.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W., et al., "Der Verschluß des Ductus Arteriosus Persistens ohne Thorakotomie," Thoraxchirurgie Vaskuläre Chirurgie, Band 15, Heft 2, Stuttgart, im Apr. 1967, pp. 199-203.

Rashkind, M.D., William J., "Creation of an Atrial Septal Defect Withoput Thoracotomy," the Journal of the American Medical Association, vol. 196, No. 11, Jun. 13, 1966, pp. 173-174.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida, Barry T., et al., "Modifications of Gianturco Expandable Wire Stents," AJR:150, May 1988, Dec. 3, 1987, pp. 1185-1187.

Urban, M.D., Philip, "Coronary Artery Stenting," Editions Mèdecine et Hygiène, Genève, 1991, pp. 5-47.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Wheatley, M.D., David J., "Valve Prostheses," Rob & Smith's Operative Surgery, Fourth Edition, pp. 415-424, Butterworths 1986.

Extended European Search Report for EP16000181, dated Jun. 8, 2016.

Transcript in French with English translation of television report by Jerome Cheval broadcasted over "France 2" on Apr. 18, 2002, including selected screen shots, 6 pages.

Printout of webpage http://www.ina.fr/video/2001226001041/pose-valve-sans-chirurgie-video.htm- I from the ina.fr website containing video titled "Pose valve sans chirurgie" (also available at http://www.youtube.com/watch?v=eUnxgy-rajc) correspondingto television report by Jerome Cheval which was broadcasted on Apr. 18, 2002 in "20 heures le journal", 1 page.

Transcript in French with English translation of television report by Jean Christophe Batteria broadcasted over "France 3 Rouen" on Apr. 18, 2002, including selected screen shots, 6 pages.

Printout of webpage http://www.ina.fr/video/RO00001304876) from the ina.fr website containing the video titled "CHU Rouen: premiere cardiologie mondiale" corresponding to television report by Jean Christophe Batteria which was broadcasted on Apr. 18, 2002 in "JT Haute Normandie soir", 1 page.

INA—Historique de l'Institut national de l'audiovisuel depuis sa cretion, http://www.instit-national-audiovisuel.fr/nous-connaitre/entreprise/histo- ire.html, printed May 23, 2014, 4 pages.

Cribier A., "Development of transcatheter aortic valve implantation (TAVI): A 20-year odyssey," Archives of Cardiovascular Disease 105, pp. 146-152 (Mar. 2012).

"First Heart Valve Replacement without Open Heart Surgery" from website www.pytechnologies.com, Apr. 23, 2002, 1 page.

Cribier A., et al., "First human transcatheter implantation of an aortic valve prosthesis in a case of severe calcific aortic stenosis," Annales de Cardiologie et d'Angeiologie 52, pp. 173-175 (2003).

Cribier A., et al., "Percutaneous Transcatheter Implantation of an Aortic Valve Prosthesis for Calcific Aortic Stenosis: First Human Case Description," Circulation, 106, pp. 3005-3008 (Nov. 2002).

Summons of the Opposition Division in the matter against European Patent EP 1 441 672 B1 dated Jul. 17, 2014, 11 pages.

Letter of the Opposition Division in the matter against European Patent EP 1 441 672 B1 to the French Patent Office INPI dated Jul. 27, 2015, 27 pages.

Powerpoint Presentation "Percutaneous Transcatheter Implantation of an Aortic Valve Prosthesis for Calcific Aortic Stenosis: First Human Case," by Alain Cribier et al. held at the TCT 2002 symposium on Sep. 27, 2002 in Washington, DC, 28 pages.

Final Program of the TCT (Transcatheter Cardiovascular Therapeutics) 2002 symposium held on Sep. 24 to 28, 2002 in The Washington Convention Center, Washington, DC, 5 pages.

(56) References Cited

OTHER PUBLICATIONS

EPO Communication dated Jun. 25, 2010 with respect to the application underlying European Patent EP 1 441 672 B1 (application No. 02 804 403.0), 4 pages.

Butany, Jagdish, and Richard Leask. "The failure modes of biological prosthetic heart valves." Journal of long-term effects of medical implants 11, No. 3&4 (2001).

Butterfield, M., and J. Fisher. "Fatigue analysis of clinical bioprosthetic heart valves manufactured using photooxidized bovine pericardium." The Journal of heart valve disease 9, No. 1 (Jan. 2000): 161-6.

Fisher, J., D. J. Wheatley, G. R. Jack, L. Cathcart, and T. J. Spyt. "An improved pericardial bioprosthetic heart valve." European Journal of Cardio-Thoracic Surgery 1, No. 2 (Sep. 1987): 71-79.

Fisher, John. "Design development and evaluation of an improved pericardial bioprosthetic heart valve." PhD diss., University of Glasgow, 1986.

Garcia-Bengochea, Jose B., I. Casagrande, J. R. Gonzalez-Juanatey, L. Puig, J. Rubio, D. Duran, and J. Sierra. "The new Labcor-Santiago pericardial bioprosthesis." J Card Surg 6, No. 4 Suppl (Dec. 1991): 613-9.

Haziza, Frank, Gerard Papouin, Brian Barratt-Boyes, Grant Christie, and Ralph Whitlock. "Tears in bioprosthetic heart valve leaflets without calcific degeneration." J Heart Valve Dis 5, No. 1 (Jan. 1996): 35-39.

Salles, Claudio A., Enio Buffalo, Jose Carlos Andrade, J. Honorio Palma, Roney RP Silva, Ricardo Santiago, Ivan S. Casagrande, and Maria Consolacao V. Moreira. "Mitral valve replacement with glutaraldehyde preserved aortic allografts." European journal of cardio-thoracic surgery 13, No. 2 (Feb. 1998): 135-143.

Plaintiff's Boston Scientific Corporation's and Boston Scientific SciMed Inc.'s Initial Invalidity Contentions, *Boston Scientific Corp. and Boston Scientific SciMed, Inc.*, v. *Edwards Lifesciences Corporation*, Case No. 16-275-SLR-SRF, Nov. 9, 2016.

Thubrikar, Mano J. The aortic valve. CRC press, 1989.

Webb, John G., Bradley Munt, Raj R. Makkar, Tasneem Z. Naqvi, and Ninh Dang. "Percutaneous stent-mounted valve for treatment of aortic or pulmonary valve disease." Catheterization and cardiovascular interventions 63, No. 1 (Sep. 2004): 89-93.

European Search Report issued for EP17176926, dated Nov. 29, 2017.

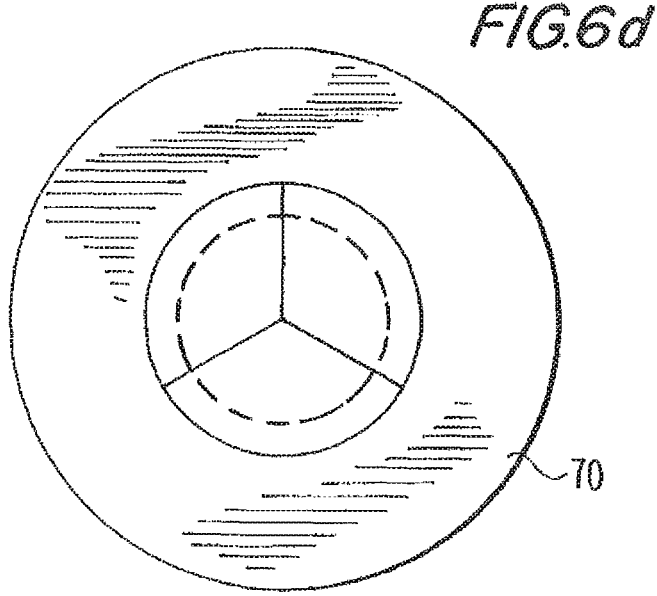
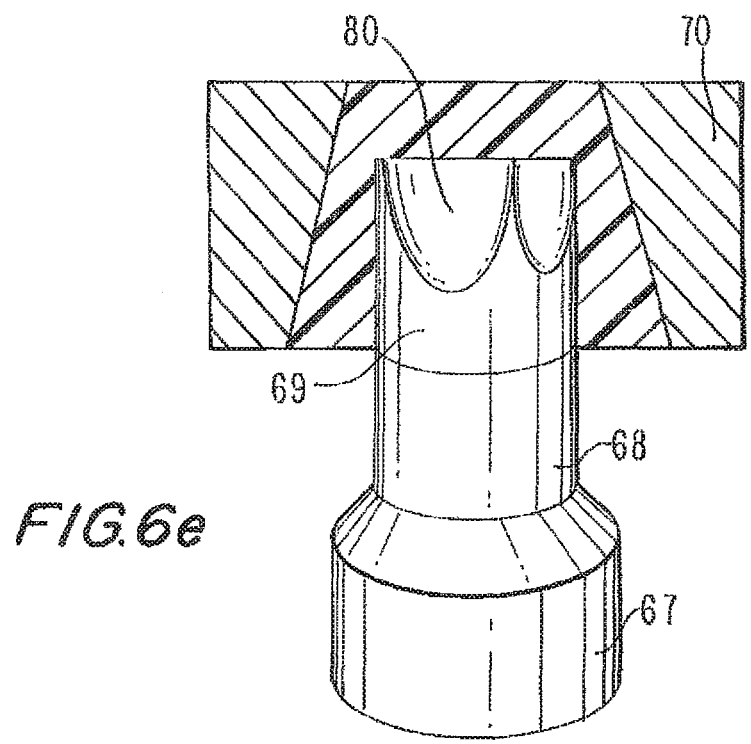

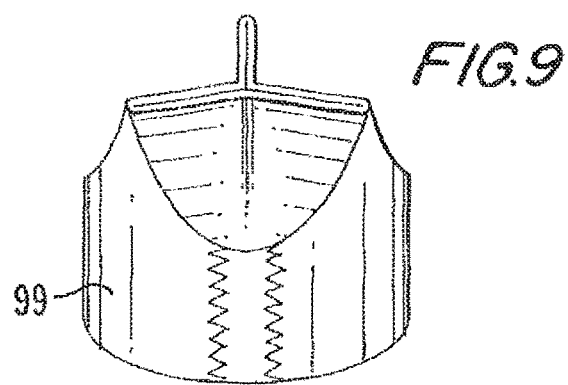
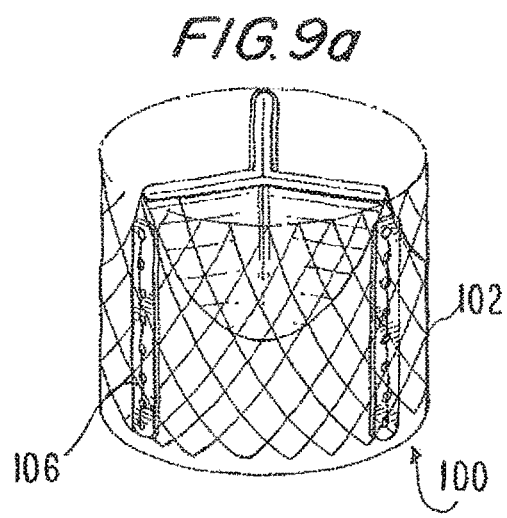
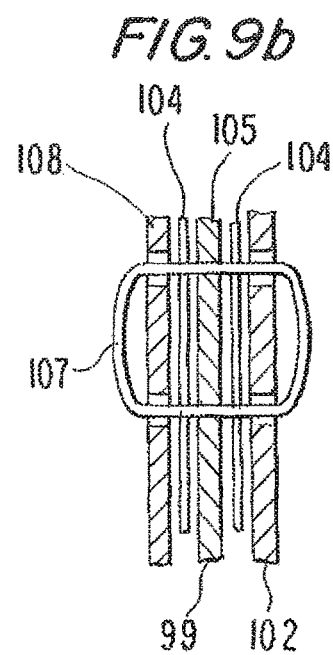
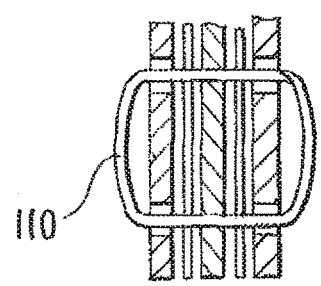
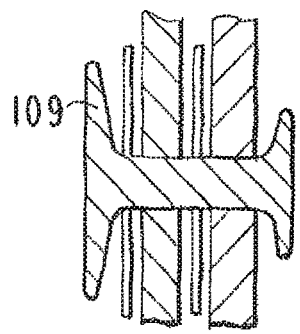

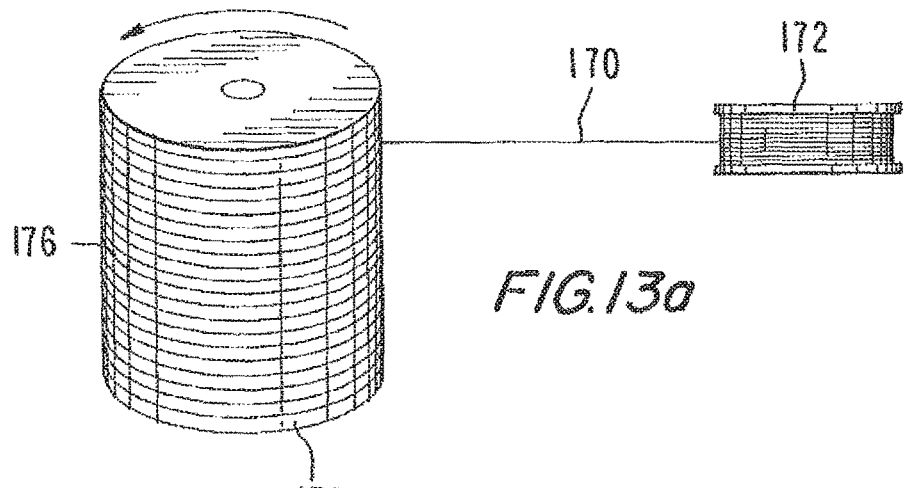
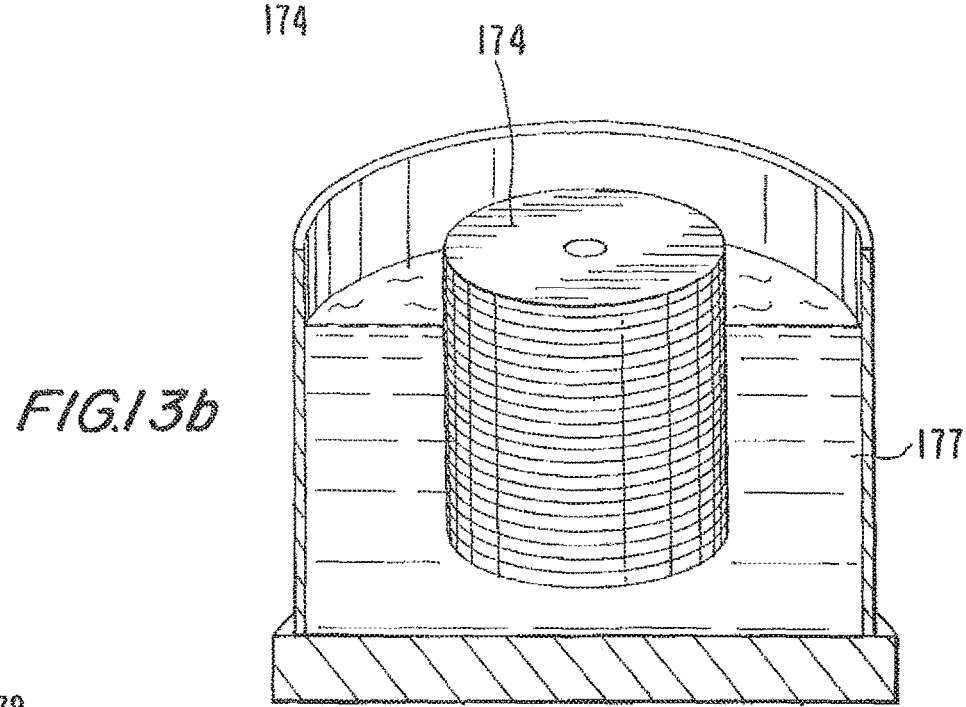
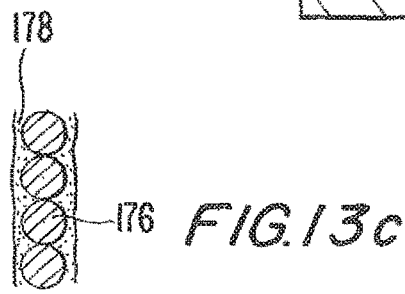

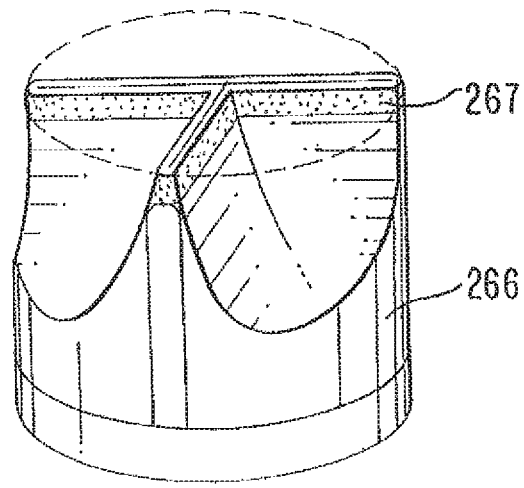
FIG. 15a
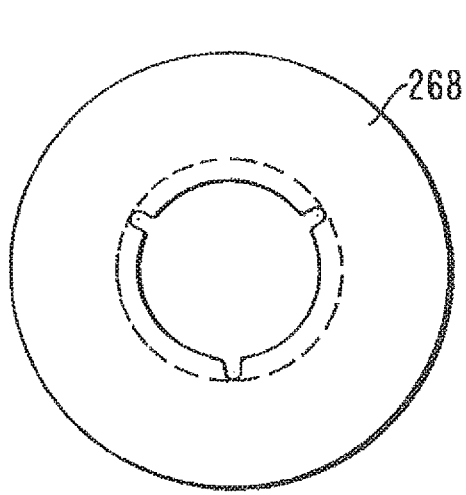 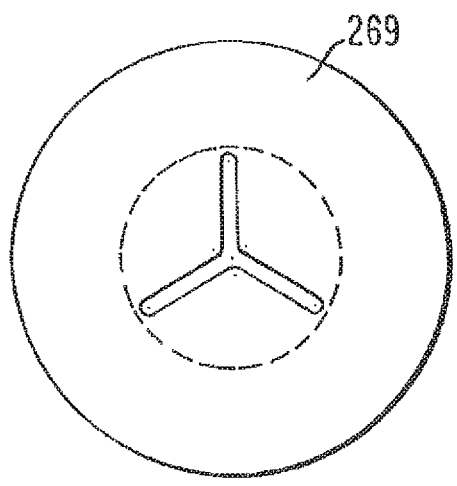
FIG. 15b    FIG. 15c

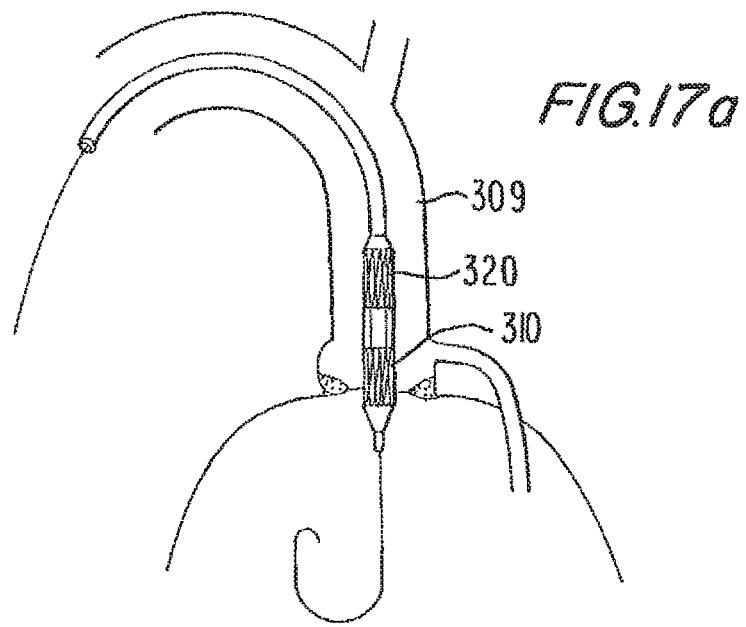
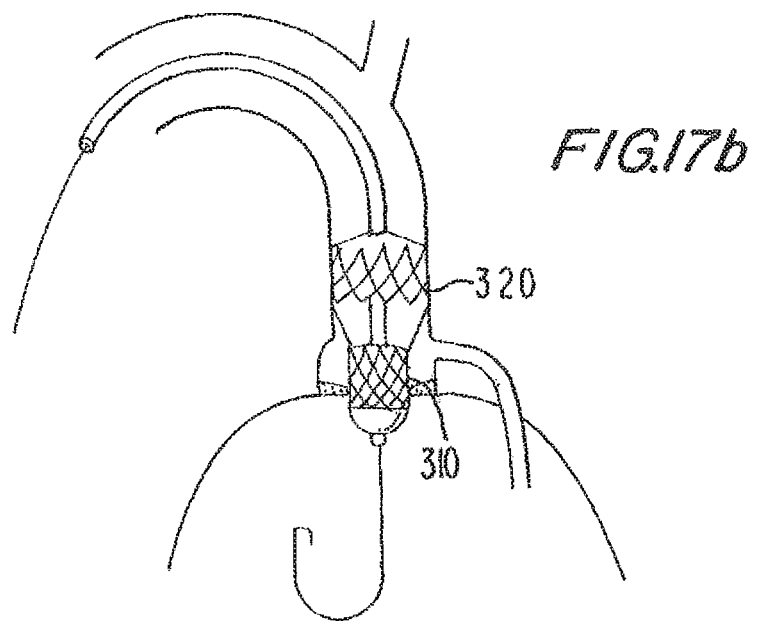

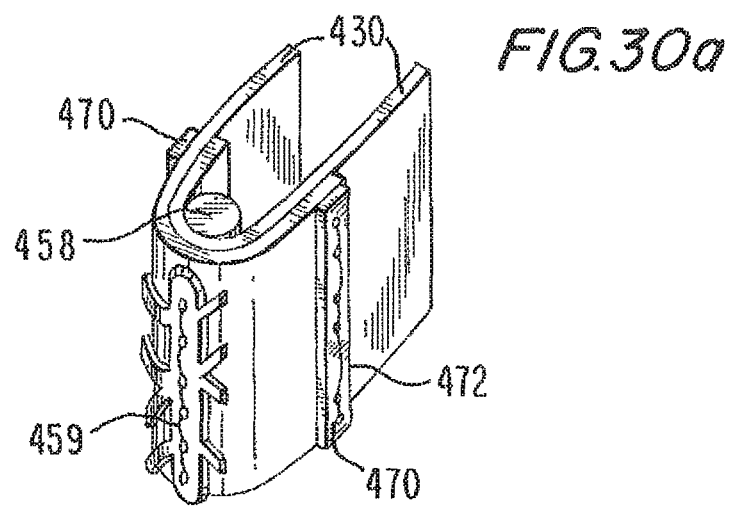
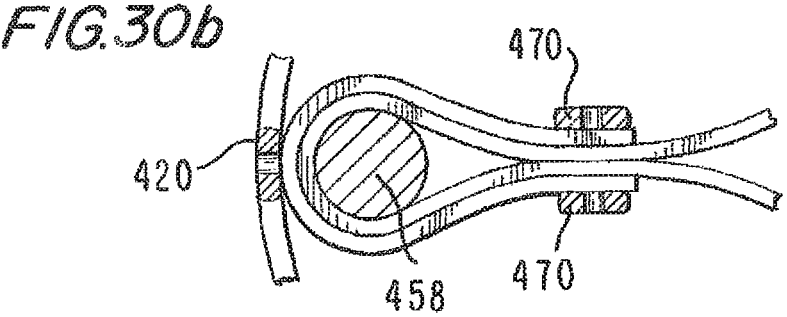
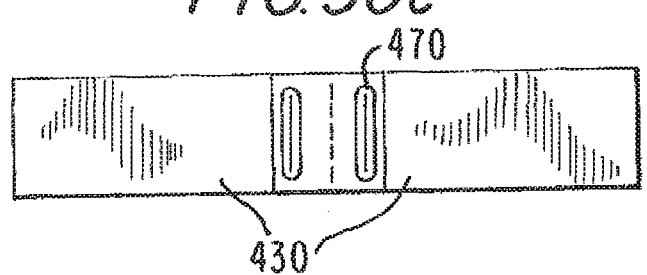

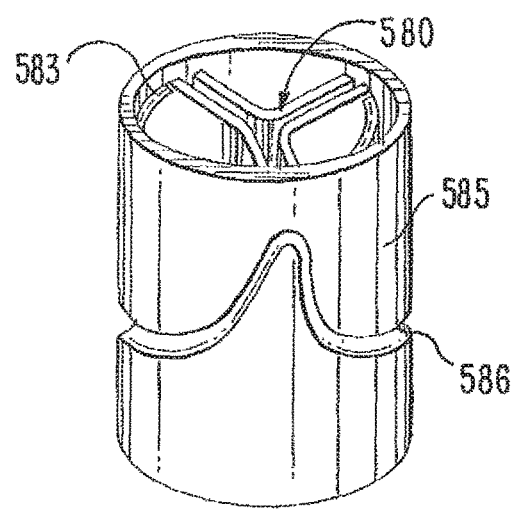
FIG.45a
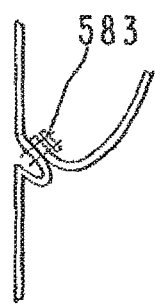 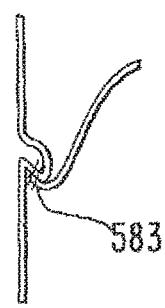 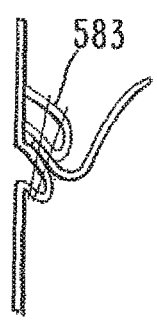
FIG.45b     FIG.45d     FIG.45c

PROSTHETIC HEART VALVE AND METHOD

CROSS-REFERENCE TO RELATED APPLICATIONS

This application is a continuation of U.S. patent application Ser. No. 14/918,297, filed Oct. 20, 2015, which is a continuation of U.S. patent application Ser. No. 14/716,714, filed May 19, 2015, now U.S. Pat. No. 9,168,133, which is a continuation of U.S. patent application Ser. No. 14/159,327, filed Jan. 20, 2014, now U.S. Pat. No. 9,132,006, which is a continuation of U.S. patent application Ser. No. 13/529,909, filed Jun. 21, 2012, now U.S. Pat. No. 8,632,586, which is a continuation of U.S. patent application Ser. No. 13/168,016, filed Jun. 24, 2011, which is a continuation of U.S. patent application Ser. No. 11/692,889, filed Mar. 28, 2007, which is a continuation of U.S. patent application Ser. No. 10/637,882, filed Aug. 8, 2003, now U.S. Pat. No. 7,510,575, which is a divisional of U.S. patent application Ser. No. 10/270,252, filed Oct. 11, 2002, now U.S. Pat. No. 6,730,118, which is a continuation-in-part of U.S. patent application Ser. No. 09/975,750, filed Oct. 11, 2001, now U.S. Pat. No. 6,893,460, the disclosures all of which are incorporated by reference in their entireties.

FIELD OF THE INVENTION

The present invention relates to implantable devices. More particularly, it relates to a valve prosthesis for cardiac implantation or for implantation in other body ducts.

BACKGROUND OF THE INVENTION

There are several known prosthetic valves that have been previously described. U.S. Pat. No. 5,411,552 (Andersen et al.), entitled VALVE PROSTHESIS FOR IMPLANTATION IN THE BODY AND CATHETER FOR IMPLANTING SUCH VALVE PROSTHESIS, discloses a valve prosthesis comprising a stent made from an expandable cylinder-shaped thread structure comprising several spaced apices. The elastically collapsible valve is mounted on the stent with the commissural points of the valve secured to the projecting apices, which prevents the valve from turning inside out. Deployment of the valve can be achieved by using an inflatable balloon which in its deflated state is used to carry about it the valve structure to its position and, when inflated, deploys the stent in position to its final size. See, also, U.S. Pat. No. 6,168,614 (Andersen et al.) entitled VALVE PROSTHESIS FOR IMPLANTATION IN THE BODY and U.S. Pat. No. 5,840,081 (Andersen et al.), entitled SYSTEM AND METHOD FOR IMPLANTING CARDIAC VALVES.

In PCT/EP97/07337 (Letac, Cribier et al.), published as WO 98/29057, entitled VALVE PROSTHESIS FOR IMPLANTATION IN BODY CHANNELS, there is disclosed a valve prosthesis comprising a collapsible valve structure and an expandable frame on which the valve structure is mounted. The valve structure is composed of a valvular tissue compatible with the human body and blood, the valvular tissue being sufficiently supple and resistant to allow the valve structure to be deformed from a closed state to an opened state. The valvular tissue forms a continuous surface and is provided with guiding means formed or incorporated within, the guiding means creating stiffened zones which induce the valve structure to follow a patterned movement in its expansion to its opened state and in its turning back to its closed state. The valve structure can be extended to an internal cover which is fastened to the lower part of the valve structure to prevent regurgitation.

There are several known methods currently used for replacing aortic valves and several types of artificial prosthetic devices. Mechanical valves are commonly used in several different designs (single and double flap) manufactured by well-known companies such as St. Jude, Medtronic, Sulzer, and others. Some of the main disadvantages of these devices are: a need for permanent treatment of anticoagulants, noisy operation, and a need for a large-scale operation to implant.

There is a wide range of biologically based valves made of natural valves or composed of biological materials such as pericardial tissue. These too are made and marketed by well-known companies such as Edwards Lifesciences, Medtronic, Sulzer, Sorin, and others.

Polymer valves are new and are not yet in use, but several companies are in the process of developing such products. A new type of prosthesis is being considered, based on artificial polymer materials such as polyurethane.

The present invention introduces several novel structural designs for implantable valves. An aspect of the present invention deals with the possibility of implanting the valve percutaneously, i.e., inserting the valve assembly on a delivery device similar to a catheter, then implanting the valve at the desired location via a large blood vessel such as the femoral artery, in a procedure similar to other known interventional cardiovascular procedures. The percutaneous deployment procedure and device has an impact on the product design in several parameters, some of which are explained hereinafter.

The percutaneous implantation of medical devices and particularly prosthetic valves is a preferred surgical procedure for it involves making a very small perforation in the patient's skin (usually in the groin or armpit area) under local anesthetic and sedation, as opposed to a large chest surgery incision, which requires general anesthesia, opening a large portion of the chest, and cardiopulmonary bypass. This percutaneous procedure is therefore considered safer.

The present invention provides a series of new concepts in the field of aortic valves and other human valves.

SUMMARY OF THE INVENTION

It is therefore thus provided, in accordance with a preferred embodiment of the present invention, a valve prosthesis device suitable for implantation in body ducts, the device comprising:

a support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, the support stent provided with a plurality of longitudinally rigid support beams of fixed length; and a valve assembly comprising a flexible conduit having an inlet end and an outlet, made of pliant material attached to the support beams providing collapsible slack portions of the conduit at the outlet, whereby when flow is allowed to pass through the valve prosthesis device from the inlet to the outlet the valve assembly is kept in an open position, whereas a reverse flow is prevented as the collapsible slack portions of the valve assembly collapse inwardly providing blockage to the reverse flow.

Furthermore, in accordance with another preferred embodiment of the present invention, the support stent comprises an annular frame.

Furthermore, in accordance with another preferred embodiment of the present invention, said valve assembly has a tricuspid configuration.

Furthermore, in accordance with another preferred embodiment of the present invention, said valve assembly is made from biocompatible material.

Furthermore, in accordance with another preferred embodiment of the present invention, the valve assembly is made from pericardial tissue, or other biological tissue.

Furthermore, in accordance with another preferred embodiment of the present invention, said valve assembly is made from biocompatible polymers.

Furthermore, in accordance with another preferred embodiment of the present invention, the valve assembly is made from materials selected from the group consisting of polyurethane and polyethylene terephthalate (PET).

Furthermore, in accordance with another preferred embodiment of the present invention, said valve assembly comprises a main body made from PET (polyethylene terephthalate) and leaflets made from polyurethane.

Furthermore, in accordance with another preferred embodiment of the present invention, said support stent is made from nickel titanium.

Furthermore, in accordance with another preferred embodiment of the present invention, the support beams are substantially equidistant and substantially parallel so as to provide anchorage for the valve assembly.

Furthermore, in accordance with another preferred embodiment of the present invention, the support beams are provided with bores so as to allow stitching or tying of the valve assembly to the beams.

Furthermore, in accordance with another preferred embodiment of the present invention, the support beams are chemically adhered to the support stent.

Furthermore, in accordance with another preferred embodiment of the present invention, said valve assembly is riveted to the support beams.

Furthermore, in accordance with another preferred embodiment of the present invention, said valve assembly is stitched to the support beams.

Furthermore, in accordance with another preferred embodiment of the present invention, said beams are manufactured by injection using a mold, or by machining.

Furthermore, in accordance with another preferred embodiment of the present invention, said valve assembly is rolled over the support stent at the inlet.

Furthermore, in accordance with another preferred embodiment of the present invention, said valve device is manufactured using forging or dipping techniques.

Furthermore, in accordance with another preferred embodiment of the present invention, said valve assembly leaflets are longer than needed to exactly close the outlet, thus when they are in the collapsed state substantial portions of the leaflets fall on each other creating better sealing.

Furthermore, in accordance with another preferred embodiment of the present invention, said valve assembly is made from coils of a polymer, coated by a coating layer of same polymer.

Furthermore, in accordance with another preferred embodiment of the present invention, said polymer is polyurethane.

Furthermore, in accordance with another preferred embodiment of the present invention, the support stent is provided with heavy metal markers so as to enable tracking and determining the valve device position and orientation.

Furthermore, in accordance with another preferred embodiment of the present invention, the heavy metal markers are selected from gold, platinum, iridium, or tantalum.

Furthermore, in accordance with another preferred embodiment of the present invention, the valve assembly leaflets are provided with radio-opaque material at the outlet, so as to help tracking the valve device operation in vivo.

Furthermore, in accordance with another preferred embodiment of the present invention, said radio-opaque material comprises gold thread.

Furthermore, in accordance with another preferred embodiment of the present invention, the diameter of said support stent, when fully deployed is in the range of from about 19 to about 25 mm.

Furthermore, in accordance with another preferred embodiment of the present invention, the diameter of said support stent may be expanded from about 4 to about 25 mm.

Furthermore, in accordance with another preferred embodiment of the present invention, the support beams are provided with bores and wherein the valve assembly is attached to the support beams by means of U-shaped rigid members that are fastened to the valve assembly and that are provided with extruding portions that fit into matching bores on the support beams.

Furthermore, in accordance with another preferred embodiment of the present invention, the support beams comprise rigid support beams in the form of frame construction, and the valve assembly pliant material is inserted through a gap in the frame and a fastening rod is inserted through a pocket formed between the pliant material and the frame and holds the valve in position.

Furthermore, in accordance with another preferred embodiment of the present invention, the main body of the valve assembly is made from coiled wire coated with coating material.

Furthermore, in accordance with another preferred embodiment of the present invention, the coiled wire and the coating material is made from polyurethane.

Furthermore, in accordance with another preferred embodiment of the present invention, a strengthening wire is interlaced in the valve assembly at the outlet of the conduit so as to define a fault line about which the collapsible slack portion of the valve assembly may flap.

Furthermore, in accordance with another preferred embodiment of the present invention, the strengthening wire is made from nickel titanium alloy.

Furthermore, in accordance with another preferred embodiment of the present invention, there is provided a valve prosthesis device suitable for implantation in body ducts, the device comprising a main conduit body having an inlet and an outlet and pliant leaflets attached at the outlet so that when a flow passes through the conduit from the inlet to the outlet the leaflets are in an open position allowing the flow to exit the outlet, and when the flow is reversed the leaflets collapse so as to block the outlet, wherein the main body is made from PET and collapsible leaflets are made form polyurethane.

Furthermore, in accordance with another preferred embodiment of the present invention, support beams made from polyurethane are provided on the main body and wherein the leaflets are attached to the main body at the support beams.

Furthermore, in accordance with another preferred embodiment of the present invention, said support beams are chemically adhered to the main body.

Furthermore, in accordance with another preferred embodiment of the present invention, there is provided a valve prosthesis device suitable for implantation in body ducts, the device comprising:

a support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, the support stent provided with a plurality of longitudinally rigid support beams of fixed length;

a valve assembly comprising a flexible conduit having an inlet end and an outlet, made of pliant material attached to the support beams providing collapsible slack portions of the conduit at the outlet; and substantially equidistant rigid support beams interlaced or attached to the slack portion of the valve assembly material, arranged longitudinally.

Furthermore, in accordance with another preferred embodiment of the present invention, there is provided a crimping device for crimping the valve device described above or in Claim 1, the crimping device comprising a plurality of adjustable plates that resemble a typical SLR (Single Lens Reflex) camera variable restrictor, each provided with a blade, that are equally dispersed in a radial symmetry but each plate moves along a line passing off an opening in the center, all plates equidistant from that center opening.

Furthermore, in accordance with another preferred embodiment of the present invention, the multiple plates are adapted to move simultaneously by means of a lever and transmission.

Furthermore, in accordance with another preferred embodiment of the present invention, there is provided a method for deploying an implantable prosthetic valve device from the retrograde approach (approaching the aortic valve from the descending aorta) or from the antegrade approach (approaching the aortic valve from the left ventricle after performing a trans-septal puncture) at the natural aortic valve position at the entrance to the left ventricle of a myocardium of a patient, the method comprising the steps of:

(a) providing a balloon catheter having a proximal end and a distal end, having a first and second independently inflatable portions, the first inflatable portion located at the distal end of the catheter and the second inflatable portion adjacently behind the first inflatable portion;

(b) providing a guiding tool for guiding the balloon catheter in the vasculature of the patient;

(c) providing a deployable implantable valve prosthesis device adapted to be mounted on the second inflatable portion of the balloon catheter;

(d) for the retrograde approach, guiding the balloon catheter through the patient's aorta using the guiding tool, the valve device mounted over the second inflatable portion of the balloon catheter until the first inflatable portion of the balloon catheter is inserted into the left ventricle, whereas the second inflatable portion of the balloon catheter is positioned at the natural aortic valve position;

(e) for the antegrade approach, guiding the balloon catheter through the patient's greater veins, right atrium, left atrium, and left ventricle using the guiding tool, the valve device mounted over the second inflatable portion of the balloon catheter until the first inflatable portion of the balloon catheter is inserted into the left ventricle, whereas the second inflatable portion of the balloon catheter is positioned at the natural aortic valve position;

(f) inflating the first inflatable portion of the balloon catheter so as to substantially block blood flow through the natural aortic valve and anchor the distal end of the balloon catheter in position;

(g) inflating the second inflatable portion of the balloon catheter so as to deploy the implantable prosthetic valve device in position at the natural aortic valve position;

(h) deflating the first and second inflatable portions of the balloon catheter; and (i) retracting the balloon catheter and removing it from the patient's body.

Furthermore, in accordance with another preferred embodiment of the present invention, the guiding tool comprises a guide wire.

Furthermore, in accordance with another preferred embodiment of the present invention, there is provided a method for deploying an implantable prosthetic valve device at the natural aortic valve position at the entrance to the left ventricle of a myocardium of a patient, the method comprising the steps of:

(a) providing a balloon catheter having a proximal end and a distal end, having a first and second independently inflatable portions, the first inflatable portion located at the distal end of the catheter and the second inflatable portion adjacently behind the first inflatable portion;

(b) providing a guiding tool for guiding the balloon catheter in the vasculature of the patient;

(c) providing a deployable implantable valve prosthesis device adapted to be mounted on the first inflatable portion of the balloon catheter, and a deployable annular stent device adapted to be mounted over the second inflatable portion of the balloon catheter, the deployable implantable valve prosthesis device and the deployable annular stent kept at a predetermined distant apart;

(d) guiding the balloon catheter through the patient's aorta using the guiding tool, the valve device mounted over the first inflatable portion of the balloon catheter and the deployable annular stent mounted over the second inflatable portion of the balloon catheter, until the first inflatable portion of the balloon catheter is positioned at the natural aortic valve position;

(e) inflating the second inflatable portion of the balloon catheter so that the deployable stent device is deployed within the aorta thus anchoring the deployable annular stent and the coupled valve device in position;

(f) inflating the first inflatable portion of the balloon catheter so as to deploy the implantable prosthetic valve device in position at the natural aortic valve position;

(g) deflating the first and second inflatable portions of the balloon catheter; and (h) retracting the balloon catheter and removing it from the patient's body.

Furthermore, in accordance with another preferred embodiment of the present invention, a valve prosthesis device suitable for implantation in body ducts comprises:

an expandable support frame, the support frame provided with a plurality of longitudinally rigid support beams of fixed length; and a valve assembly comprising a flexible conduit having an inlet end and an outlet, made of pliant material attached to the support beams providing collapsible slack portions of the conduit at the outlet, whereby when flow is allowed to pass through the valve prosthesis device from the inlet to the outlet the valve assembly is kept in an open position, whereas a reverse flow is prevented as the collapsible slack portions of the valve assembly collapse inwardly providing blockage to the reverse flow.

Furthermore, in accordance with another preferred embodiment of the present invention, the support frame comprises a deployable construction adapted to be initially crimped in a narrow configuration suitable for catheterization through the body duct to a target location and adapted to be deployed by exerting substantially radial forces from within by means of a deployment device to a deployed state in the target location.

Furthermore, in accordance with another preferred embodiment of the present invention, the support beams have a U-shaped cross section.

Furthermore, in accordance with another preferred embodiment of the present invention, a holder is used to secure the plaint material to the support beams.

Furthermore, in accordance with another preferred embodiment of the present invention, the support frame comprises three segments that form a circular assembly when assembled.

Furthermore, in accordance with another preferred embodiment of the present invention, the support beams point inwardly with respect to a central longitudinal axis of the device.

Furthermore, in accordance with another preferred embodiment of the present invention, the device is further provided with a restricting tapered housing, for housing it in a crimped state.

Furthermore, in accordance with another preferred embodiment of the present invention, hooks are provided to secure the device in position after it is deployed.

Furthermore, in accordance with another preferred embodiment of the present invention, the support beams comprise longitudinal bars having a narrow slit used as the commissural attachment so that extensions the pliant material are tightly inserted through it.

Furthermore, in accordance with another preferred embodiment of the present invention, the extensions of the pliant material are wrapped about rigid bars serving as anchorage means.

Furthermore, in accordance with another preferred embodiment of the present invention, extensions of the pliant material are sutured to each other at the rigid bars.

Furthermore, in accordance with another preferred embodiment of the present invention, a bottom portion of the pliant material is attached to the inlet.

Furthermore, in accordance with another preferred embodiment of the present invention, the support beams are each provided with a rounded pole, forming a loop through which the pliant material is inserted.

Furthermore, in accordance with another preferred embodiment of the present invention, the pliant material is provided with longitudinal bars attached to the pliant material at positions assigned for attachment to the support frame, in order to prevent localized stress from forming.

Furthermore, in accordance with another preferred embodiment of the present invention, the device is further provided with longitudinal bars having protrusions that are inserted in bores in the pliant material, a sheet of PET and through bores provided on the support beams.

Furthermore, in accordance with another preferred embodiment of the present invention, pliant material is sutured leaving the slack portions free of sutures.

Furthermore, in accordance with another preferred embodiment of the present invention, a connecting member with a split portion is used to connect leaflets of the pliant material to the support beams, the split connecting member compressing the pliant material in position.

Furthermore, in accordance with another preferred embodiment of the present invention, a portion of the connecting member is perpendicular to the split portion.

Furthermore, in accordance with another preferred embodiment of the present invention, the support frame is provided with metallic members coupled to the stent and rigid members are positioned on two opposite sides of the metallic member and held against each other holding portion of the pliant material between them, sutured, the metallic members wrapped with PET.

Furthermore, in accordance with another preferred embodiment of the present invention, the device is further provided with spring in order to reduce wear of the pliant material.

Furthermore, in accordance with another preferred embodiment of the present invention, the spring is provided with a spiral.

Furthermore, in accordance with another preferred embodiment of the present invention, the spring is made from stainless steel.

Furthermore, in accordance with another preferred embodiment of the present invention, the spring is attached to slots provided on the support frames.

Furthermore, in accordance with another preferred embodiment of the present invention, the pliant material is sutured to the support frame forming pockets.

Furthermore, in accordance with another preferred embodiment of the present invention, attachment bars are provided on the stent support at a portion of the stent close to the outlet, onto which the pliant material is coupled, and wherein the pliant material is attached circumferentially to the inlet, leaving slack pliant material.

Furthermore, in accordance with another preferred embodiment of the present invention, the outlet is tapered with respect to the inlet.

Furthermore, in accordance with another preferred embodiment of the present invention, the support frame at the outlet is wider in diameter than the pliant material forming the outlet.

Furthermore, in accordance with another preferred embodiment of the present invention, the pliant material is reinforced using PET.

Furthermore, in accordance with another preferred embodiment of the present invention, the support frame is a tube having an inner wall, having sinusoidal fold lines, wherein the pliant material is sutured to the inner wall of the tube along suture lines.

Furthermore, in accordance with another preferred embodiment of the present invention, additional piece of PET is added below the suture lines.

Furthermore, in accordance with another preferred embodiment of the present invention, the device is incorporated with an angioplasty balloon.

Finally, in accordance with another preferred embodiment of the present invention, balloon has a central longitudinal axis that runs along a flow path through the device, and a perimeter, the balloon comprising four inflatable portions, one portion located along a central axis and the other three located on the perimeter, the pliant material in the form of leaflets is distributed about the perimeter.

BRIEF DESCRIPTION OF THE FIGURES

To better understand the present invention and appreciate its practical applications, the following Figures are provided and referenced hereafter. It should be noted that the Figures are given as examples only and in no way limit the scope of the invention as defined in the appended claims.

FIGS. 6a to 6e illustrate manufacturing of an implantable valve by forging according to the present invention;

FIGS. 13a to 13c illustrate the manufacturing of a reinforced PU tube composed of strong fiber from PU, PET or other and a softer PU coating, for serving as the supporting structure;

FIGS. 15a to 15c demonstrate a valve with radio-opaque coating, according to the present invention, which allows imaging of the valve motion under angiogram;

FIGS. 17a and 17b describe a valve device according to the present invention, comprising one valve assembly mounted on a stent and an additional portion with a stent only. This allows placing the device in a way that coronaries are not blocked, longitudinal positioning thus becomes less sensitive and the extra stent decreases the risk of device migration within the vasculature;

FIG. 24a depicts an isometric view of the frame, and FIG. 24b depicts a cross-sectional view of the means for mounting a valve leaflet in details, provided with a valve leaflet. FIG. 24c depicts further details of attachment means for the attachment method;

FIGS. 25a and 25b depict an isometric view and an upper view of the valve assembly, respectively, and FIGS. 25c and 25d illustrate upper views of two optional constructions for the means for mounting leaflets;

FIG. 26a is the valve in its fully expanded diameter, FIG. 26b is a tapered tool which assists in inserting the valve into an introducing tube, and FIG. 26c shows the valve assembly inside a restriction tube, ready to be inserted into a introducing sheath;

FIGS. 30a to 30c illustrate an isometric view, a cross-sectional view and a flattened view, respectively, of an attachment assembly of a valves frame to leaflets in accordance with another preferred embodiment of the present invention. FIG. 30c is a side view showing two pieces of pericardium before the attachment to the frame;

In FIGS. 34b and 34c, a deployed portion and the folded portion, respectively, are shown;

FIG. 37b is an isometric view of the connecting bar;

FIGS. 40b and 40c depicts a cross-sectional side view and an isometric view, respectively, of the pericardium that is sutured to a PET tube in the form of pockets;

FIGS. 41a to 41d illustrate isometric views of an implantable prosthesis tricuspid valve in accordance with yet another preferred embodiment of the present invention;

FIG. 42b depicts the attachment in details;

FIG. 43a depicts the commissure that are pre-sutured in a tapered shape;

FIGS. 45a to 45d illustrate an isometric view of an implantable prosthetic valve in accordance with yet another preferred embodiment of the present invention, having leaflets sutured to a pre-shaped PET tube and optional leaflet-tube attachments in details;

FIGS. 47b and 47c are cross sectional upper views in the inflated and deflated positions, respectively.

DETAILED DESCRIPTION OF THE INVENTION

Figure 1:
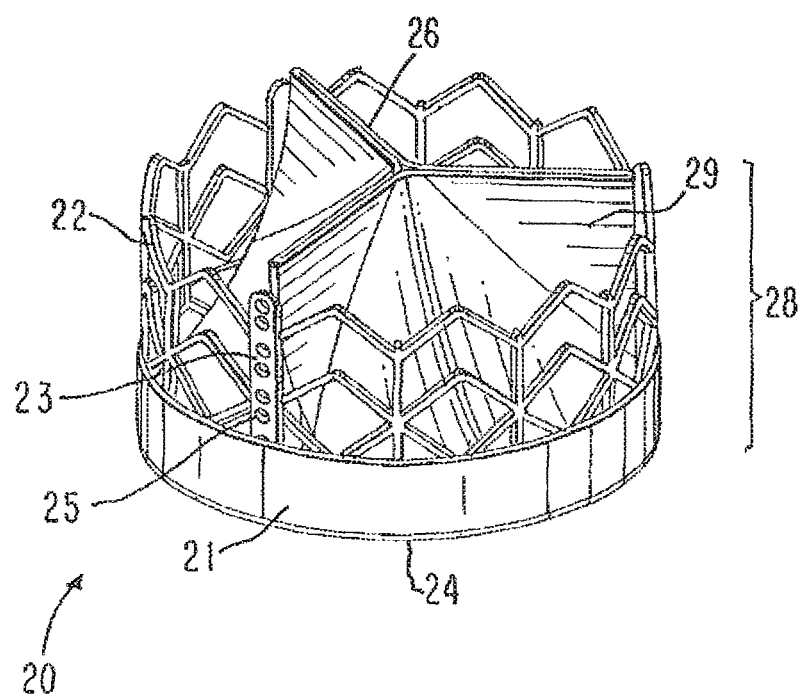
FIG. 1 illustrates an implantable prosthetic tricuspid valve in accordance with a preferred embodiment of the present invention, suitable for percutaneous deployment using a stent or similar deploying means, in its deployed-inflated position.

A main aspect of the present invention is the introduction of several novel designs for an implantable prosthetic valve. Another aspect of the present invention is the disclosure of several manufacturing methods for implantable prosthetic valves in accordance with the present invention. A further aspect of the present invention is the provision of novel deployment and positioning techniques suitable for the valve of the present invention.

Basically the implantable prosthetic valve of the present invention comprises a leafed-valve assembly, preferably tricuspid but not limited to tricuspid valves only, consisting of a conduit having an inlet end and an outlet, made of pliant material arranged so as to present collapsible walls at the outlet. The valve assembly is mounted on a support structure such as a stent adapted to be positioned at a target location within the body duct and deploy the valve assembly by the use of deploying means, such as a balloon catheter or similar devices. In embodiments suitable for safe and convenient percutaneous positioning and deployment the annular frame is able to be posed in two positions, a crimped position where the conduit passage cross-section presented is small so as to permit advancing the device towards its target location, and a deployed position where the frame is radial extended by forces exerted from within (by deploying means) so as to provide support against the body duct wall, secure the valve in position and open itself so as to allow flow through the conduit.

The valve assembly can be made from biological matter, such as a natural tissue, pericardial tissue or other biological tissue. Alternatively, the valve assembly may be made form biocompatible polymers or similar materials. Homograph biological valves need occasional replacement (usually within 5 to 14 years), and this is a consideration the surgeon must take into account when selecting the proper valve implant according to the patient type. Mechanical valves, which have better durability qualities, carry the associated risk of long-term anticoagulation treatment.

The frame can be made from shape memory alloys such as nickel titanium (nickel titanium shape memory alloys, or NiTi, as marketed, for example, under the brand name Nitinol), or other biocompatible metals. The percutaneously implantable embodiment of the implantable valve of the present invention has to be suitable for crimping into a narrow configuration for positioning and expandable to a wider, deployed configuration so as to anchor in position in the desired target location.

The support stent is preferably annular, but may be provided in other shapes too, depending on the cross-section shape of the desired target location passage.

Manufacturing of the implantable prosthetic valve of the present invention can be done in various methods, by using pericardium or, for example, by using artificial materials made by dipping, injection, electrospinning, rotation, ironing, or pressing.

The attachment of the valve assembly to the support stent can be accomplished in several ways, such as by sewing it to several anchoring points on the support frame or stent, or riveting it, pinning it, adhering it, or welding it, to provide a valve assembly that is cast or molded over the support frame or stent, or use any other suitable way of attachment.

To prevent leakage from the inlet it is optionally possible to roll up some slack wall of the inlet over the edge of the frame so as to present rolled-up sleeve-like portion at the inlet.

Furthermore, floating supports may be added to enhance the stability of the device and prevent it from turning inside out.

An important aspect of certain embodiments of the present invention is the provision of rigid support beams incorporated with the support stent that retains its longitudinal dimension while the entire support stent may be longitudinally or laterally extended.

The aforementioned embodiments as well as other embodiments, manufacturing methods, different designs and different types of devices are discussed and explained below with reference to the accompanying drawings. Note that the drawings are only given for the purpose of understanding the present invention and presenting some preferred embodiments of the present invention, but this does in no way limit the scope of the present invention as defined in the appended claims.

Reference is now made to FIG. 1, which illustrates a general tricuspid implantable prosthetic valve 20 in accordance with a preferred embodiment of the present invention, suitable for percutaneous deployment using an expandable stent or similar deploying means, shown in its deployed position. A valve assembly 28 comprises a conduit having an inlet 24 and an outlet 26, the outlet walls consisting of collapsible pliant material 29 that is arranged to collapse in a tricuspid arrangement. The valve assembly 28 is attached to an annular support stent 22, the one in this figure being a net-like frame designed to be adapted to crimp evenly so as to present a narrow configuration and be radially deployable so as to extend to occupy the passage at the target location for implantation in a body duct. Support beams 23 are provided on annular support stent 22 to provide anchorage to valve assembly 28. Support beams 23 are optionally provided with bores 25 to allow stitching of valve assembly 28 to support beams 23 by thread, wires, or other attachment means.

In the embodiment shown in FIG. 1, a cuff portion 21 of the valve assembly 28 is wrapped around support stent 22 at inlet 24 to enhance the stability. Preferably cuff portion 21 of valve material 28 is attached to support beams 23.

Note that the entire valve structure is adapted to be radially crimped and radially expanded, and this lends to provide ease of navigation through narrow passages in the vasculature during positioning of the device and adequate deployment on the final location. This is made possible by the provision of a collapsible support stent structure. However, the support beams remain at all times constant at their length and thus are suitable for serving as the pliable valve assembly's anchorage. The valve assembly is attached to the support stent at the support beams, and due to their constant length there is no need for slack material as the attachment points (25) remain at constant distances regardless of the position of the valve device (crimped or deployed). This is an important feature for this means that the manufacturer of the valve device can make sure the valve assembly is secured and fastened to the support stent at all times. In prior art implantable valve devices the entire support structure changes its dimensions from its initial first crimped position and final deployed position, and this means that in the attachment of the valve assembly to the support structure one must take into consideration these dimension changes and leave slack material so that upon deployment of the device the valve assembly does not tear or deform. In the valve device of the present invention there is no relative movement between the valve assembly and the support beams (along the longitudinal central axis of the device). As a result, the valve device of the present invention acquires greater durability and is capable of withstanding the harsh conditions prevailing within the vasculature and especially the millions of cycles of stress applied by the blood pressure.

The fixed attachment of the valve assembly to the support stent in the valve device of the present invention results in greater stability, enhanced safety, better sealing and consequently longer lifespan. The novel design of the valve device of the present invention leads to longitudinal strength and rigidity whereas its collapsible support structure results in radial flexibility.

Figure 2:
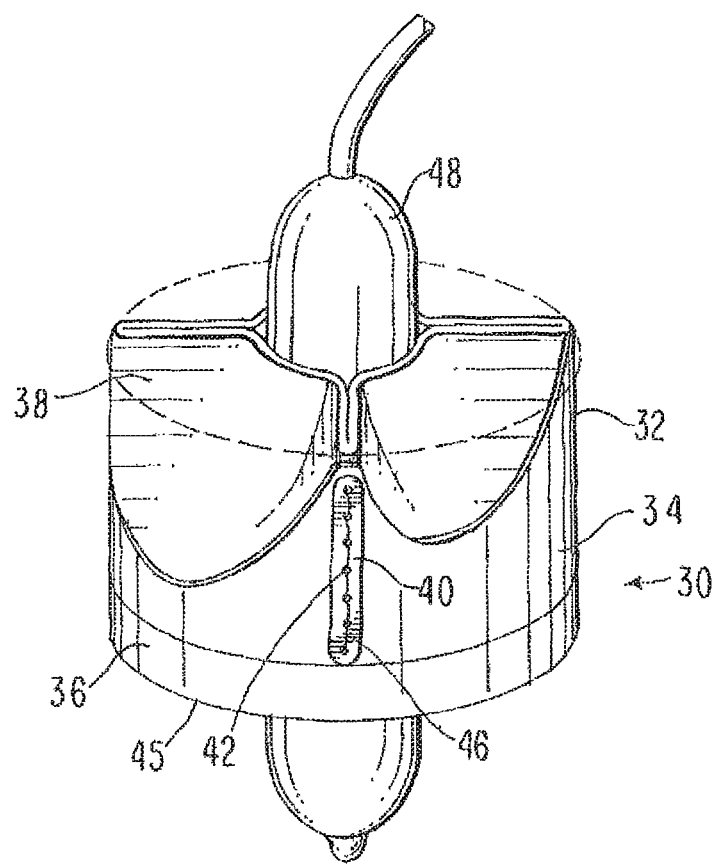
FIG. 2 depicts an implantable valve according to the present invention mounted over a deploying stent with an inflatable balloon.

FIG. 2 depicts an implantable valve 30 mounted on a deployable stent 32. The valve assembly 34 is attached to the deployable support stent 32 (dotted lines) along three substantially equidistant and substantially parallel support beams 40 of constant length, which are part of stent 32. The attachment of valve assembly 34 to stent 32 is facilitated by the support beams 40 to which valve assembly 34 is stitched with thread or fiber 46 (through bores 42 of support beams 40). Outlet leafs 38, which are a slack portion of the valve assembly, dangle inwardly, and the whole device is carried by an inflatable balloon 48, which serves as the deploying device. A portion of the valve assembly 34 at an inlet zone 45 is optionally rolled over support stent 32 at the inlet, making up a rolled sleeve, which enhances the sealing of the device at the valve inlet.

Figure 3:
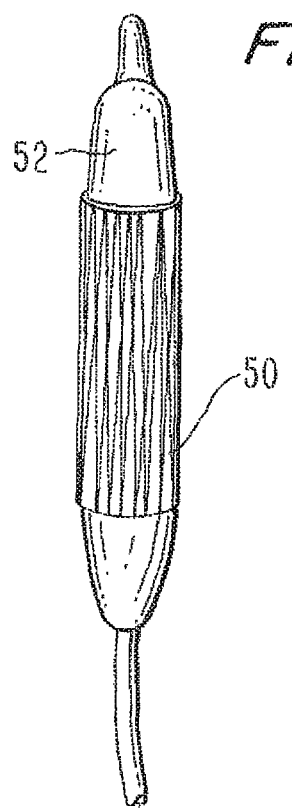
FIG. 3 illustrates an implantable valve according to the present invention mounted over a stent with an inflatable balloon, in a crimped position.

FIG. 3 demonstrates an implantable valve mounted to a stent 50 with an inflatable balloon 52, in a crimped position. The support stent 50 is initially crimped about the balloon 52 so that is presents a narrow cross-section and is thus suitable for percutaneous catheterization and deployment.

Figure 4:
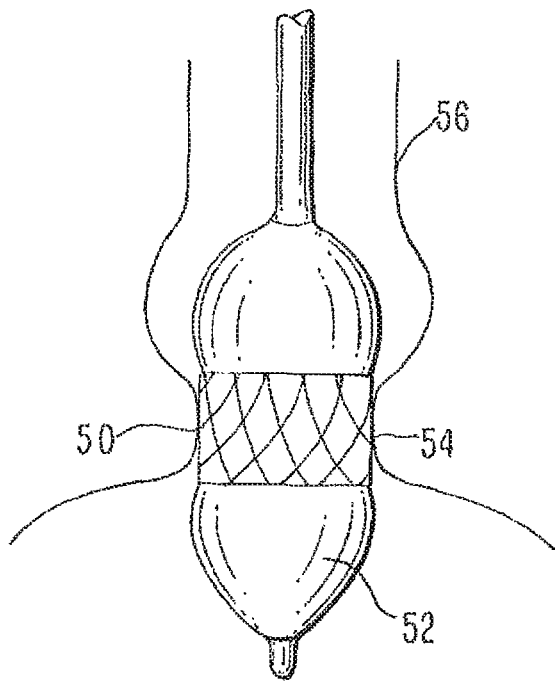
FIG. 4 depicts implantable valve deployment in a natural aortic valve position in accordance with the present invention.

FIG. 4 depicts an implantable valve deployment in a natural aortic valve position. The implantable valve is advanced while mounted over the balloon 52 until it reaches the desired target location 54 in a body duct, for example, aorta 56. The balloon is inflated and the support stent 50 expands radially to take up its position.

Figure 5:
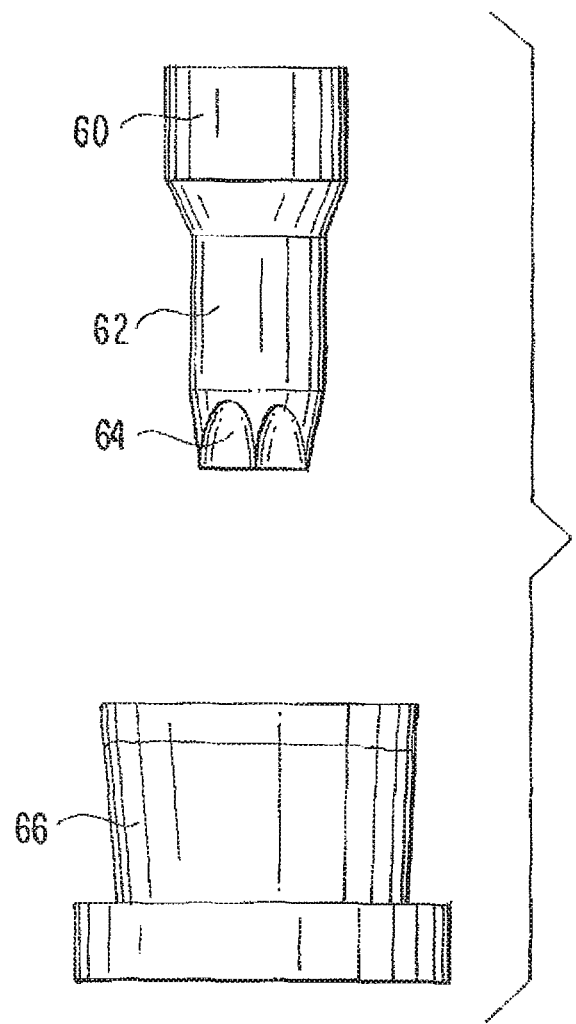
FIG. 5 demonstrates manufacturing a polyurethane implantable valve using a dipping technique according with the present invention.

FIG. 5 demonstrates the manufacture of a polyurethane valve in a dipping technique. A dipping mandrel 60 is provided with a tubular portion 62 with surfaces 64 that correspond to the collapsible valve leaflets to be manufactured. Mandrel 60 is dipped into a dissolved polyurethane bath 66 and is coated with a polyurethane coating in the desired form of the valve. Then, after the polyurethane coating has hardened sufficiently, the completed valve is removed from mandrel 60.

Figure 6A:
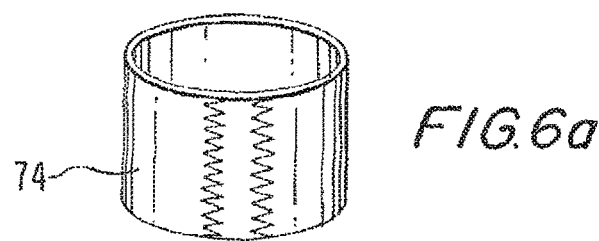
Figure 6B:
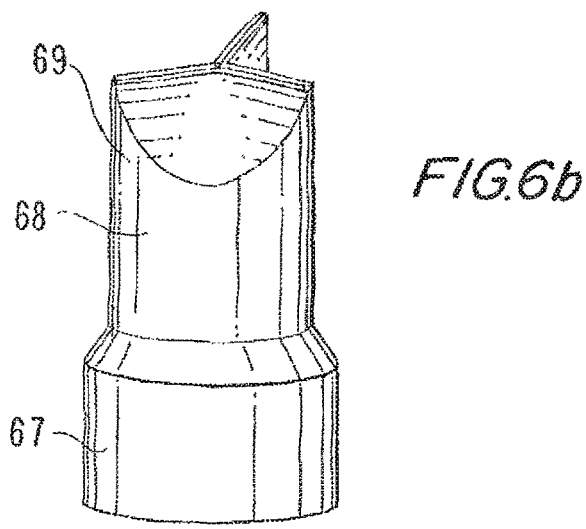
Figure 6C:
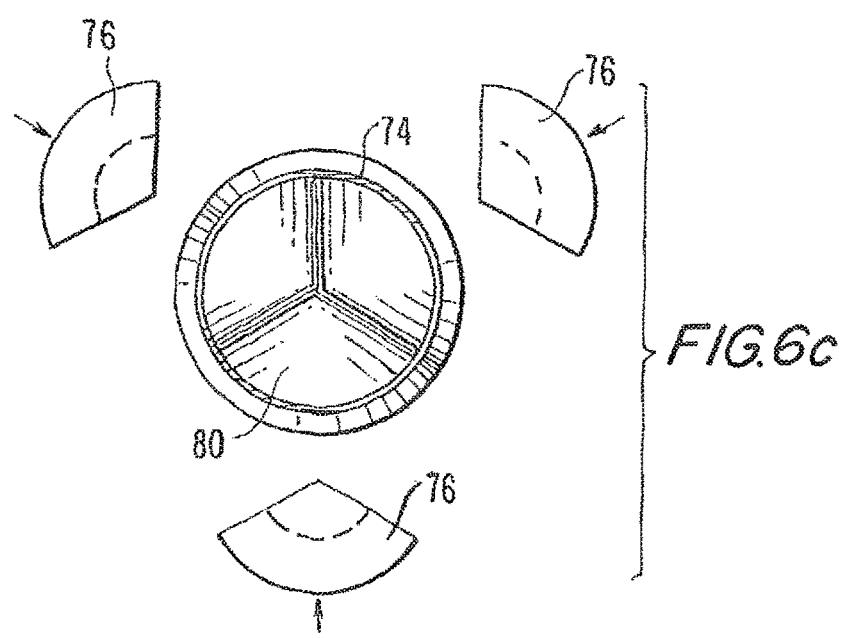

FIGS. 6a to 6e illustrate manufacturing an implantable valve by forging. A suitable tubularly shaped material 74 is placed tightly on a tubular portion 68 of mandrel 67, covering the cusp portion 69. Flexible inserts 76 are pressed to mandrel 67, forging the tubular material to mandrel shape 80. A tapered ring 70 holds the flexible inserts in place as the whole mold is placed in a hot oven regulated to a desired temperature, which is lower than the material's melting point. FIG. 6e illustrates a sectional side view of the mandrel and a cross cut portion of the mold. The mold is made to press inwardly on the mandrel, which is covered with the valve material. As a result the material takes up the desired shape. The materials used can vary, for example, polyurethane (PU), polyethylene terephthalate (PET), or any other suitable material, which may be formed by heating.

Figure 7A:
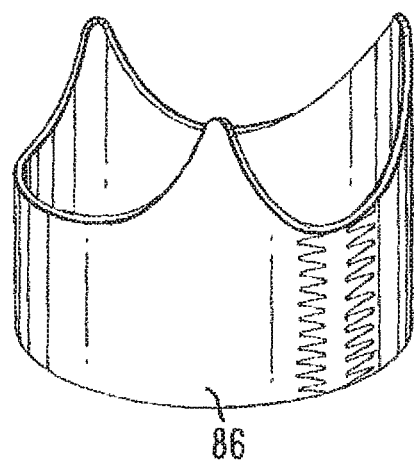
FIGS. 7a and 7b demonstrate composite valve, which has polyurethane (PU) leaflets and PET tubular-crown shaped construction, according to the present invention.
Figure 7B:
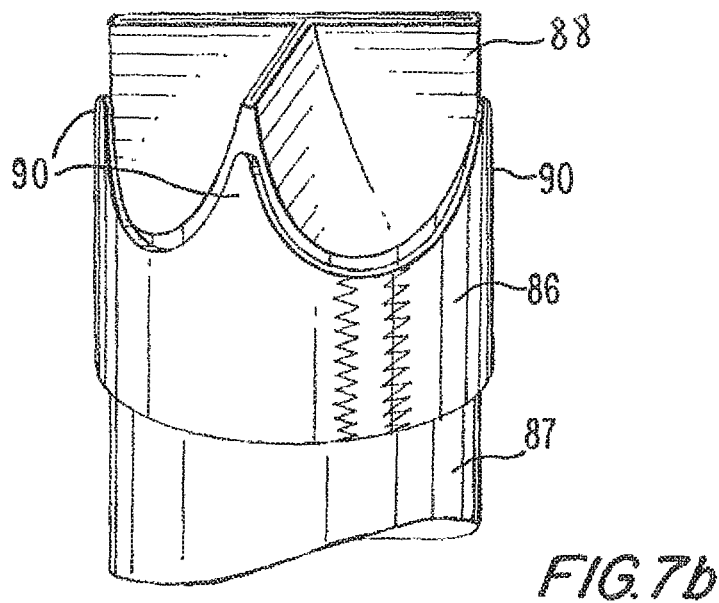

FIGS. 7a and 7b demonstrate a method of manufacturing a composite valve, which has PU leaflets and PET tubular construction with a crown shape. PU is an excellent fatigue resistant material but is sensitive to tear. The PU is reinforced by the PET crown to allow safe attachment to a stent by means of stitching, riveting, or any other suitable attachment method. A PET crown 86 is placed on a mandrel 87, which is then (turned and) dipped in a container of dissolved PU. The manufactured device is a valve assembly having leaflets 88 composed of pure PU, and thus fatigue resistant, and a main body made of PET with protruding attachment portions 90 suitable for attachment built in the PU.

Figure 8A:
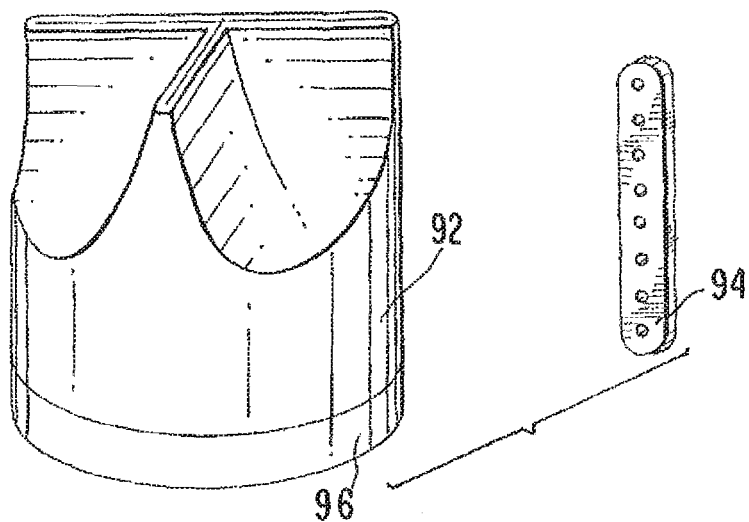
FIGS. 8a and 8b depict a manufacture process of a composite valve made of flexible PU leaflets, rigid PU construction for mounting and a PET tubular end.
Figure 8B:
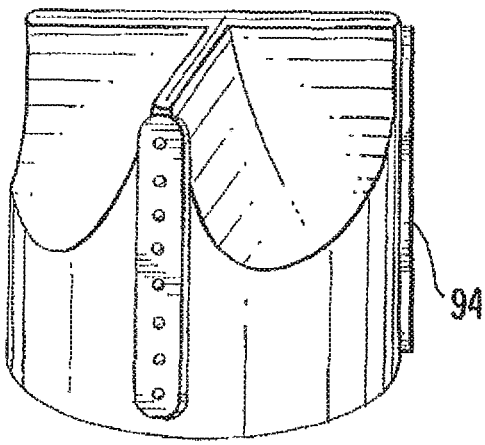

FIGS. 8a and 8b demonstrate a method of manufacturing a composite valve, which is based on flexible PU 92 for as the main body of the valve, rigid PU support beams 94 serving for the attachment area, and PET sleeve 96 portions for the valve inlet. The need for a rigid portion for attachment (support beams 94) is explained by the tendency of the flexible, fatigue resistant material to tear as already explained. The advantage of the stiff PU support beams is that they are chemically adhered to the main body, and this improves the overall durability of the valve due to reduction of inner forces and friction in the attachment area specially attachment between two different materials. The valve is dipped in the method mentioned with reference to FIG. 5, and the rigid PU support beam 94 is created by way of mold injection, machining or any other suitable way. The rigid PU support beam 94 is placed on the valve and then dipped into the container of dissolved PU. This is done while the valve is positioned on the mandrel (not shown). This method provides the ability to composite several materials into one body and, by that, gain the advantage of the various properties of the materials as they are needed in different areas of the prosthesis.

Figure 9E:
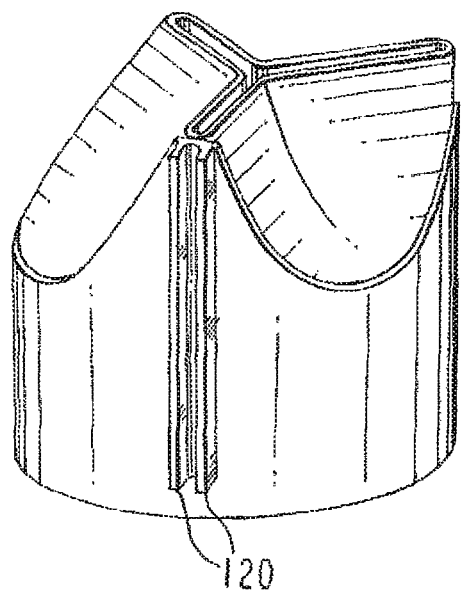
FIGS. 9 to 9i demonstrate different methods of attachment between the valve and stent according to the present invention.
Figure 9F:
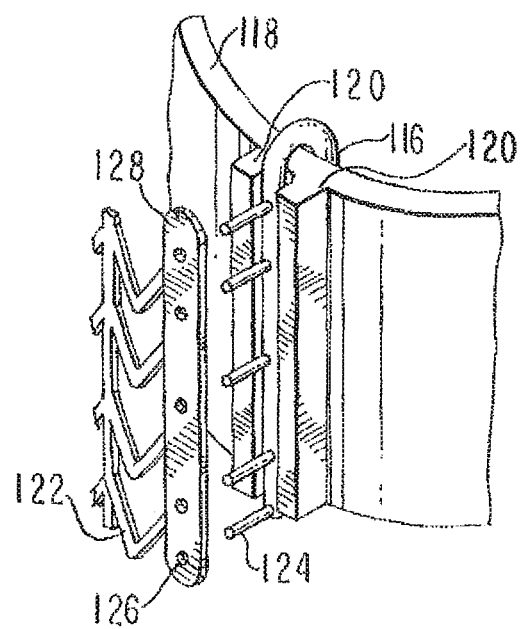
Figure 9G:
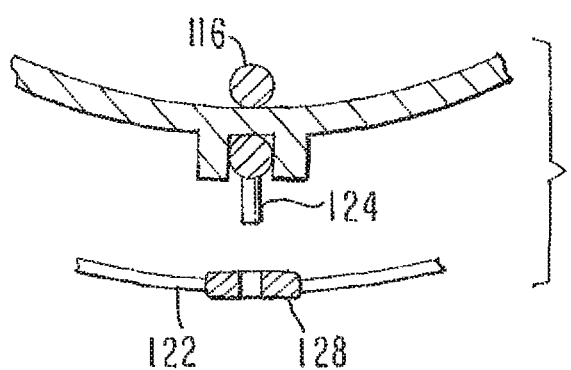
Figure 9H:
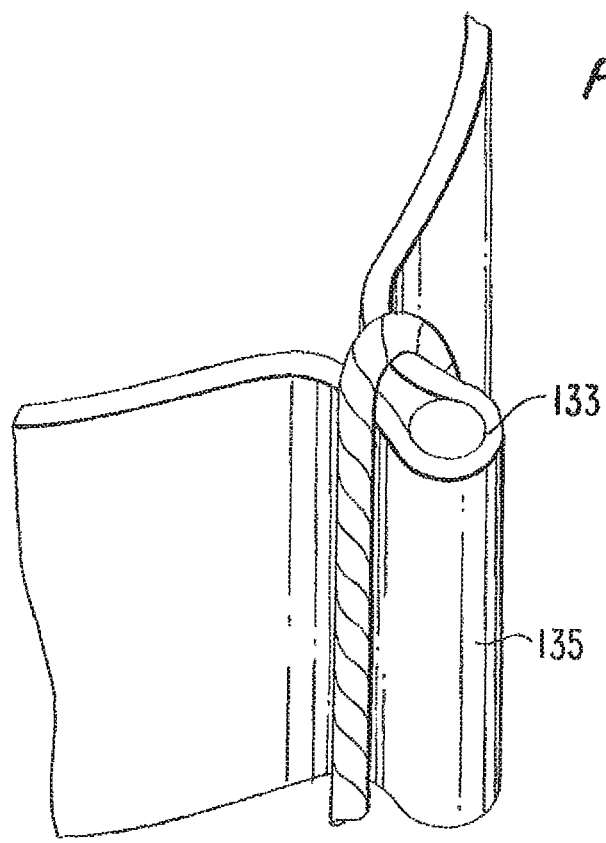
Figure 9I:
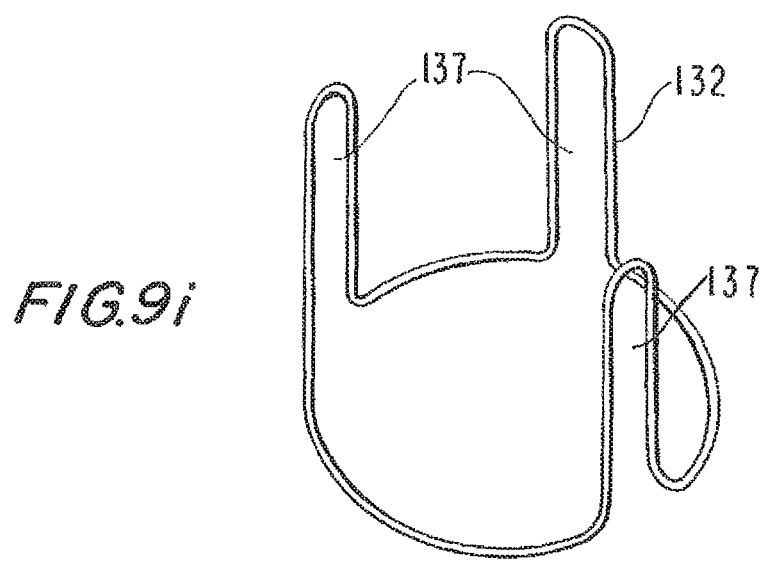

FIGS. 9 to 9i demonstrate different methods of attachment between a valve assembly and the support stents. A valve assembly 99 shown in FIG. 9 is incorporated into valve 100 shown in FIG. 9a, where a support stent 102 is attached to valve assembly 99 through support beam 106. A detail is shown in FIG. 9b, where, in cross-section, it can be seen that layer 108 is an optional inner support made of stainless steel or rigid polymeric material, valve assembly 99 comprises a PET layer 105 coated with a PU layer 104, with the outer support beam 106. Connector 107 is a connecting wire made of a strong material, such as stainless steel. FIG. 9c illustrates an alternative arrangement for attachment by a rivet 109, and in FIG. 9d the attachment is achieved by a suture 110.

FIGS. 9e to 9g show an attachment method comprising shaped rigid members 116, preferably made from metal, which tightly hold the PU valve material 118 by fitting in between a PU U-shaped nest 120 and are attached to a stent 122 by extruding portions 124 that are provided on U-shaped rigid member 116, which fit the bores 126 of the support beam 128 of the stent 122. FIGS. 9h and 9i show another attachment method, where rigid support beams in the form of frame construction 132 are provided, and the valve assembly pliant material 135 made of a tubular material is inserted through a gap 137 in the frame. After insertion, a fastening rod 133 is inserted through the pocket formed between the pliant material and the frame and holds the valve in position.

Figure 10:
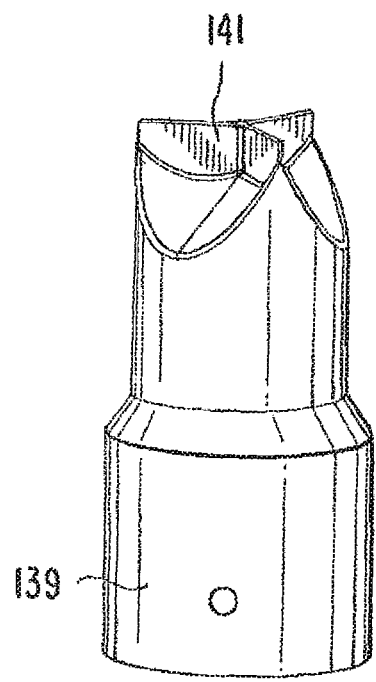
FIG. 10 illustrates a dipping mandrel with an extra portion, which improves the sealing ability of the valve, according to the present invention.

FIG. 10 illustrates a dipping mandrel 139 with an extending portion 141, which improves the sealing ability of the valve. Since the valve is attached to a collapsible stent and is itself collapsible, it is difficult to determine the exact shape of the valve after crimping and deploying. It is of major importance that sealing will be achieved. By adding the extension 141 the leaflets are made longer than needed to exactly close the outlet, and therefore when they are in the collapsed state, substantial portions of the leaflets fall on each other creating better sealing.

Figure 11A:
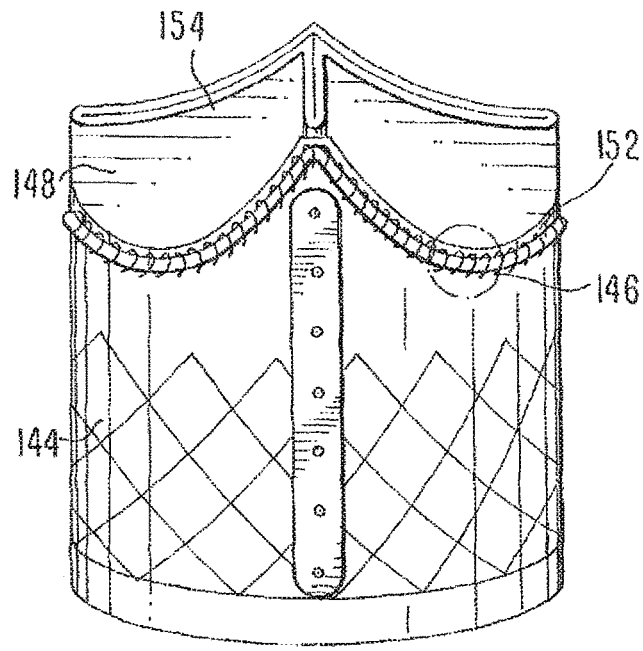
FIGS. 11a to 11c illustrate a valve mounted on a stent with an extra support, which improves the force distribution on the valve material and facilitates prolonged durability of the valve, according to the present invention.
Figure 11B:
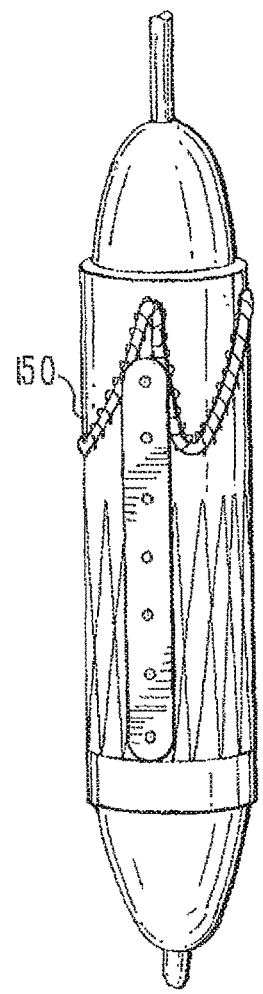
Figure 11C:
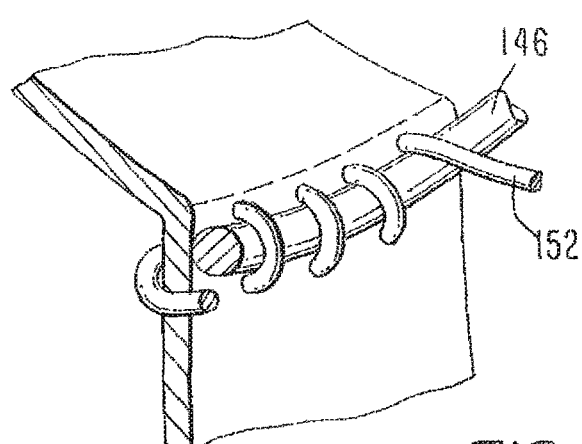

FIGS. 11a to 11c illustrate a valve assembly mounted on a support stent 144 with interlaced strengthening wire 146, which improves the force distribution on the valve material and facilitates prolonged durability of the valve. The support is in the form of a wire, which has a crown shape as the shape of the three cusp valve base 148, it also has the ability to be crimped 150 to a small diameter, together with the stent, valve and balloon, as shown in FIG. 11b. The forces applied to the valve edge 148 while working, are applied to the attachment points, by making the attachment line longer we reduce the force on each attachment point. In this support method the valve is attached by suturing 152 the entire line to the extra support wire 146. This wire can be made of stainless steel, nickel titanium alloy such as nitinol, or polymeric material. The support suture renders the valve assembly default fault lines where the valve material more readily flexes, thus ensuring proper operation of the valve flaps (leaflets). Optionally the valve assembly shown in FIGS. 11a to 11c can be mounted on a support stent such as the one described herein or similar supporting structures. The strengthening wire is interlaced in the valve assembly at the outlet of the conduit so as to define a fault line about which the collapsible slack portion 154 of the valve assembly may flap.

Figure 12A:
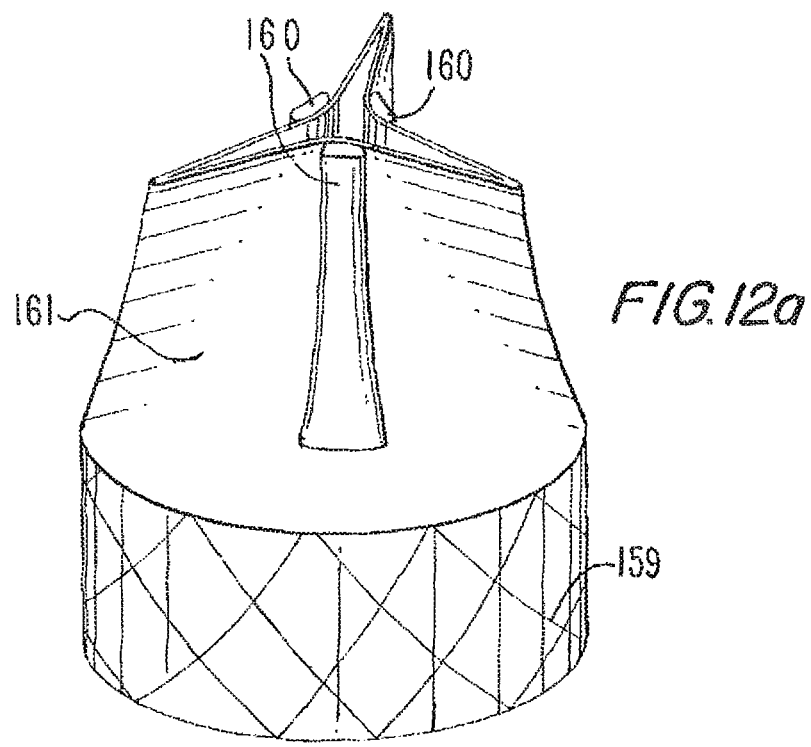
FIGS. 12a to 12c depict a valve with rigid supports according to the present invention, located substantially in the center of its leaflets. This design allows the valve leaflets to perform without outer support.
Figure 12B:
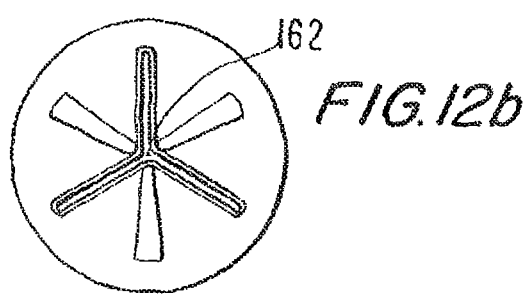
Figure 12C:
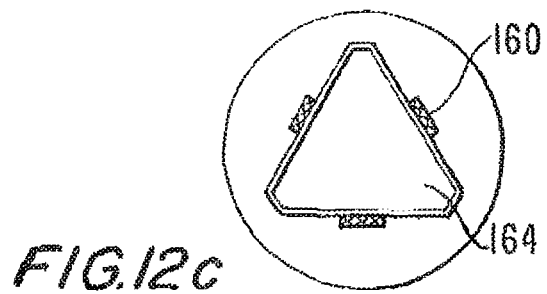

FIGS. 12a to 12c depict a valve device provided with a stent 159 and substantially equidistant rigid support beams 160, interlaced or attached to the slack portion of the valve assembly material 161, arranged longitudinally. This design allows the valve leaflets to perform without outer support. The support in standard valves is by tying the upper edge of the cusp to a rigid embodiment, so that it reacts to the load as a suspension bridge. In this new design the prevention of collapsing is achieved similar to an Indian tent, i.e., the rigid supports lean on each other 162 when the valve is closed but do not interfere in opening 164 when the valve is open.

FIGS. 13a to 13c illustrate the manufacturing of a valve assembly in accordance with another preferred embodiment of the present invention. At first a polyurethane thread line 170 is fed from a PU supply 172, and coiled around a cylindrical drum 174 to form coil 176. Then, drum 174 with coil 176 is dipped in a PU bath 177, and a second layer 178 of the PU coats coil 176, making it a stronger construction capable of withstanding tearing forces both laterally and in other directions. Incorporating two different types of materials—such as PU and PET—may render greater durability and endurance to the valve assembly. This material is an alternative material to be used in the forging method shown in FIG. 6.

Figure 14:
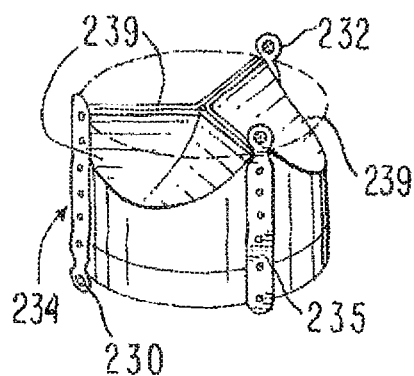
FIGS. 14 and 14a to 14c demonstrate incorporation of heavy metal markers on the stent, according to the present invention. These markers allow orientation control while positioning the device at the required location.
Figure 14A:
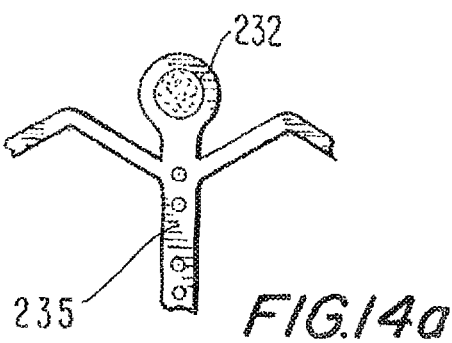
Figure 14B:
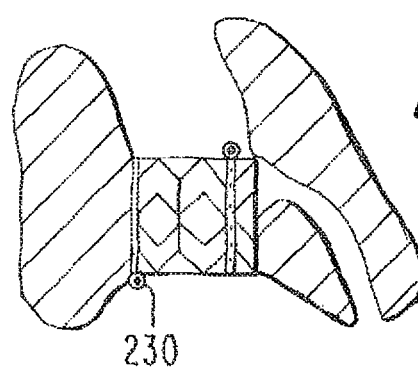
Figure 14C:
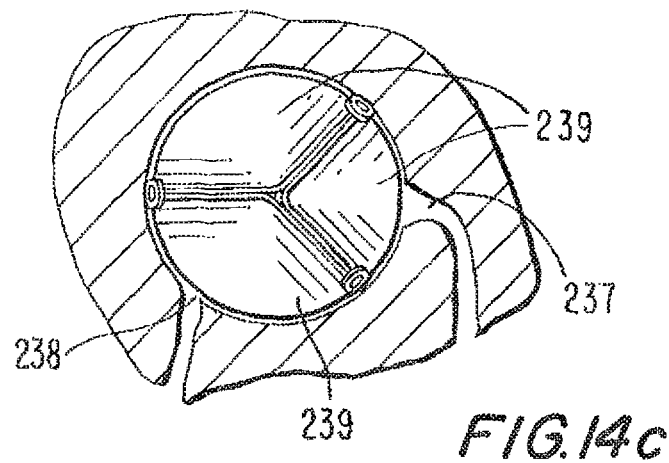

FIGS. 14 to 14c demonstrate the incorporation of heavy metal markers on the stent, which markers allow observation and thereby adjustment of orientation while placing the device in the required location. Heavy metals are radiopaque, that is, they are conspicuous on an angioscopic image, which is a two-dimensional image. Since the coronary artery ostia 237 and 238 are located near the typical valve deployment location and must stay open, it is extremely important to make sure that the deployed valve assembly is not blocking a coronary ostium. In some cases the stent is lower than the ostium and in those cases it will stay open, but in some cases as shown in these figures it is necessary to make sure that the stent portion 239 that is connecting the valve supports 235 is opposite the coronary ostia, and in that way the blood supply is preserved through the stent struts. Two heavy metal markers 232 are attached at the outlet side, one marker 230 at the inlet side. It is possible to adjust the angiogscopic view to the plane of the left coronary as shown in FIG. 14*b* and anatomically locate the other accordingly. If the two upper markers 232 are placed in the radiographic two dimensional image, one on top of the other, and the low marker 230 on the opposite side, we make sure that the coronaries are open to blood flow as seen in FIG. 14*c*. Gold, platinum, iridium or tantalum are all biocompatible materials suitable for the markers described above.

FIGS. 15*a* to 15*c* illustrate a valve with a portion of radio-opaque material 267 such as a thread of gold at the sealing edge. When a valve is implanted, it is very important to have clear indications of how the valve is functioning in vivo; pressure measurements, flow visualization, and doppler measurements are utilized. It is also possible to examine the valve by ultrasound methods, however, observing the opening and closing of the valve cusps on a monitor. FIG. 15*b* is an angiographic image 268 of the open valve, while image 169 in FIG. 15*c* is the closed position as seen on the angiogram.

Figure 16A:
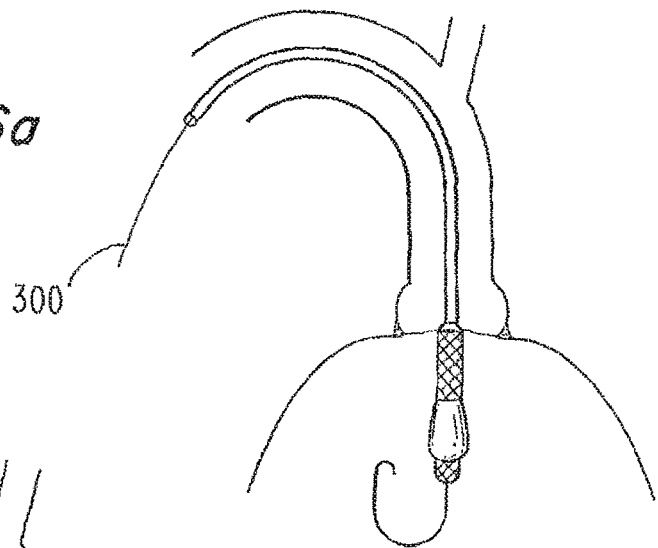
FIGS. 16a to 16c illustrate a procedure, which helps in accurate positioning the valve device with respect to the longitudinal orientation.
Figure 16B:
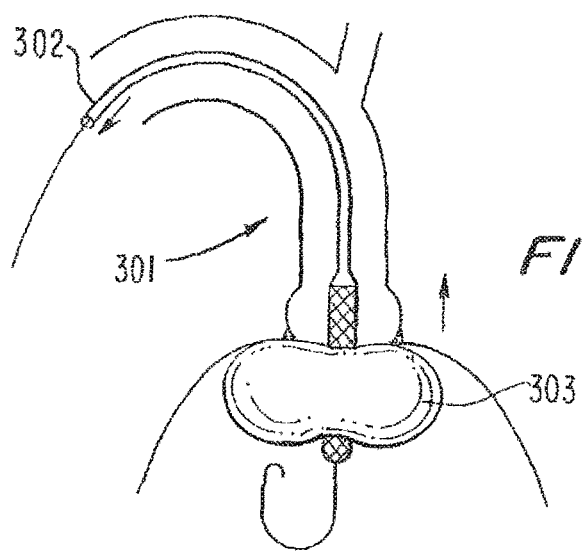
Figure 16C:
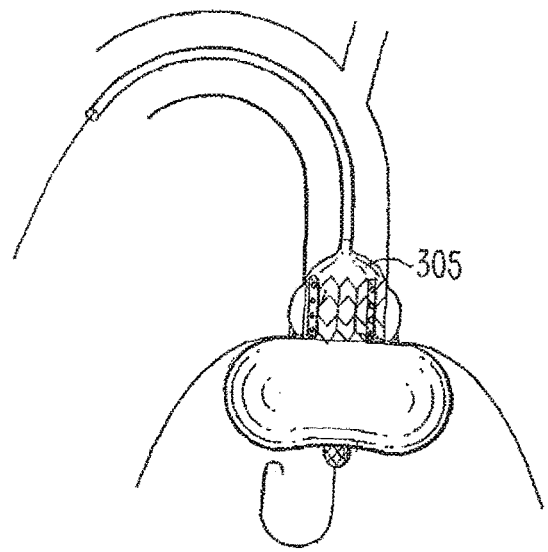

FIGS. 16*a* to 16*c* illustrate a procedure, which helps in placing the device in the longitudinal position. It is very important to place the device in the correct longitudinal position, for if it is too deep in the left ventricle it may interfere with the mitral valve function by improper closing or function of the valve. If it is positioned too high it may migrate, it may leak via the sinus cavities, which are located around it, and/or it may block the coronaries. It is a necessary task to position the valve prosthesis in a narrow target location. In FIG. 14 a method of lateral orientation placement is shown, and FIGS. 16*a* to 16*c* illustrate a longitudinal positioning. The valve device (the valve assembly and the support stent) is placed on an inflatable balloon catheter, comprising double independently inflatable chambers 303, 305, and is inserted into the left ventricle 302 in the crimped position and guided over a guiding stylet or guide wire 300. The balloon, which is larger than the annulus diameter when inflated, is inflated in the left ventricle 302, and then the whole device is pulled slightly backwards. The balloon is supported on the inner part of the annulus 303, allowing positioning of the device in the exact desired position. In addition, it temporarily blocks the blood flow, and that improves the ability to hold the device in place while inflating it. The next step is inflating the second balloon 305, which deploys the valve device in the desired location.

The method for deploying an implantable prosthetic valve device at the natural aortic valve position at the entrance to the left ventricle of a myocardium of a patient, as depicted in FIGS. 16*a*, 16*b* and 16*c*, comprises the steps of:

(a) providing a balloon catheter having a proximal end and a distal end, having a first and second independently inflatable portions, the first inflatable portion located at the distal end of the catheter and the second inflatable portion adjacently behind the first inflatable portion;

(b) providing a guiding tool for guiding the balloon catheter in the vasculature of the patient;

(c) providing a deployable implantable valve prosthesis device adapted to be mounted on the second inflatable portion of the balloon catheter (d) guiding the balloon catheter through the patient's aorta using the guiding tool, the valve device mounted over the second inflatable portion of the balloon catheter until the first inflatable portion of the balloon catheter is inserted into the left ventricle, whereas the second inflatable portion of the balloon catheter is positioned at the natural aortic valve position;

(e) inflating the first inflatable portion of the balloon catheter so as to substantially block blood flow through the natural aortic valve and anchor the distal end of the balloon catheter in position;

(f) inflating the second inflatable portion of the balloon catheter so as to deploy the implantable prosthetic valve device in position at the natural aortic valve position;

(g) deflating the first and second inflatable portions of the balloon catheter; and (h) retracting the balloon catheter and removing it from the patient's body.

FIGS. 17*a* and 17*b* describes a positioning of a valve device 310 using an additional deployable stent 320. There are several problems that may be encountered while deploying the stent and valve in the aortic valve location: blockage of coronaries may occur that is dangerous if the diameter of the stent is similar to that of the coronaries aortic root 309. Secondly, migration of the whole device may also occur, which is a dangerous possibility, and there is the problematic challenge of exact positioning of the valve device that is very difficult to accomplish, as already explained. The newly special designed device with a double diameter inflatable balloon and double stent design allows placement of the device in a way that coronaries will not be blocked because of a safe difference that is kept between the diameters, longitudinal placing is less sensitive because of the small diameter which ensures prevents over expansion of the valved prosthesis. The distal stent 320, which contains no valve, is expanded into the ascending aorta, while the proximal stent 310 is placed simultaneously in the annular position. This placement method is less challenging due to the smaller diameter of the proximal stent 310 which ensures that the mitral valve is not deformed by over-expansion as the dimensions are preserved, and the additional stent decreases the risk of device migration. It is safer to over dilate in the aorta, which is not true for the annulus.

The method for deploying an implantable prosthetic valve device at the natural aortic valve position at the entrance to the left ventricle of a myocardium of a patient, as depicted in FIGS. 17*a* and 17*b*, comprises the steps of:

(a) providing a balloon catheter having a proximal end and a distal end, having a first and second independently inflatable portions, the first inflatable portion located at the distal end of the catheter and the second inflatable portion adjacently behind the first inflatable portion;

(b) providing a guiding tool for guiding the balloon catheter in the vasculature of the patient;

(c) providing a deployable implantable valve prosthesis device adapted to be mounted on the first inflatable portion of the balloon catheter, and a deployable annular stent device adapted to be mounted over the second inflatable portion of the balloon catheter, the deployable implantable valve prosthesis device and the deployable annular stent kept at a predetermined distant apart;

(d) guiding the balloon catheter through the patient's aorta using the guiding tool, the valve device mounted over the first inflatable portion of the balloon catheter and the deployable annular stent mounted over the second inflatable portion of the balloon catheter, until the first inflatable portion of the balloon catheter is positioned at the natural aortic valve position;

(e) inflating the second inflatable portion of the balloon catheter so that the deployable stent device is deployed within the aorta thus anchoring the deployable annular stent and the coupled valve device in position;

(f) inflating the first inflatable portion of the balloon catheter so as to deploy the implantable prosthetic valve device in position at the natural aortic valve position;

(g) deflating the first and second inflatable portions of the balloon catheter; and (h) retracting the balloon catheter and removing it from the patient's body.

Figure 18B:
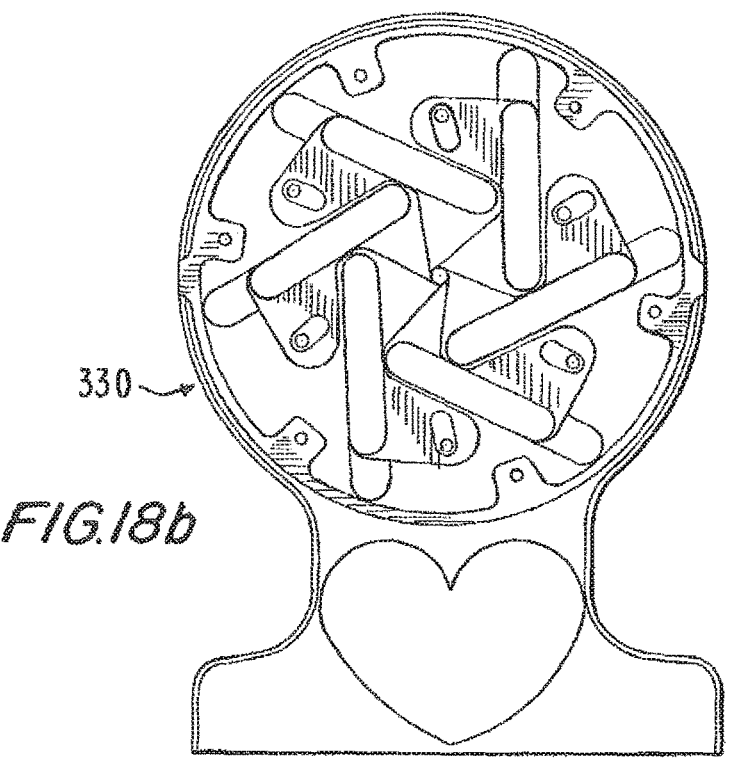
FIGS. 18a and 18b demonstrate a crimping device according to the present invention, which can crimp a valve device in the operating theater as part of the implantation procedure.
Figure 18A:
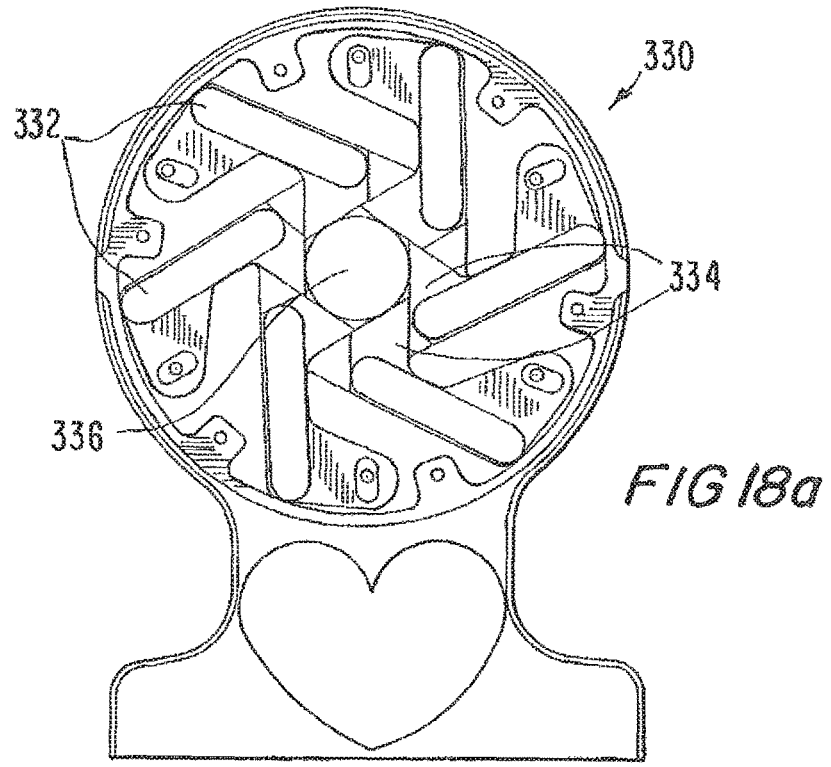

FIGS. 18a and 18b illustrate an accessory crimping device that is adapted to crimp a valve device in the operating theater as part of the implantation procedure. The crimping device 330 comprises several adjustable plates that resemble a typical SLR camera variable restrictor. It is comprised of simultaneously movable plates 332 each provided with a blade 334, that are equally dispersed in a radial symmetry but each plate moves along a line passing off an opening in the center, all plates equidistant from that center opening 336. Initially (see FIG. 18a) the plates are drawn apart providing a large enough opening for the implantable valve to be positioned within that opening. When the plates are drawn towards the center (see FIG. 18b), the opening 336 reduces in size but still retains the annular shape, and this facilitates the crimping of the valve frame to a small dimension suitable for percutaneous positioning.

Figure 19A:
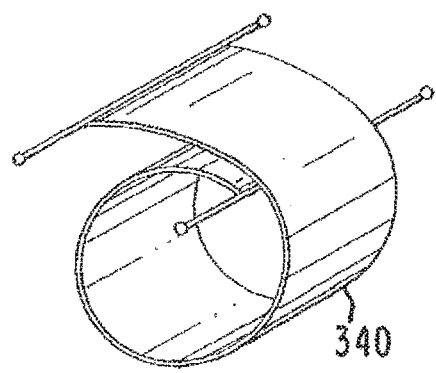
FIGS. 19a to 19c depict a crimping machine according to the present invention, similar to the one described in FIG. 18 with a different mechanical method.
Figure 19B:
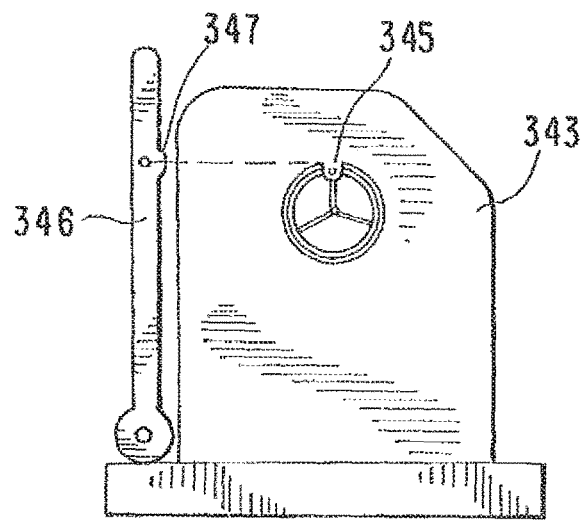
Figure 19C:
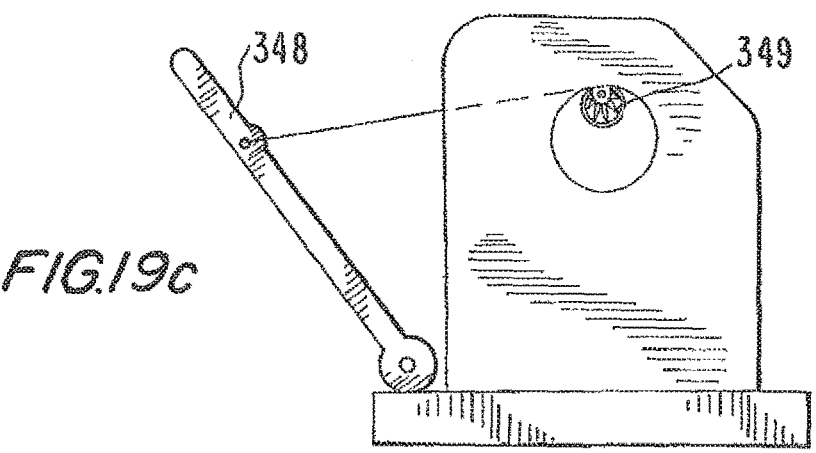

FIG. 19a depicts a crimping method for the support stent of the valve prosthesis device of the present invention, whereby stent 340 is crimped, that is, compressed or curled. In FIG. 19b a crimping device 343 is shown, comprising a body having an annular void in which an expanded stent is positioned. Lever 346 is connected to the end 347 of the stent and as the lever is pulled the stent is curled or compressed about axle 345 into a compressed position 349 (FIG. 19c).

Figure 20A:
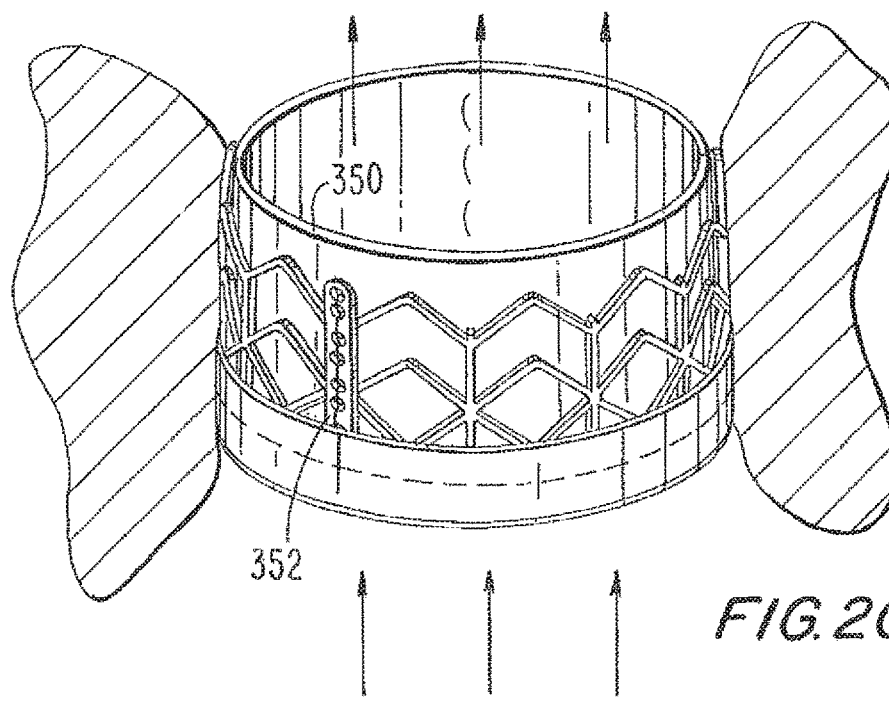
FIGS. 20a and 20b demonstrate a valve according to the present invention, made of a tube mounted on a stent. During systole the tube is fully open and during diastole the tube collapses according to the mounting geometry providing tight sealing.
Figure 20B:
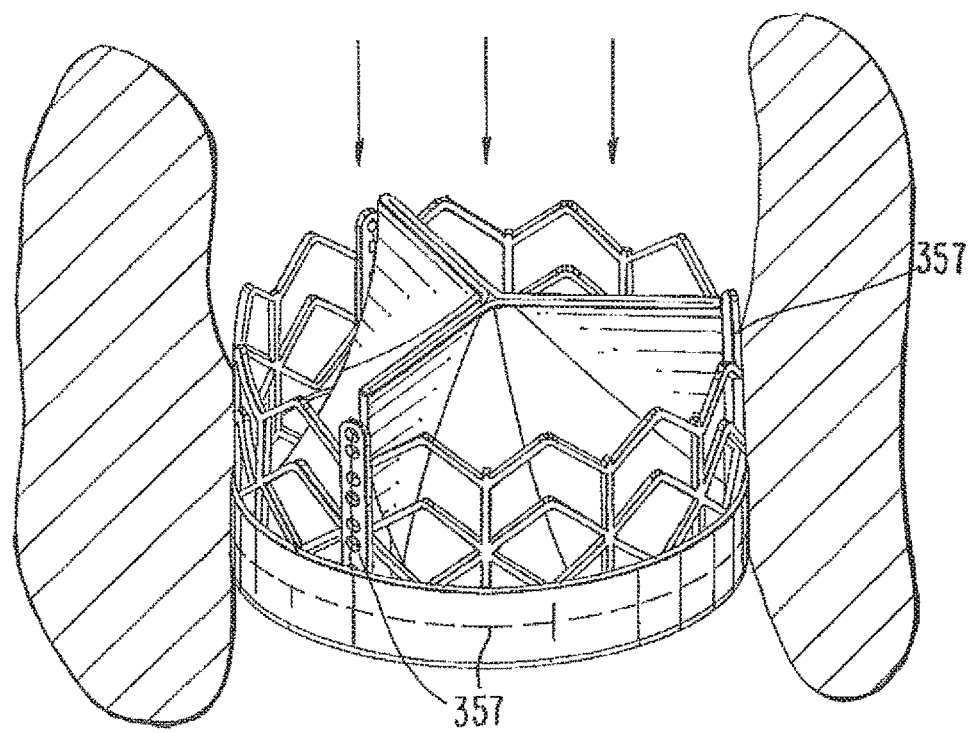

FIGS. 20a and 20b depict a valve made of a simple tube mounted to a stent 352. During systole period the tube is fully open and during diastole period the tube collapses according to the mounting geometry 357 and achieves sealing.

Figure 21:
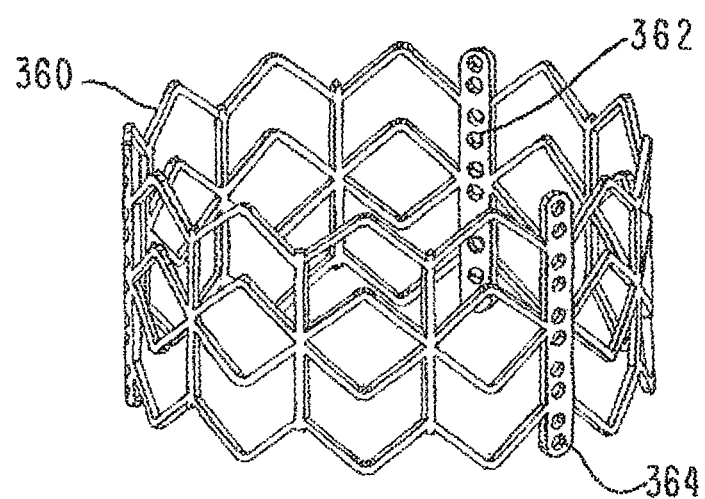
FIG. 21 depicts a stent structure according to the present invention, with built-in mounting portions of constant length, which allow valve mounting.

FIG. 21 describes a newly designed support stent 360 in its open position. Three of the longitudinal struts 362 are full and thick and always stay with their original constant size, serving as anchoring support. Each of these struts 362 is provided with a plurality of bores 364, which are later used for mounting the valve assembly (not shown) and tying it to stent 360. Between struts 362 a web-like construction is provided, which is capable of being crimped to a narrow state and capable of being deployed again to a wider state.

Figure 22:
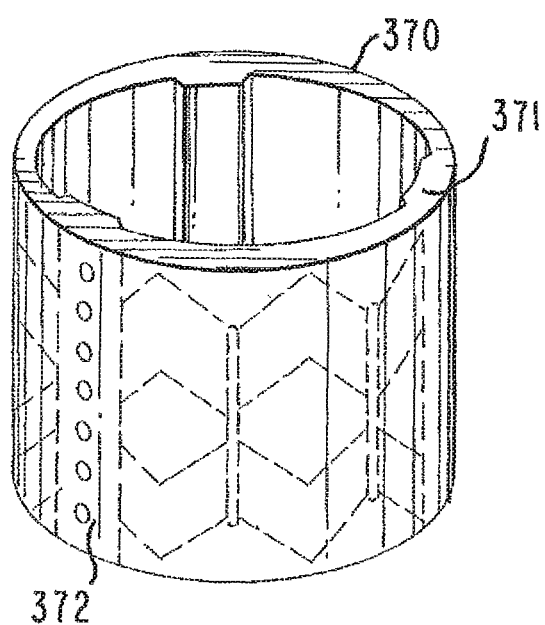
FIG. 22 depicts yet another preferred embodiment a valve assembly in accordance with the present invention, having dilated supports.

FIG. 22 illustrates another preferred embodiment of an implantable prosthetic valve according to the present invention. It comprises a metal tube 370, having three portions with a thicker wall 371 than in the rest of the tube 370, these areas form the longitudinal columns 372 in the construction, after the tube is cut to its final form. The advantage of such a construction is in its superior bending strength, in specific required portions of the construction, with minimal interference to the crimped volume of the whole construction.

Figure 23A:
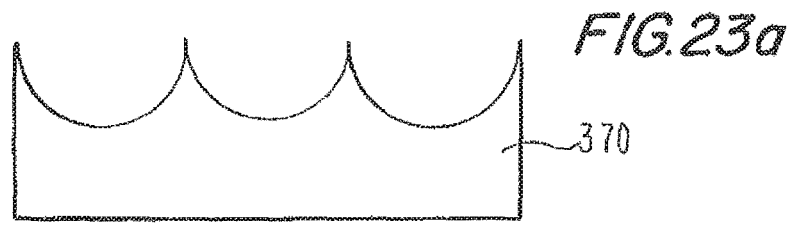
FIGS. 23a to 23e depict stages in a method of manufacturing an implantable prosthetic valve in accordance with another preferred embodiment of the present invention.
Figure 23B:
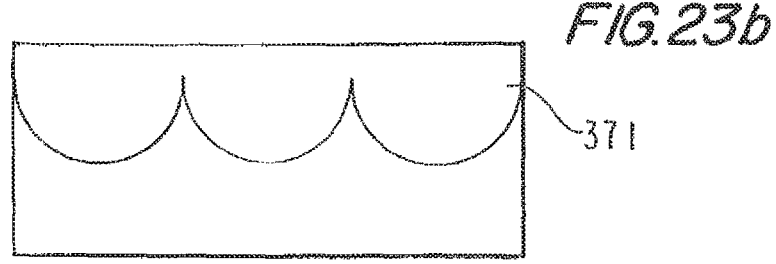
Figure 23C:
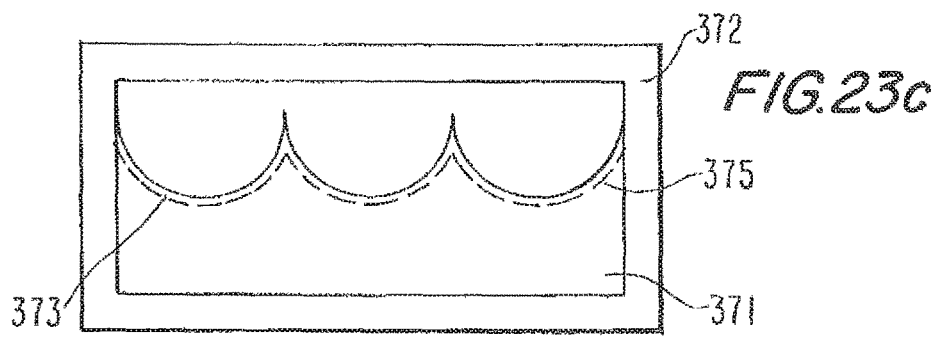
Figure 23D:
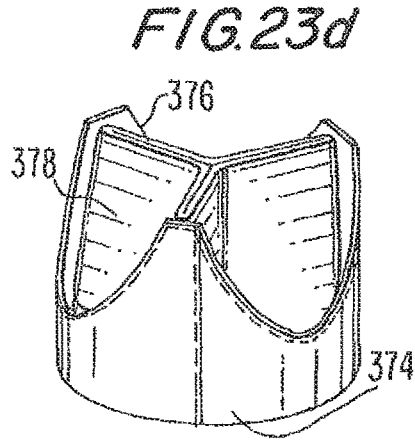
Figure 23E:
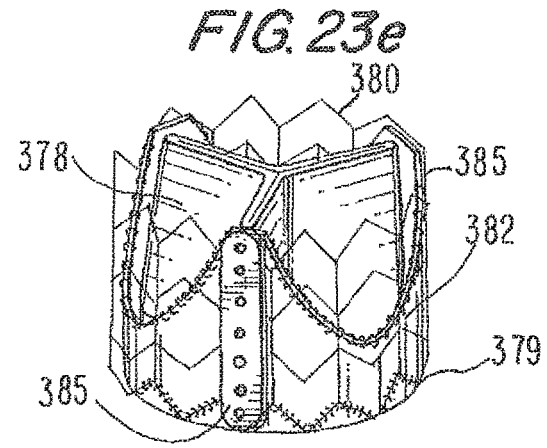

FIGS. 23a to 23c depict a new method of manufacturing an artificial or biological crimpable valve device. A piece of fabric material 370 (FIG. 23a), is dipped in PU to create a portion which is later formed into valve leaflets 371 (FIG. 23b). This composite material 371 is then attached to an additional piece of fabric such as PET 372 by means of stitching, suturing or other attaching technique 373 (FIG. 23c). The resulting fabric 375 is cut along stitching line 373 leaving enough material to later suture the valve assembly to the support construction. It is then formed to a tubular shape and stitched 374 (FIG. 23d). The tubular valve is then attached to a support construction 380 by suturing the bottom part around the valve 379 tightly to prevent leakage, and around the cut fabric line 376 (FIG. 23e). This open wall structure 378 allows blood flow to the coronary arteries. The valve is later placed with the coronary artery between the support columns 385. Additional variations of this can be made by replacing the composite material 371/370 with a biological patch such as a suitable pericardium patch. In some cases it is possible to make the same valve without cutting the fabric 372 with the shaped cut 376, and by that create a valve with an outer tubular shape. The embodiment of FIGS. 23a to 23c is easy to manufacture as it is generally flat throughout most of the production process and only at the final stage of mounting on the support stent is it given a three-dimensional form.

Figure 24A:
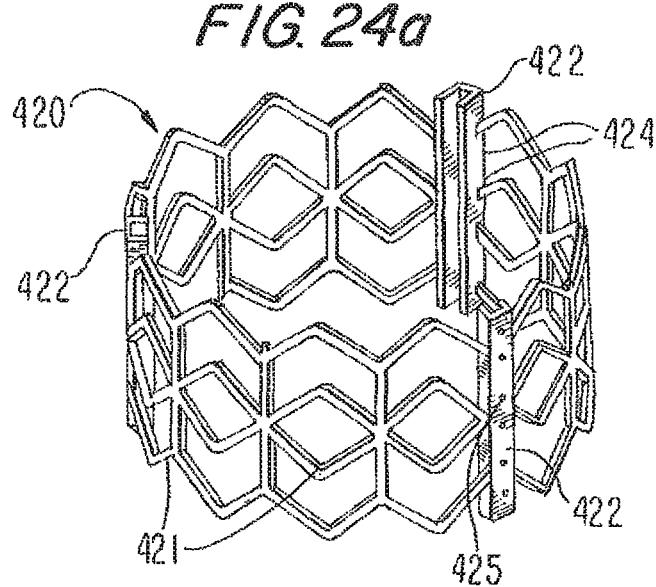
FIGS. 24a to 24c illustrate a support frame of an implantable prosthetic valve having means for mounting valve leaflets in accordance with a preferred embodiment of the present invention that can form a tricuspid valve.
Figure 24C:
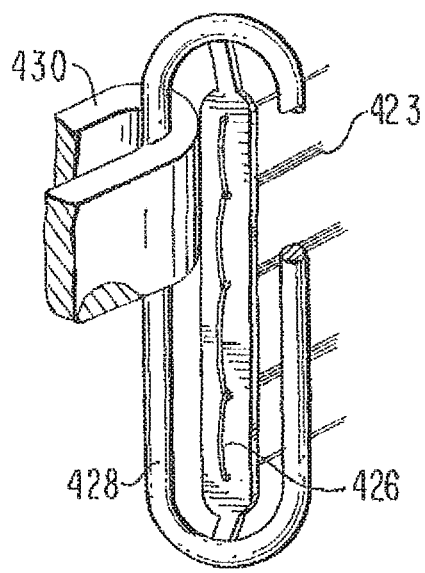
Figure 24B:
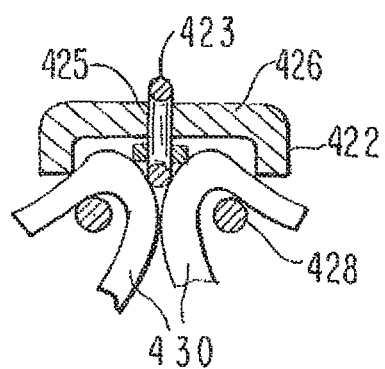

Reference is now made to FIG. 24a illustrating a frame of an implantable prosthetic valve having means for mounting valve leaflets in accordance with a preferred embodiment of the present invention that can form a tricuspid valve. FIG. 24a depicts an isometric view of the frame and FIG. 24b depicts a cross sectional view of the means for mounting valve leaflets 430 in detail. A frame 420, which is suitable for crimping and expanding, has three support beams 422 for mounting leaflets positioned substantially symmetrically about the circumference of the frame. Frame 420 is shown in FIG. 24a in its deployed state. Support beam 422 has a "U" shaped lateral cross section, or profile (shown clearly in FIG. 24b) that is designed to attach to a commissure of the valve structure. The "U" shape can be produced by extrusion, wire cutting or by welding the "U" profile to the frame's struts 421 at junction points 424. Support beam 422 is provided with a series of bores 425 positioned along its back wall. Bores 425 are designated for stitching the valve assembly by threads, wires, or other attaching means.

FIG. 24b is a detailed cross-sectional view of one of the support beam 422. Two pericardial leaflets 430 are inserted through a U-shaped, or forked holder 428 that compresses and restricts the leaflets in the U-shaped profile. Leaflets 430 are folded to both sides of the support beam 422. When holder 428 is compressed toward the support beam 422, leaflets 430 are caught in-between holder 428 and support beam 422 so that the leaflets are kept in place. FIG. 24c is an exploded view of the holder, bar 426 has a series of bores compatible for attachment to the frames support beam 422, attachment being achieved by suture 423 or any other attachment means. This attachment method allows attaching the leaflets to the frame without puncturing it with sutures and needles. It is also important that the leaflets are firmly held in place by the holder 428 so that it has no relative movement in respect to the rigid frame; hence avoiding wear due to movements. Leaflets that are made from pericardium are known to better withstand inner movements and stresses and less to wear by movement against rigid, hard or sharp bodies.

It is noted again that the entire valve structure is adapted to be radially crimped and radially expanded. This feature imparts the valve with the ability and ease to navigate through narrow passages in the vasculature during positioning of the device. After final positioning of the valve, the valve is deployed. This is made possible by the provision of a collapsible support frame structure. However, the length of the attaching means (the height of the valve) remains at all times constant; thus suitable for serving as the pliable valve assembly's anchorage. The leaflets are attached to the support frame at the attaching means, and due to their constant length there is no need for slack material as these attachment points that remain at constant distances regardless of the position of the valve assembly (crimped or deployed). This is an important feature for this means that the manufacturer of the valve device can make sure the valve assembly is secured and fastened to the support frame at all times. In prior art implantable valve devices, the entire support structure changes its dimensions from its initial first crimped position to final deployed position and this means that in the attachment of the valve leaflets to the support structure one must take into consideration these dimension changes and leave slack material so that upon deployment of the device, the valve assembly does not tear or deform. In the valve device of the present invention there is no relative movement between the valve leaflets and the support beams (along the longitudinal central axis of the device). As a result, the valve device of the present invention acquires greater durability and is capable of withstanding the harsh conditions prevailing within the vasculature and especially the millions of cycles of stress applied by the blood pressure.

The fixed attachment of the valve leaflets to the support frame in the valve assembly device of the present invention renders it greater stability, enhanced safety, better sealing and consequently longer lifespan. The novel design of the valve device of the present invention renders it longitudinal strength and rigidity whereas its collapsible support structure renders it radial flexibility.

Figure 25A:
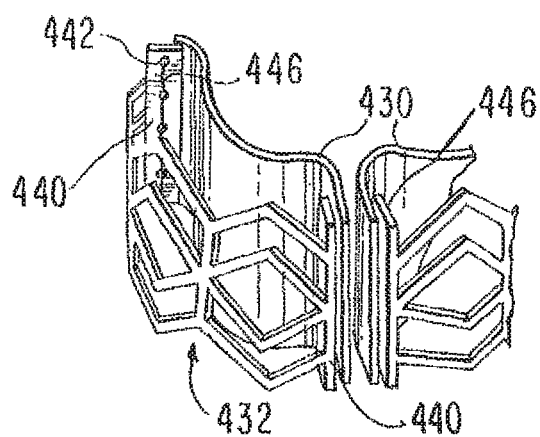
FIGS. 25a to 25d illustrate an implantable prosthetic valve in accordance with another preferred embodiment of the present invention.
Figure 25B:
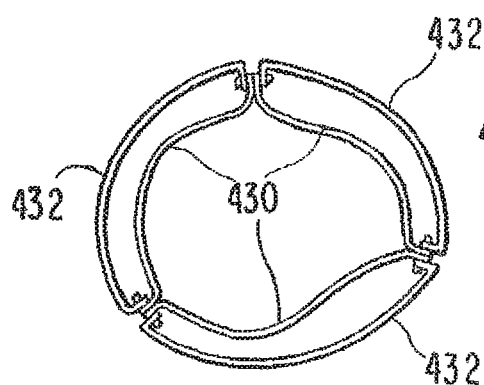
Figure 25C:
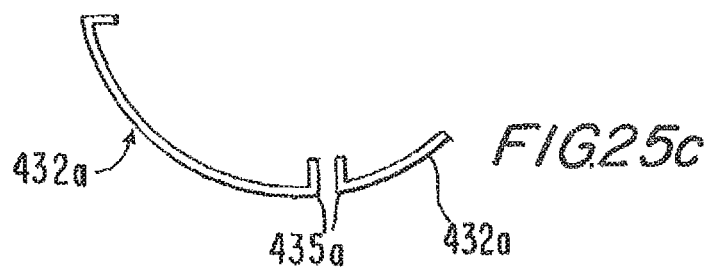
Figure 25D:
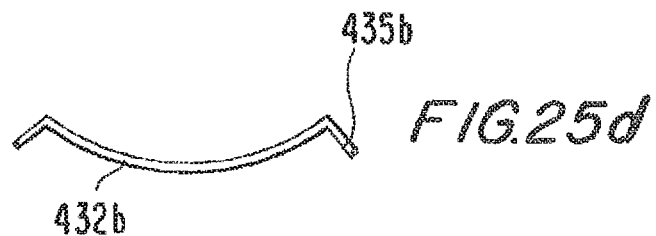

FIGS. 25a to 25d illustrate an implantable prosthetic valve in accordance with another preferred embodiment of the present invention. FIGS. 25a and 25b depict an isometric view and an upper view of the valve assembly, respectively and FIGS. 25c and 25d illustrate upper views of two optional constructions for the means for mounting leaflets. Pericardial leaflets 430 are mounted on a deployable support frame 432. The frame is preferably made of three segments that form a circular support frame when assembled (FIG. 25b). Pericardial leaflets 430 are attached to deployable support frame 432 along three substantially equidistant and substantially parallel beams 440, which are integral parts of support frame 432. Leaflets 430 are attached to support frame 32 at support beams 440 by suturing 446 leaflets 446 to support beams 440 through bores 442 in beams. The frame segments that are preferably made from stainless steel are pre-shaped 432 and can be formed in different ways. FIG. 25c illustrates support frame segments 432a having beams 435a pointing inwardly. FIG. 25d illustrates support frame segments 432b having beams 435b that are outwardly pointing. The advantages of this technique are the possibility to manufacture the frame segments from sheets (as opposed to tube) and the ease of assembly of the frame segments with the pericardial leaflets.

Figure 26A:
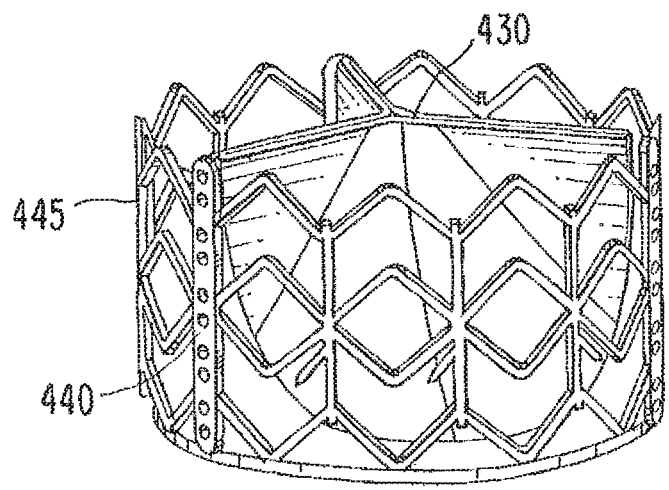
FIGS. 26a to 26c illustrate a tricuspid valve in accordance with yet another preferred embodiment of the present invention, provided with a self-expandable frame.
Figure 26B:
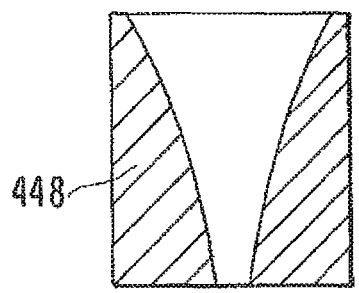
Figure 26C:
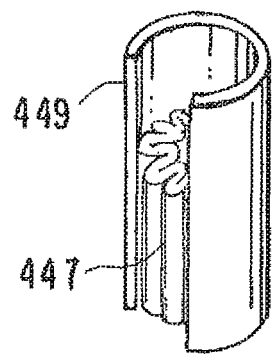

FIGS. 26a to 26c illustrate a tricuspid valve in accordance with yet another preferred embodiment of the present invention, provided with a self-expandable frame. FIG. 26a is an isometric view of an implantable prosthetic valve 430 mounted on a self-expandable frame 445. Implantable prosthetic valve 430 comprised of three valve leaflets is mounted on self-expandable frame 445 so that each leaflet extends along an equidistant portion of the frame and is sutured at both opposite sides to substantially equidistant and substantially parallel beams 440. By using a tapered tube 448 the whole assembly is crimped into a restriction tube 449. FIG. 26b shows the crimped valve assembly 447 in its final crimped diameter ready for insertion to the body. After insertion into the desired location in the body the valve is released from the restriction tube and as it is made of self expandable material (like a shape-memory alloy), it expands back to the original diameter and is anchored in place. In order to reduce the diameter of the device from its fully expanded diameter to its crimped diameter a special tapered tube is used, shown in FIG. 26c.

Figure 27:
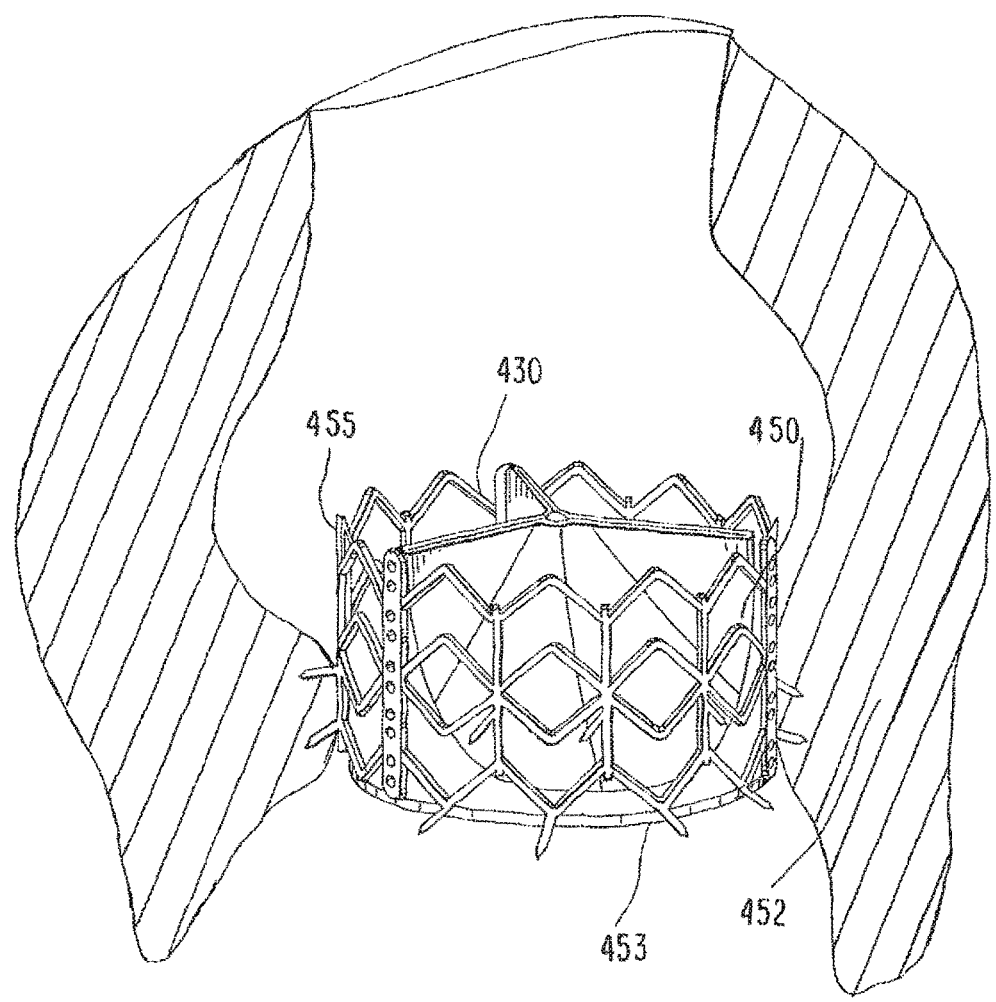
FIG. 27 illustrates an isometric view of an implantable prosthetic valve in accordance with another preferred embodiment of the present invention having hooks designated to anchor the valve assembly to body ducts.

FIG. 27 illustrates an isometric view of an implantable prosthetic valve in accordance with another preferred embodiment of the present invention having hooks designated to anchor the valve assembly to body ducts. An implantable prosthetic valve 450 is placed in a natural aortic valve position 452. Implantable prosthetic valve 450 comprises preferably three leaflets 430 mounted on a metallic support frame 455. The lower part of support frame 455 is provided with attachment means, preferably with hooks 453. Hooks 453 assures that the valve assembly stays in place after deployment, and cannot migrate to another position.

Figure 28:
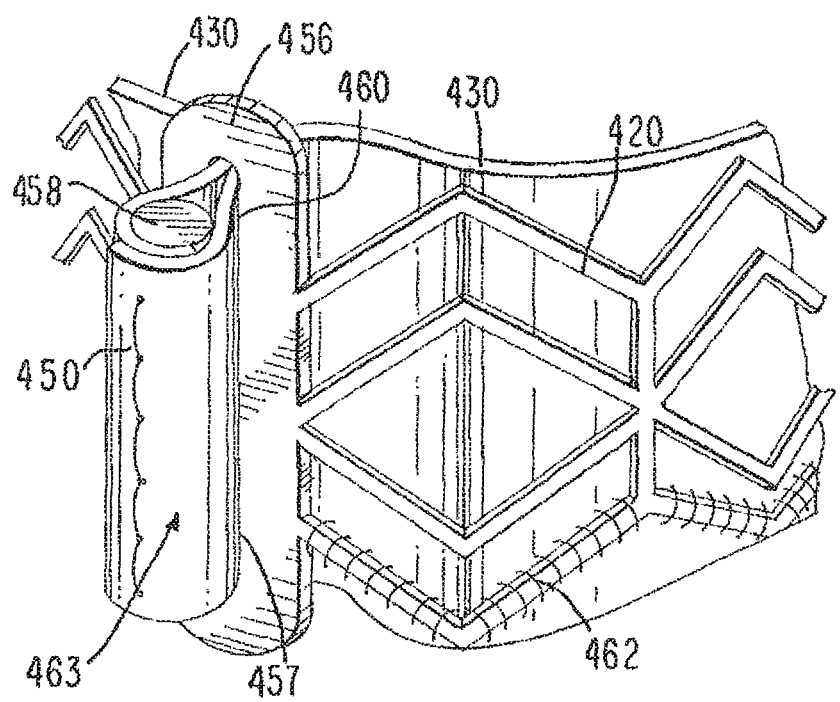
FIG. 28 illustrates a partial view of an implantable prosthetic valve in accordance with yet another preferred embodiment of the present invention. The commissural attachment is showed in details.

FIG. 28 illustrates a partial view of an implantable prosthetic valve in accordance with yet another preferred embodiment of the present invention. The commissural attachment is shown in details. This figure demonstrates an attachment technique that is used in order to attach pericardium leaflet 430 to a metallic frame 420. A longitudinal bar 456 having a narrow slit 457 is used as the commissural attachment so that extensions 463 of pericardium leaflet 430 are tightly inserted through slit 457. Pericardium extensions 463 that are extended beyond slit 457 are wrapped about a rigid bar 458 that acts as an anchoring means. Every two extensions originating from two sides of slit 457 are sutured to each other by a suture 459 at the side of rigid bar 458 opposite the slit. An additional suture 462 attaches the bottom circumference of support frame 420 to leaflet 420 in order to obtain sealing. The advantages of the described attachment are that no sutures or suture holes are applied in the leaflet working area, there are no concentrated stress points similar to stress point caused by suturing, and the force distribution is along the longitudinal bar 456. The narrow passage that is maintained through slit 457 forces the leaflets to be static in respect to the support so as to reduce abrasion.

The embodiments that will be shown herein after are optional configurations of attachment between the leaflets and the support frame.

Figure 29A:
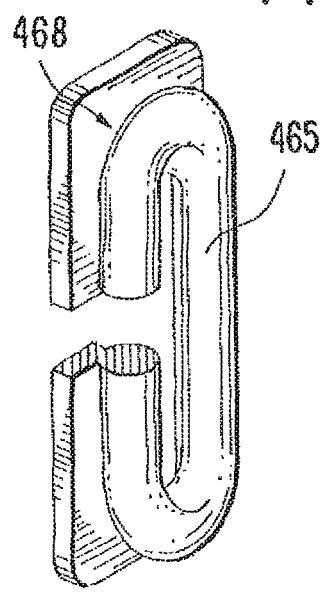
FIGS. 29a and 29b illustrate an isometric view and an upper cross-sectional view, respectively, of an attachment assembly of a valve's frame to leaflets in accordance with a preferred embodiment of the present invention.
Figure 29B:
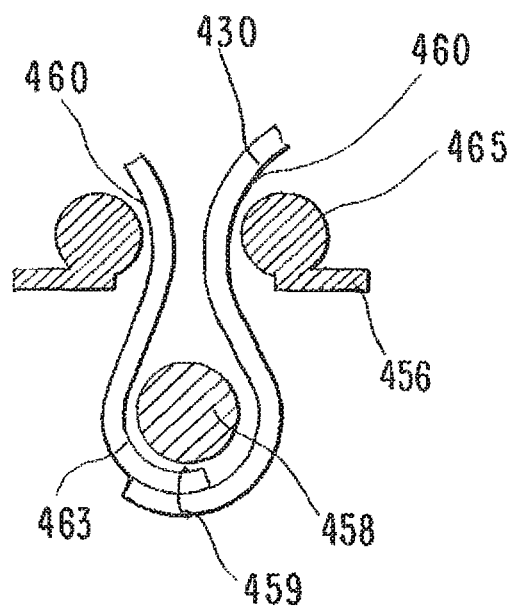

FIGS. 29a and 29b illustrate an isometric view and an upper cross sectional view, respectively, of an attachment assembly of a valve's frame to leaflets in accordance with a preferred embodiment of the present invention. The attachment is similar in principle to the attachment shown in FIG. 28, however, longitudinal bar 456 is further provided with an additional pole 465 that is attached to longitudinal bar 456 so as to establish an integral part. Pole 465 is rounded so as to make sure the leaflets will not be abraded or cut by sharp corners. In the cross sectional view shown in FIG. 29b, adjacent leaflets 460 can be seen compressed together and the main protection goal is clearly shown.

FIGS. 30a to 30c illustrate an isometric view, a cross-sectional view and a flatten view, respectively, of an attachment assembly of a valves frame to leaflets in accordance with another preferred embodiment of the present invention. Using the method demonstrated in FIGS. 30a to 30c, the pericardial leaflets are pre-cut to the desired shape 430 and are provided with longitudinal bars 470 that are sutured to the leaflets creating a longitudinal clamping effect (FIG. 30c). This allows distribution of forces along the whole length of the attachment means as opposed to concentrating the stresses in suture holes. In FIGS. 30a and 30b, an additional rigid portion 458 is added, creating a round ending, which prevents the leaflets from being bent drastically at the attachment point to portions of the frame 420. The attachment to frame 420 is performed using sutures 459.

Figure 31A:
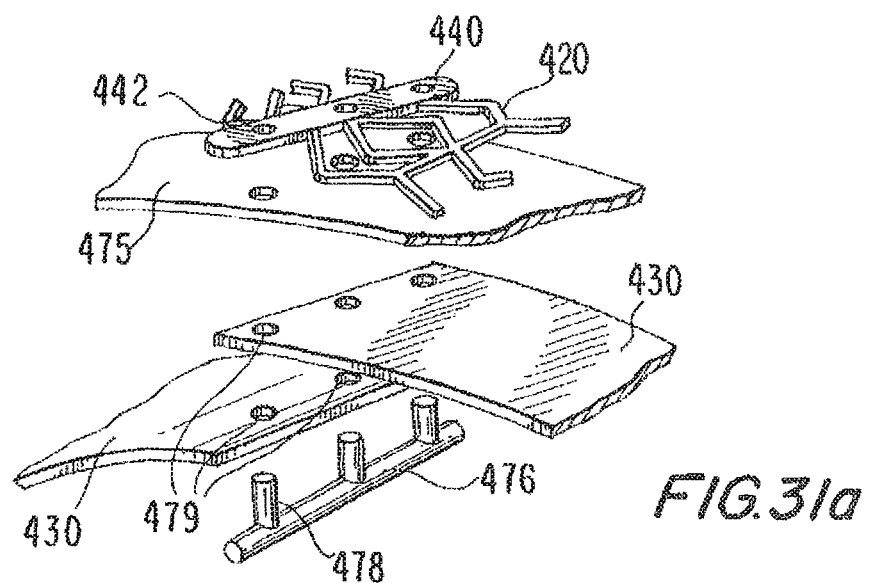
FIGS. 31a and 31b illustrate an exploded view and an isometric view, respectively, of a commissural attachment in accordance with a preferred embodiment of the present invention depicting the attachment technique.
Figure 31B:
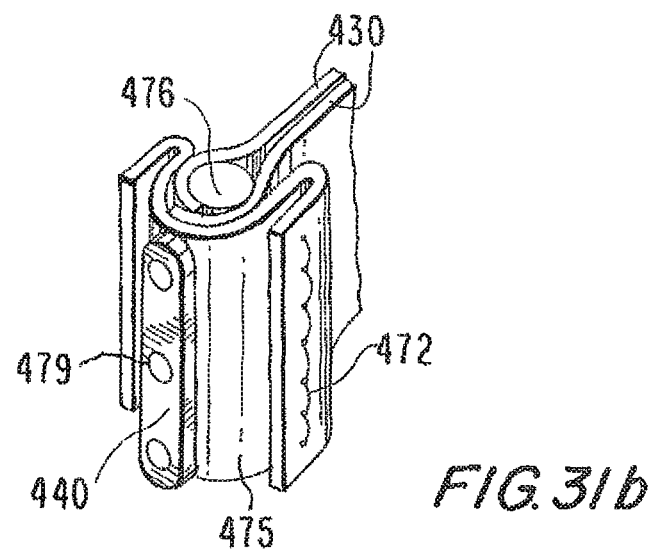

FIGS. 31a and 31b illustrate an exploded view and an isometric view, respectively, of a commissural attachment in accordance with a preferred embodiment of the present invention depicting the attachment technique. A method of assembling pericardial leaflets 430 to a frame 420 is demonstrated. A rigid bar 476 provided with integral protrusions 478 is inserted through bores 479 that are pre-cut in pericardial leaflets 430. Integral protrusions 478 pass through a sheet of preferably PET (braided polyester) fabric 475, and finally through bores 442 that are provided in longitudinal bar 440 (the attachment means) of frame 420. After the assembling of the parts, as shown in FIG. 31b, the parts are tightly assembled and bar protrusions 478 are attached to bar 440 by welding, riveting or any other technique. The PET sheet 475 is folded and sutured tightly around bar 476 using suture 472.

Figure 32A:
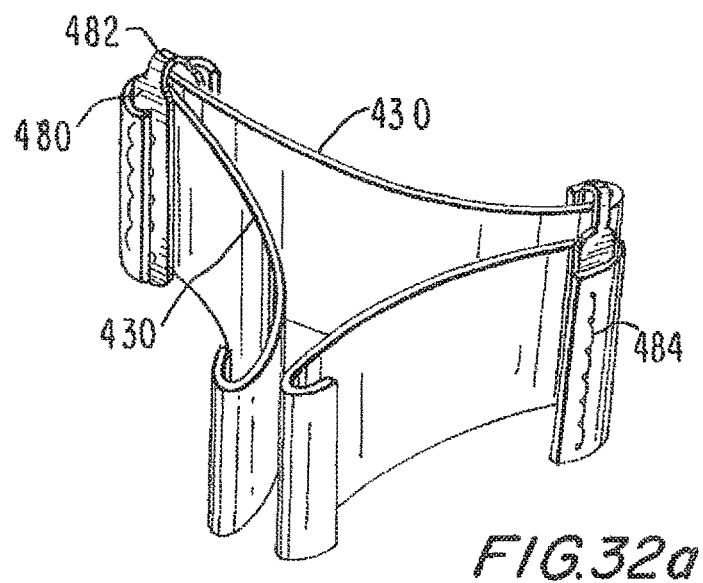
FIGS. 32a through 32c illustrate an isometric view of an attachment between leaflets and the frame in accordance with yet another preferred embodiment of the present invention.
Figure 32C:
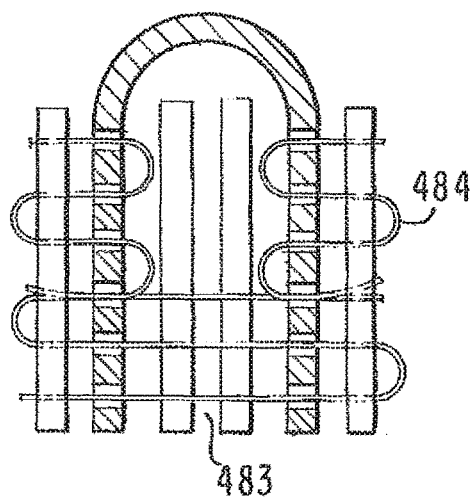
Figure 32B:
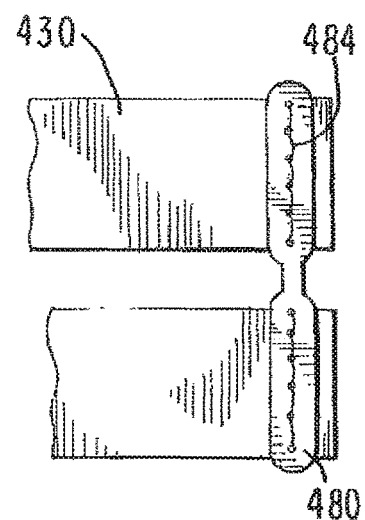

FIGS. 32a to 32c illustrate an isometric view of an attachment between leaflets and the frame in accordance with yet another preferred embodiment of the present invention. An optional method of attachment is demonstrated, in which a pericardium leaflet 430 and bars 480 are sutured in an area as far as possible from the working area of the leaflets. The pericardium is first sutured using a suture 484 to bar 480 as seen in FIG. 32b, and then folded and compressed. In order to firmly hold the pericardial leaflets in place between bars 480, an integral connecting member 482 connects the two bars, allowing the bent portions of the bars to be in parallel position, with the leaflets caught in between. Then, an additional suture 483 connects the bottom side of the bar to the leaflets so that while the valve is working, the leaflets do not bear high stresses.

Figure 33A:
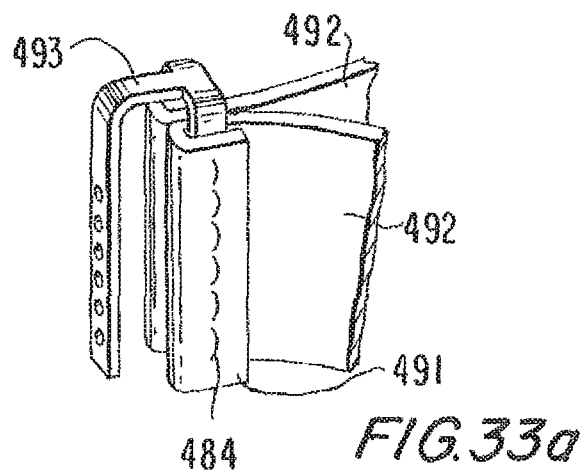
FIGS. 33a to 33d illustrate different views and portions of an attachment between a pericardium and a frame in accordance with yet another preferred embodiment of the present invention, demonstrating another method of attachment in accordance with the preferred embodiment.
Figure 33B:
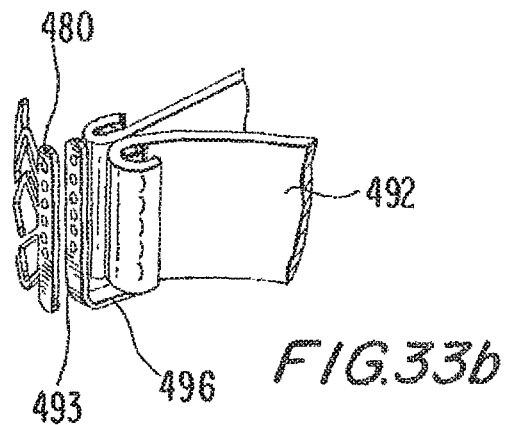
Figure 33C:
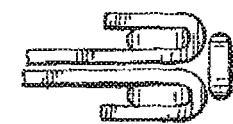
Figure 33D:
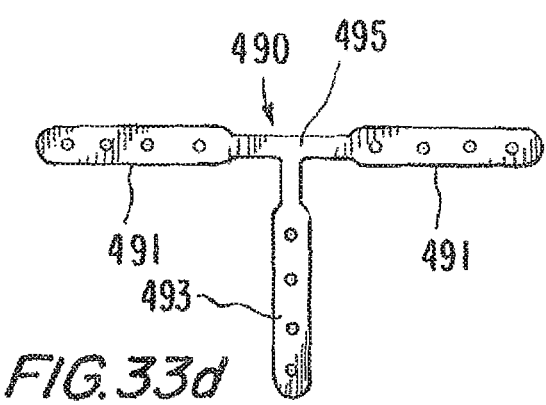

FIGS. 33a to 33d illustrate different views of portions of an attachment between a pericardium and a frame in accordance with yet another preferred embodiment of the present invention, demonstrating another method of attachment in accordance with the preferred embodiment. A connecting member 490 (shown in a deployed position in FIG. 33d) is used to connect two pericardial leaflets 492 at the line of the commissural. After being connected between them, pericardial leaflets 492 are being connected to frame bar 480. Here again, the principal of compressing the leaflets between two bent portions bars 491 of connecting member 490 and tightening them using suture 484 without punctures in the working areas of the pericardium is applied. However, connecting member 490 is provided with a portion 493 that is positioned perpendicular to the two bent portions bars 491 that holds the two leaflets together. Portion 493 is the connecting member to frame's bar 480. In FIG. 33a, the junction point 495 between the portions of connecting member 491 is placed at the upper part (outlet) of the frame so as to achieve a rigid connection to the frame. In FIG. 33b, junction point 495 is placed at the bottom part (inlet) of the frame so that the junction point also functions as a spring. Comprehensive explanation of the benefits of springs in commissures is discussed and shown in respect with FIGS. 37 to 39.

Figure 34A:
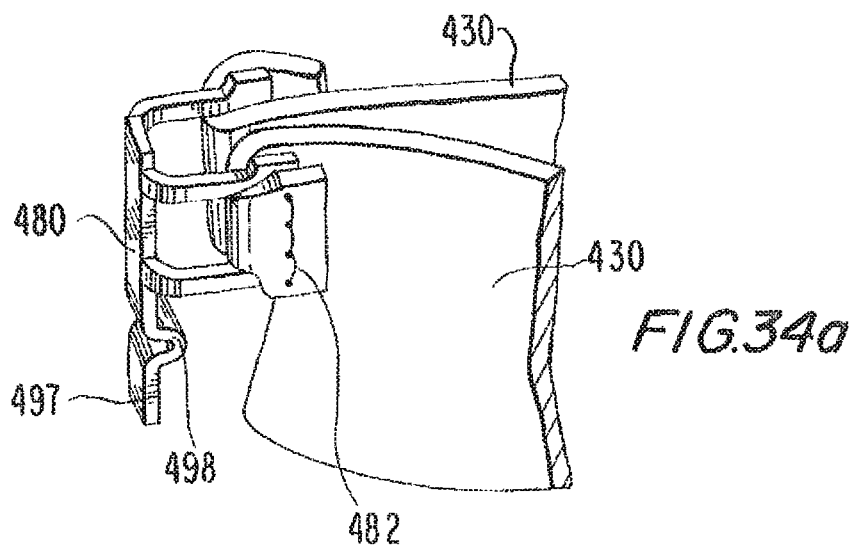
FIGS. 34a to 34c illustrate an isometric view of an attachment between a pericardium and a valve in accordance with yet another preferred embodiment of the present invention demonstrating another method of attachment.
Figure 34B:
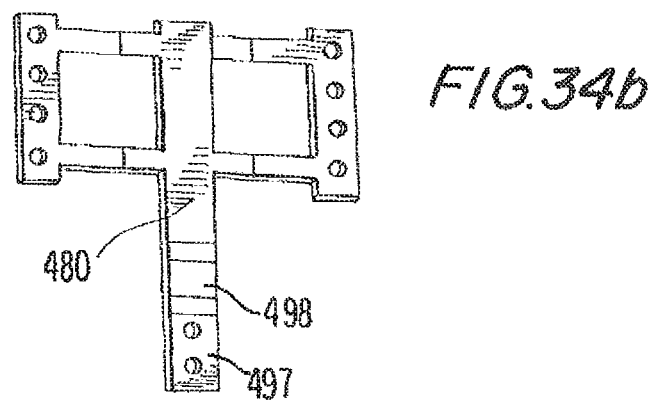
Figure 34C:
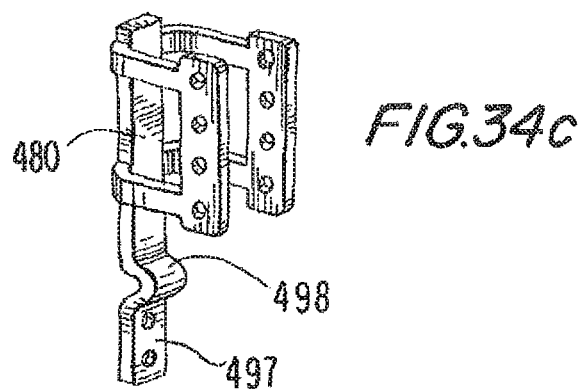

FIGS. 34a to 34c illustrate an isometric view of an attachment between a pericardium and a valve in accordance with yet another preferred embodiment of the present invention demonstrating another method of attachment. In FIGS. 34b and 34c, a deployed portion and the folded portion, respectively, are shown. An optional design for the attachment between the frame and the leaflets is depicted. A connecting member 480 (shown clearly in FIG. 34b) is being produced into a flat configuration using laser-cutting. Connecting member 480, which is a part of the frame's attachment means, is bent and then is ready for assembly with the leaflets. Connecting member 480 comprises the main body as well as a connection bar 497 and a flexible element 498 allowing flexibility to the commissural. Leaflets 430 are threaded through corresponding holes 481 in the structured connecting member 480 and are sutured using a suture 482.

Figure 35A:
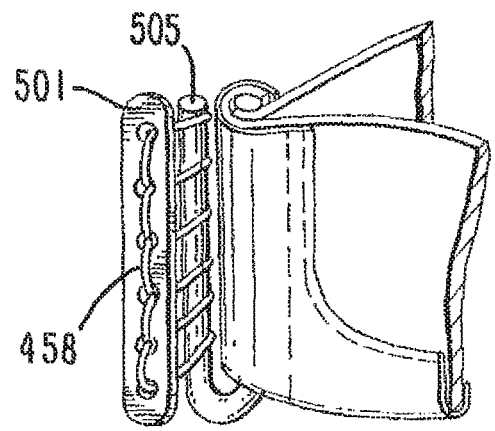
FIGS. 35a to 35c illustrate an isometric and cross-sectional upper views, respectively, of attachment techniques between a pericardium leaflet and a valve's frame in accordance with another preferred embodiment of the present invention.
Figure 35B:
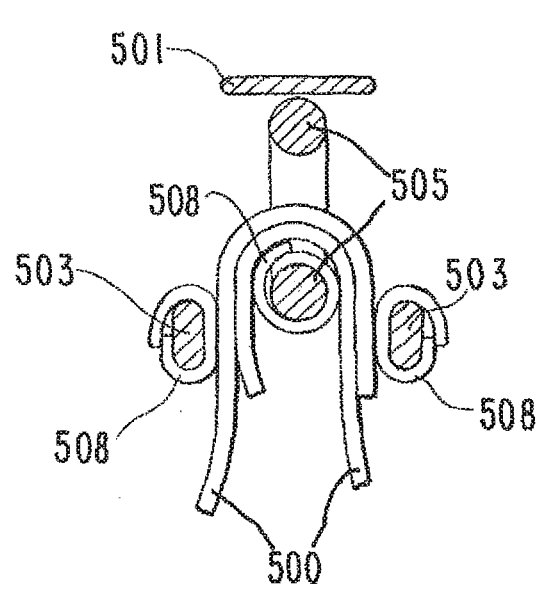
Figure 35C:
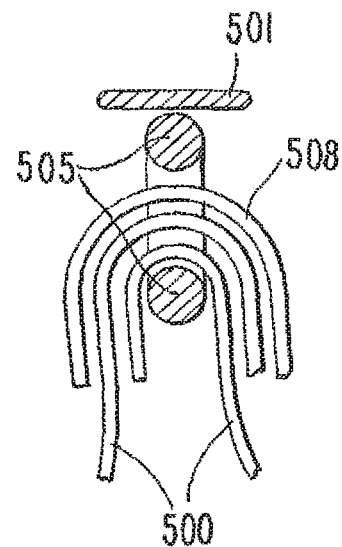

Reference is now made to FIGS. 35a, 35b, and 35c illustrating isometric and cross-sectional upper views, respectively, of attachment techniques between a pericardium leaflet and a valve's frame in accordance with other preferred embodiments of the present invention. FIGS. 35b and 35c depict different techniques of commissural attachments: in FIG. 35b two pieces of pericardial leaflets 500 are wrapped around a metallic member 505 that is connected to a frame 501. Rigid members 503 are positioned from both sides of metallic member 505 and then tightened together and connected by a suture 502. All metallic pieces are wrapped by PET fabric 508 in order to avoid direct contact between the metallic pieces and the delicate pericardial leaflets. The advantage of this structure is that after tightening the suture, the whole commissure becomes static with no relative movement between the portions. This improves the valve assembly's resistance to abrasion. In addition, there are no needle holes or sutures in the working area. FIG. 35c depicts a similar structure, however, there is no use of rigid sidebars. After wrapping the metallic member 505 with pericardial leaflets 500, a piece of PET 508 is used for tightening it to a tight bundle. In this case, the suture line 502 is the borderline of the working area so it should be designed so that stresses are in the best possible distribution.

Figure 36A:
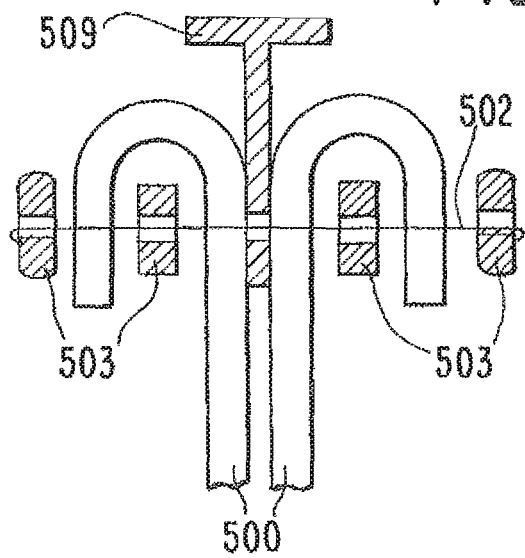
FIGS. 36a and 36b illustrate an isometric view of a commissural assembly in accordance with a preferred embodiment of the present invention demonstrating a method of forming one.
Figure 36B:
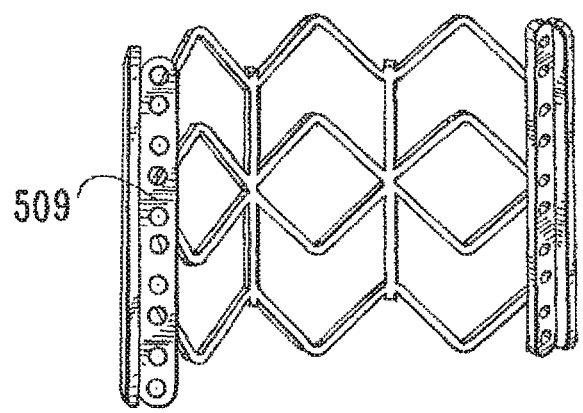

FIGS. 36a and 35b focus on the connection of the commissural assembly to frame's protrusion 509, which is an integral part of the frame and is the basis for the commissural attachment. This example shows the use of four rigid longitudinal bars 503 connected by a suture 502.

Figure 37A:
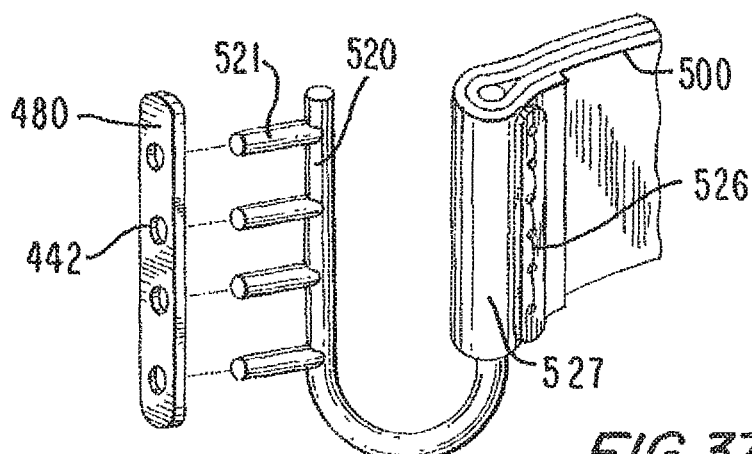
FIGS. 37a to 37c illustrates a commissural assembly in accordance with another preferred embodiment of the present invention, where the connecting bar functions as a flexible support and has integral attachment means to the frame.
Figure 37B:
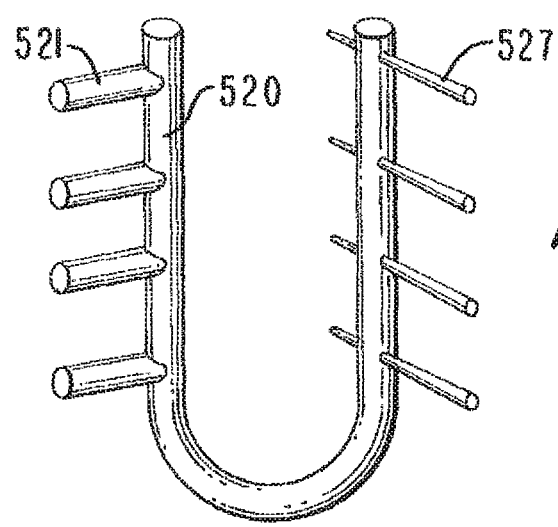
Figure 37C:
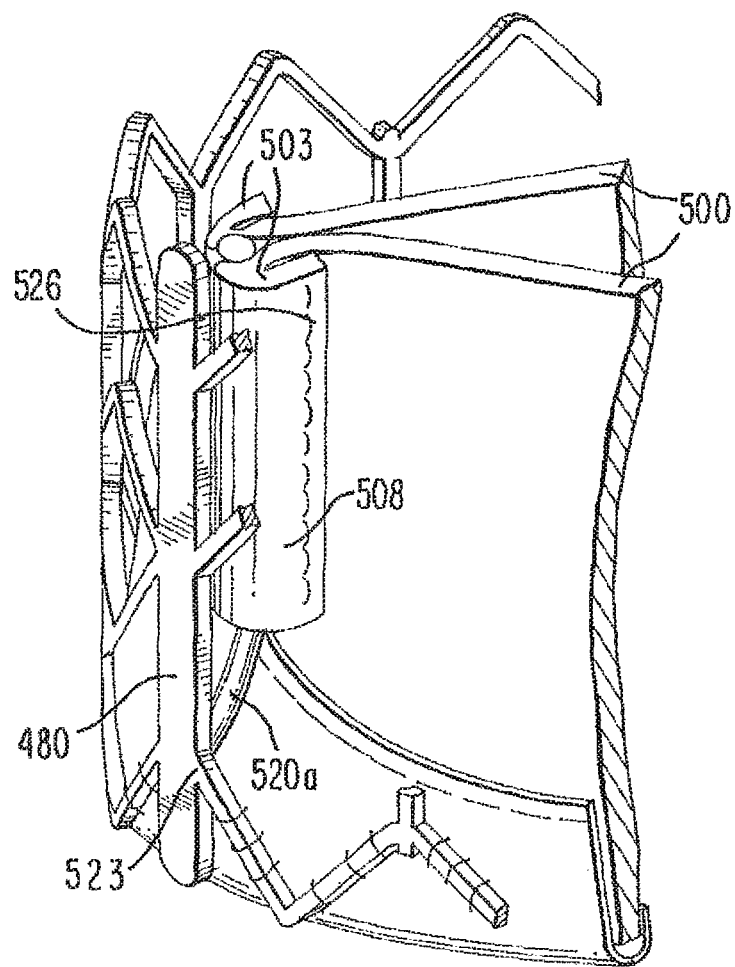

FIGS. 37a to 37c illustrate a commissural assembly in accordance with another preferred embodiment of the present invention, where the connecting bar functions as a flexible support and has integral attachment means to the frame. FIG. 37b is an isometric view of the connecting bar. Connecting bar 520 is flexible and comprises a resilient material shaped in a "U" shape. Connecting bar 520 is a part of commissural assembly 527 shown in FIG. 37a. Connecting bar 520 is provided with protruding elements 521 that are acting as the means of attachment to the frame's bar 480. Protruding elements are designated to be inserted in corresponding bores 442 in bar 480. It is optional to provide rods 527 which are integral parts of the "U" shaped member and replace the suture 526 that connects the pericardium leaflet and the connecting bar together, which is shown in FIG. 37a. FIG. 37c depicts another method of attaching the flexible connecting bar 520 to the frame 480 by means of welding 523. Here the pericardial leaflets 500 are attached to the connecting bar 520 by suture 526 inserted through a PET fabric 508 and two connecting bars 503, which together create a tight bundle.

Figure 38A:
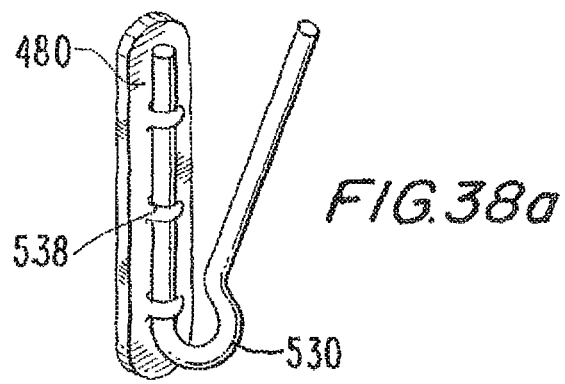
FIGS. 38a to 38g illustrate isometric views of flexible commissural supports and the method of attaching them to a pericardium and a frame and valve in accordance with preferred embodiments of the present invention.
Figure 38B:
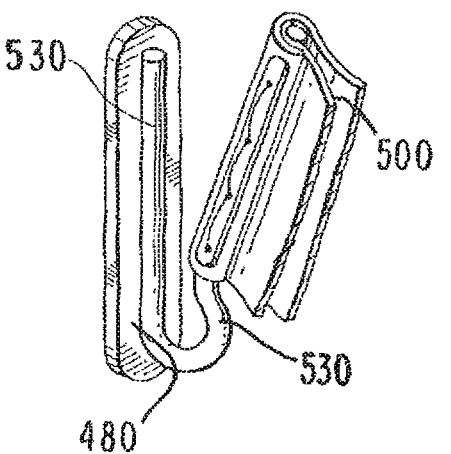
Figure 38C:
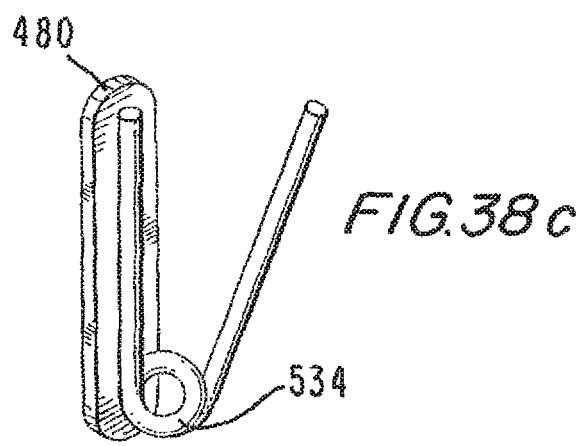

FIGS. 38a to 38g illustrate isometric views of flexible commissural supports and the method of attaching them to a pericardium and a frame a valve in accordance with preferred embodiments of the present invention. FIGS. 38a to 38c demonstrate incorporation of different design options of commissural springs. The main purpose of a commissural spring is to reduce the impact applied to the pericardial leaflets when the valve leaflets are closed. If the structure is of a rigid nature, high stress will be applied each time the valve closes. If a spring is added to the structure, the spring will bear the highest portion of the impact, thus reducing the stress applied to the leaflets during the time the valve is closed. In FIG. 38a, a simple stainless steel spring 530 is connected to frame's bar 480 by threading a portion of the spring into slots 538 as shown in more detail in FIGS. 38e and 38f. In FIG. 38b, there is a similar spring 530 with leaflets 500 connected to it by one of the attachment methods, the commissural support itself 530 is connected to the frame's bar 480 by spot welding, laser welding or other attachment means. FIG. 38c depicts a similar spring 534 having an additional spiral. The purpose of such a spiral is to reduce stress in the spring and to allow the fatigue requirements, which in the case of heart valves are of at least 200 million cycles.

Figure 38D:
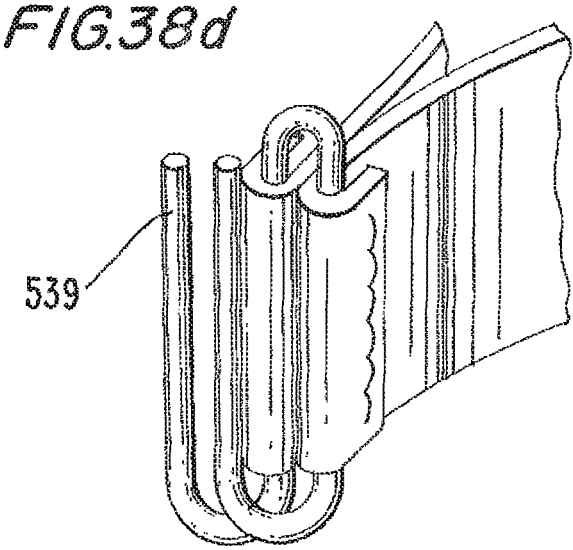
Figure 38E:
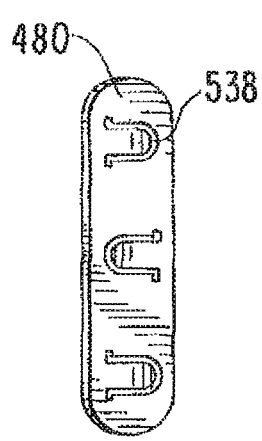
Figure 38F:
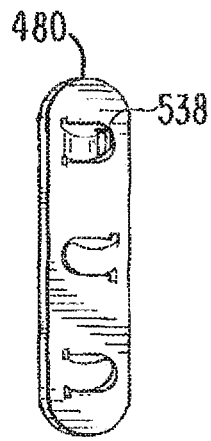
Figure 38G:
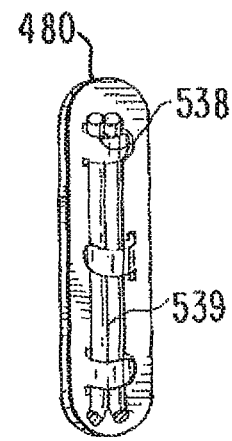

FIG. 38d illustrates an isometric view of a flexible commissural support in accordance with yet another preferred embodiment of the present invention, demonstrating the attachment of the pericardium to the support. FIGS. 38e to 38g are the details of the attachment to the frame. A commissural spring of a different design 539 comprises a stainless steel wire of a small diameter in respect with the springs described in FIGS. 38a to 38c. One advantage of this structure is the distribution of stresses in the spring and the ability to form a structure, which can be crimped to a small diameter. Another advantage in this structure is that there are no open edges of the spring, which can be dangerous when operated; the open edges are protected in the frame's bar as shown in FIGS. 38e to 38g, which show possible attachment methods of the spring to the frame. In FIG. 38e, a frame's flat bar 480 has slots 531 cut to form slot tabs 538 for crimping the spring 530. FIG. 38f shows pre-bending of the slots 527 and FIG. 38g shows the spring legs 539 assembled firmly into the slot tabs 538.

Figure 39A:
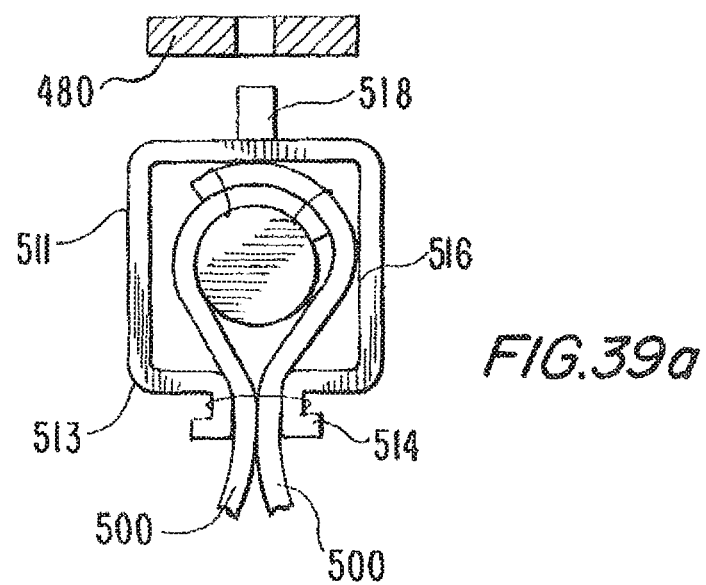
FIGS. 39a and 39b illustrate an isometric view of a commissural attachment in accordance with yet another preferred embodiment of the present invention, demonstrating the attachment of the pericardium to the support by means of a shaped compressing member.
Figure 39B:
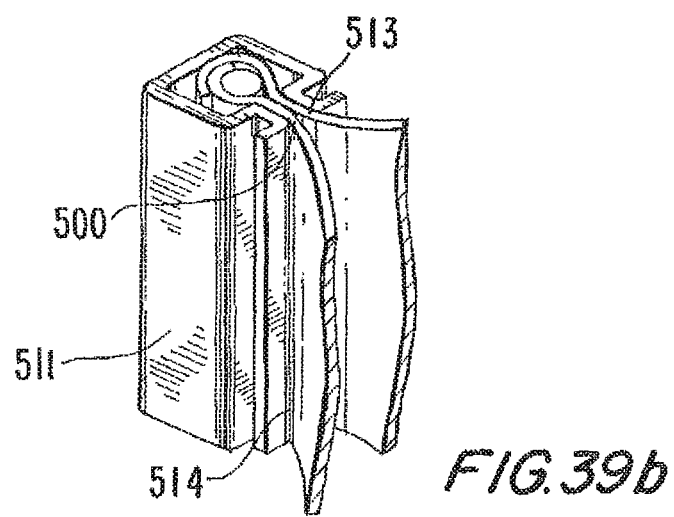

FIG. 39a illustrates a technique of commissural assembly using a shaped compressing member 511. The compression member 511 holds pericardial leaflets 500 firmly while pressing it in the pivot points 513. A radial edge 514 is made in order to protect the pericardium from abrasion. The whole assembly is held tightly inside the compressing member 516. The commissural assembly is connected to the frame by protrusion member 518, which fit bores in the frames bar 480. FIG. 39b is an isometric view of the same detail.

Figure 40A:
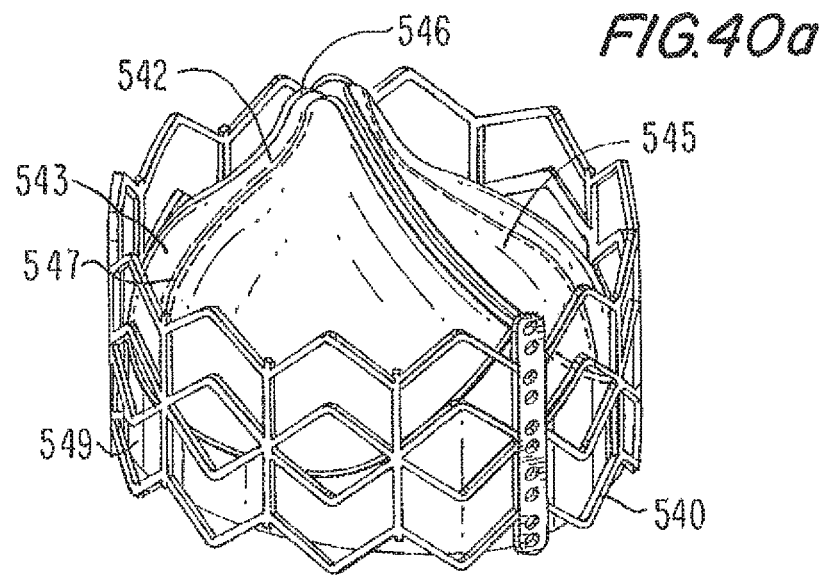
FIGS. 40a to 40c illustrate an isometric view of a bicuspid valve mounted on a frame in accordance with yet another preferred embodiment of the present invention.
Figure 40B:
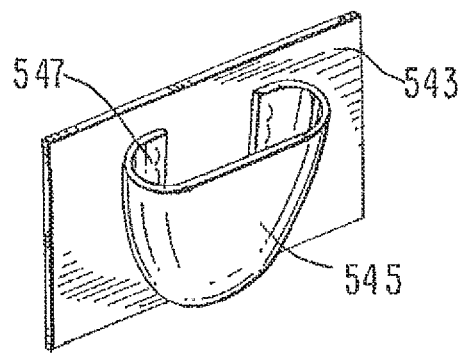
Figure 40C:
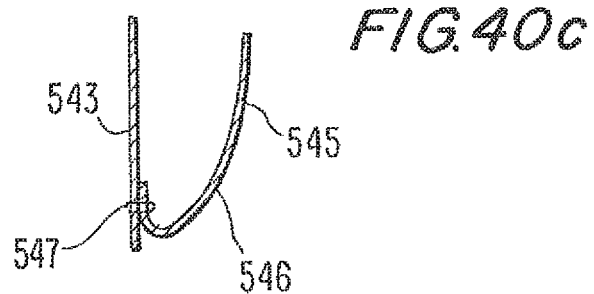

FIGS. 40a to 40c illustrate an isometric view of a bicuspid valve mounted on a frame in accordance with yet another preferred embodiment of the present invention. FIGS. 40b and 40c depict a cross-sectional side view and an isometric view, respectively, of the pericardium that is sutured to a PET tube in the form of pockets. The valve assembly (in this case bicuspid) comprises a crimpable frame 540, two pericardial leaflets 545, a PET skirt 543 and a connecting suture 547. The focus in this drawing is on the pocket shape of the pericardium leaflet shown best in FIGS. 40b and 40c. One of the main goals in valve design, in general, is to distribute the stresses in a homogenous way in the pericardium material and the attachment areas. The design of the pericardium leaflet as a pocket assists in distributing the stresses along suture line 547; pericardium leaflet 545 is sutured to PET skirt 543 along connecting suture 547. PET skirt 543 is sutured to the circumference of crimpable frame 540 at the bottom side 549 and at the top 542 using one of the commissural attachments that are described herein before regarding other embodiments. When hydrodynamic pressure is applied on leaflets 545, the leaflets will meet in the center 546 of frame 540 so as to seal the valve assembly. The shape of the leaflets in the valve assembly is determined by the boundary conditions, which in this case are the suture lines. The suture lines can be designed to have an optimal shape regarding the stress distribution in accordance with geometrical restrictions.

Figure 41A:
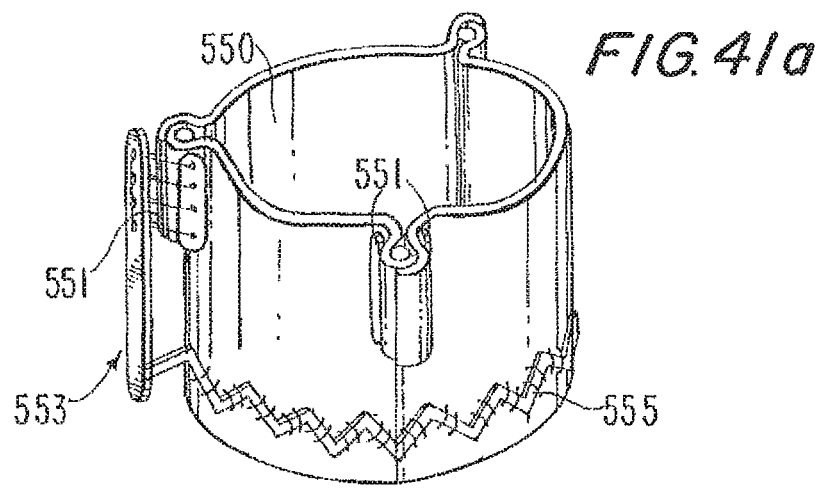
Figure 41B:
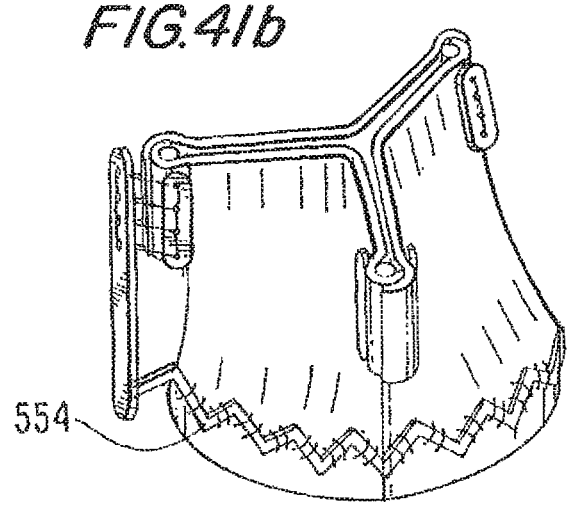
Figure 4L:
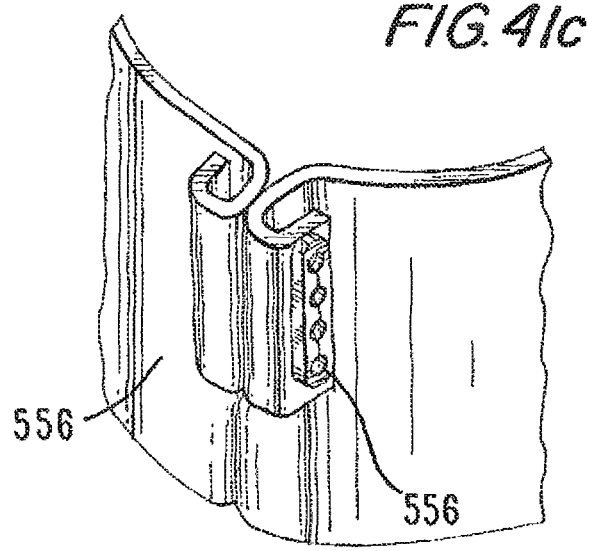
Figure 4L:
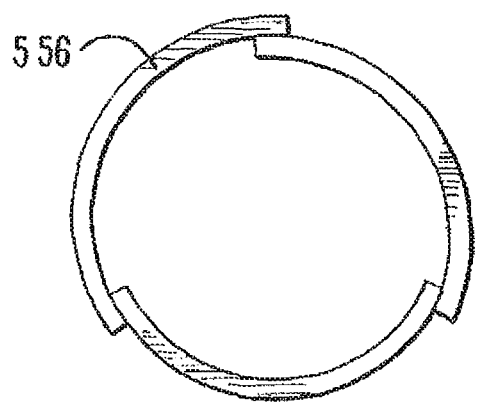

Reference is now made to FIGS. 41a to 41d illustrating isometric views of an implantable prosthesis tricuspid valve in accordance with yet another preferred embodiment of the present invention. FIG. 41a illustrates valve assembly 553 in an open state. Valve assembly 553 comprises a frame 555 (rigid or crimpable), pericardial leaflets 550 and bars 551. It is emphasized that in the shown embodiment, the goal is to distribute the stresses on the commissural arrangement in an optimal way. Pericardial leaflets 550 are attached to bars 551 that act as attachment means. The attachment means are positioned at the top third of the valve; the bottom circumference is attached to the frame in order to obtain full sealing. The middle part of the pericardium is left slack. The pre-cut pericardium is cut in greater dimensions than the frame; e.g., the height of the pericardium leaflet is greater than the height of the frame, for example, if the frame height is 15 mm, the pericardium will be cut to a height of 18 mm so as to establish a slack portion in the middle area of the valve assembly 553. FIG. 41b depicts the valve assembly in a closed state. The slack portion of the pericardium collapses toward the middle while creating a small pocket shape 554, which assists in the stress distribution. FIG. 41c shows the detailed commissural and the short bar attachment as well as the circumference sealing area at the bottom portion of the pericardium assembly. It is shown in the figures that bars 551, which are relatively short, allow firm attachment of the top portion of the commissural, slack portion in the middle, and a good sealing surface at the bottom portion 556.

Figure 42A:
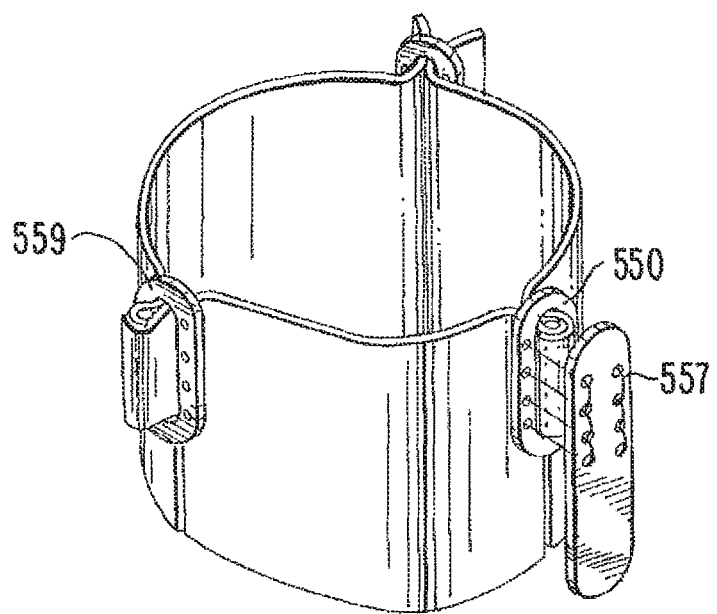
FIGS. 42a and 42b illustrate an isometric view of an implantable prosthetic valve in accordance with yet another preferred embodiment of the present invention, having a different commissural attachment.
Figure 42B:
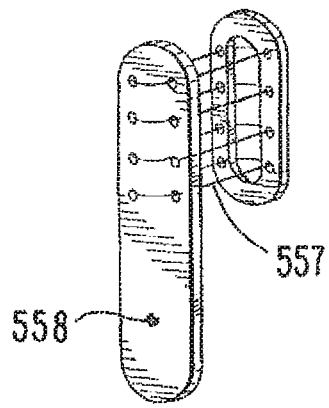

Reference is now made to FIGS. 42a and 42b illustrating an isometric view of an implantable prosthetic valve in accordance with yet another preferred embodiment of the present invention, having a different commissural attachment. FIG. 42b depicts the attachment in details. In the embodiment shown in FIG. 42a, similar valve assembly is illustrated, while the short bar is arranged in a manner that is similar to the structure shown in FIG. 28 and described herein before. Relatively short bars 559 act as the attachment means to the frame bar 558. Suture 557 attaches short bars 559 to a member 558, the suture can be made from an elastic material so that to add flexibility to the commissures and to render the valve assembly the benefits already explained herein.

Figure 43A:
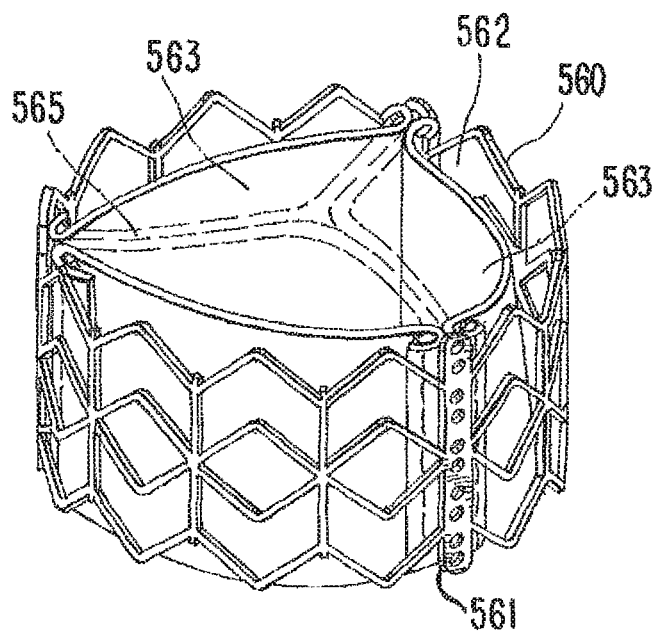
FIGS. 43a and 43b illustrate an isometric view of an implantable prosthetic valve in accordance with yet another preferred embodiment of the present invention.
Figure 43B:
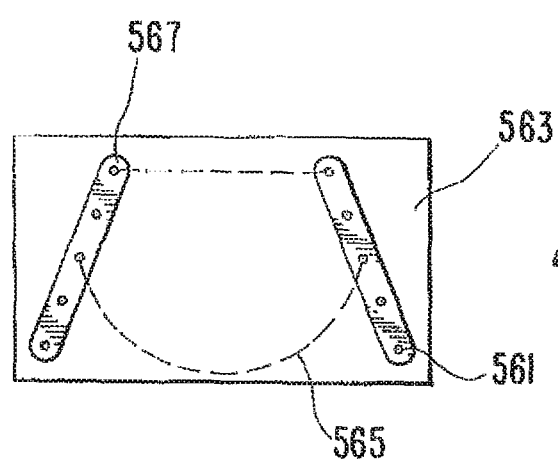

Reference is now made to FIGS. 43a and 43b illustrating an isometric view of an implantable prosthetic valve in accordance with yet another preferred embodiment of the present invention. FIG. 43a depicts commissures that are pre-sutured in a tapered shape. The valve assembly shown in FIG. 43a comprises a frame 560, pericardial leaflets 563, and attachment means 561. Pericardial leaflets 563 are shown to be in an open state so as to establish an open valve assembly while dashed lines 565 show the valve in a closed sealed state. The attachment to the commissures can be performed using one of the explained techniques. Specifically to the embodiment shown in FIGS. 43a and 43b, the focus is on the formation of a tapered valve in which the attachment means is in the shape of long bars 561 that are attached to the pericardium in an angular way in apposition to the parallel attachment. Attaching the bars in an angular way when the pericardium is flattened will create a tapered tube when built up to the three dimensional shape. When the whole prosthetic valve is inflated by a balloon, the pericardium leaflet, at the top circumference of the frame, is stretched and the frame is expanded to the full diameter. After deflating the balloon, the frame stays in its expended size but the pericardial leaflets regains their pre-stretched shape. This process creates a permanent clearance distance 562 between the pericardial leaflets 563 and frame 560. This is of major importance in the protection of the pericardium from abrading against the frame.

Figure 44A:
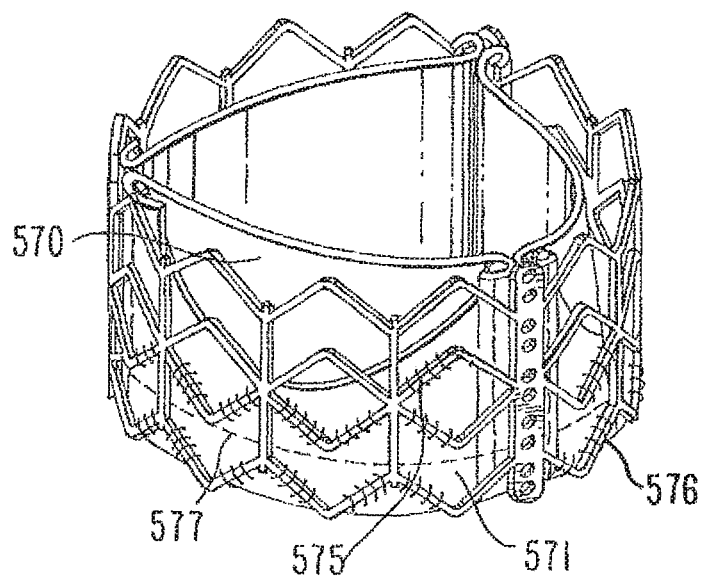
FIGS. 44a to 44c illustrate an isometric view of an implantable prosthetic valve in accordance with yet another preferred embodiment of the present invention, with additional pieces of PET used for sealing and protecting the pericardium.
Figure 44B:
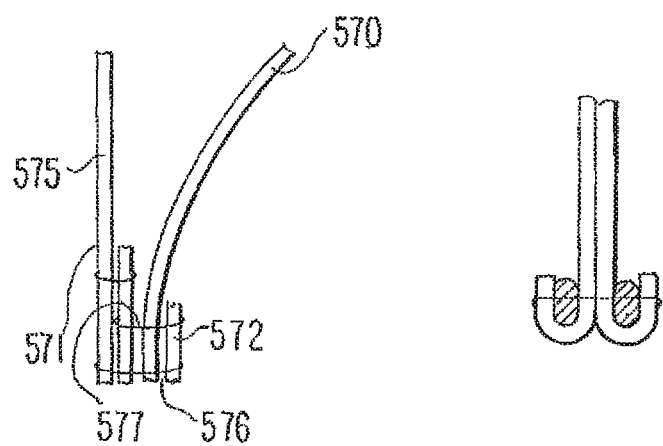
Figure 44C:
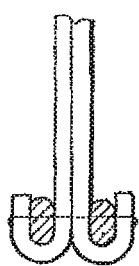

Reference is now made to FIGS. 44a to 44c illustrating an isometric view of an implantable prosthetic valve in accordance with yet another preferred embodiment of the present invention, with additional pieces of PET used for sealing and protecting the pericardium. The illustrated implantable valve assembly resembles the valve shown in FIG. 43, however, it is emphasized that in the attachment of the pericardial leaflets 570 to frame 575, there is use of PET. FIG. 44c shows in a cross-sectional view, the way the PET is assembled to the pericardium and the frame in a manner that protects the pericardium against wear. PET 571 and 572 are used for connecting pericardial leaflets 570 to frame 575, while they are assembled in between the leaflets and the frame. A suture 577 connects pericardium leaflet 570 in between two layers of PET, while the inner layer of PET 572 is short and the outer layer is longer. Bottom attachment suture 576, connects the three layers, the leaflet and both PET layers to the frame and forms a strong sealing line. An upper suture 578 connects the outer PET layer 571 to frame 575. When the valve assembly closes and the pericardial leaflets come closer to each other at the top of the assembly, there is a tendency of the bottom attachment to move and rotate about an attachment point 577. Upper suture line 578 keeps the outer PET layer tight and prevents a part of this rotational movement, which can rapidly cause an abrasion failure.

FIGS. 45a to 45d illustrate an isometric view of an implantable prosthetic valve in accordance with yet another preferred embodiment of the present invention, having leaflets sutured to a pre-shaped PET tube and optional leaflet-tube attachments in details. A novel technique of mounting pericardial leaflets 580 to a pre shaped PET tube 585 is shown. The tube is shaped so as to have a folding 586 with substantially sinusoid pattern 586 that is similar to the optimal connection line of valve leaflets in the natural valve. This shape allows the pericardial leaflets to be sutured to the interior of the PET tube. The preferred suturing techniques are shown in the cross sectional views of PET tubes in FIGS. 45b, 45c, and 45d. Generally, in order to protect the pericardial leaflets from tearing, an additional piece 583 of PET is added below the suture lines. Similar variations are shown in FIGS. 45c and 45d.

Figure 46A:
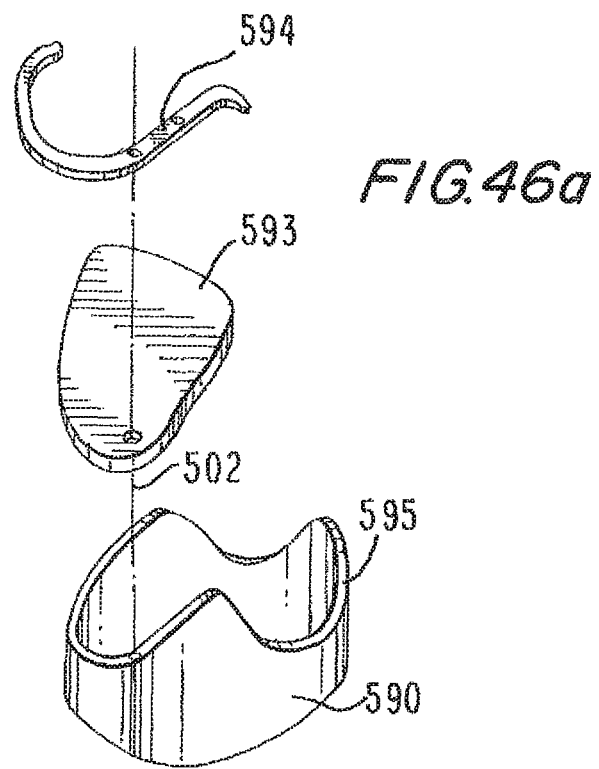
FIGS. 46a and 46b illustrate an exploded view and an upper cross-sectional view of an implantable prosthetic valve assembly in accordance with yet another preferred embodiment of the present invention.
Figure 46B:
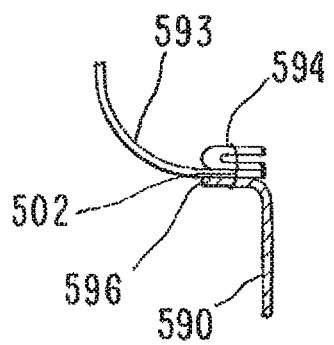
Figure 47A:
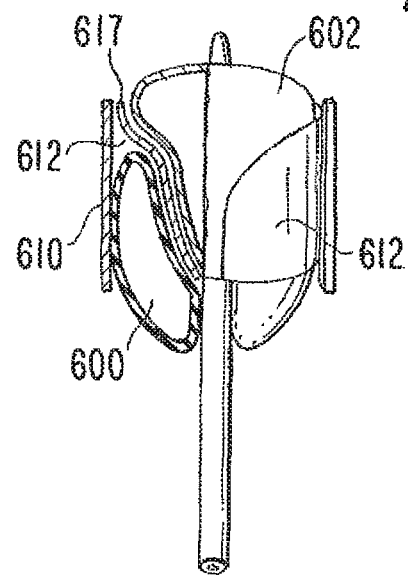
FIGS. 47a to 47c illustrate a partial cross-sectional side view of an inflating balloon in accordance with a preferred embodiment of the present invention. The balloon is a part of an implantable prosthetic valve delivery system.
Figure 47B:
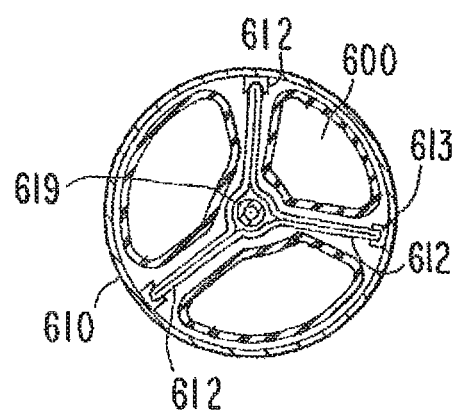
Figure 47C:
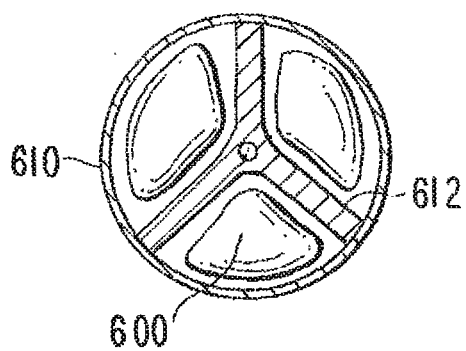

Reference is now made to FIG. 46a illustrating an exploded view of an implantable prosthetic valve assembly in accordance with yet another preferred embodiment of the present invention, where the leaflets are mounted on a pre-cut and pre-shaped tube and the outlet of the valve is cut in a commissural shape. FIG. 46a is view of the attachment. A pre-shaped PET tube 590 is cut to have substantially sinusoidal shape 596 and then bent in order to provide a suturing area. The pericardium leaflet 593 is pre-cut and assembled to PET tube 590 by means of suturing 502. In this case as well as in the former case, an additional protective layer of PET or pericardium 594 is added. FIG. 46b is a cross-section of the attachment detail after being tightened FIGS. 47a to 47c illustrate a partial cross-sectional side view of an inflating balloon in accordance with a preferred embodiment of the present invention. The balloon is a part of an implantable prosthetic valve delivery system. FIGS. 47b and 47c are cross sectional upper views in the inflated and deflated positions, respectively. The specially designed balloon shown in the figures preferably comprises four inflating members, three substantially identical and symmetrical sections 600 and a central section 602. Pericardial leaflets 612 are positioned between sections 600 and separate them. A frame 610 circles the inflating members and a balloon shaft 619 that is positioned in the center of the delivery system while a commissural connection 613 connects pericardial leaflets 612 to frame 610. The inflated balloon sections 600 are placed between frame 610 and pericardial leaflets 612 so that when the inflating members are inflated, they push leaflets 612 toward each other and frame 610 so as to establish a fully closed position. This technique better preserves the leaflets since there is no contact between the leaflets and the frame besides in the commissural connection. The preservation of the leaflets is even improved in times of inflation as well as after inflating the valve and establishing a closed position. In FIG. 47a the fourth inflating member of the balloon, central section 602 is clearly shown. Through central section 602, the inlet 617 of the valve is inflated while the inflated central section assures that the whole valve is fully inflated to substantially round shape. FIG. 47c shows the assembly in a crimped position. Frame 610 is crimped and sections 600 are deflated. Pericardial leaflets 612 are also shown in a crimped configuration.

Figure 48A:
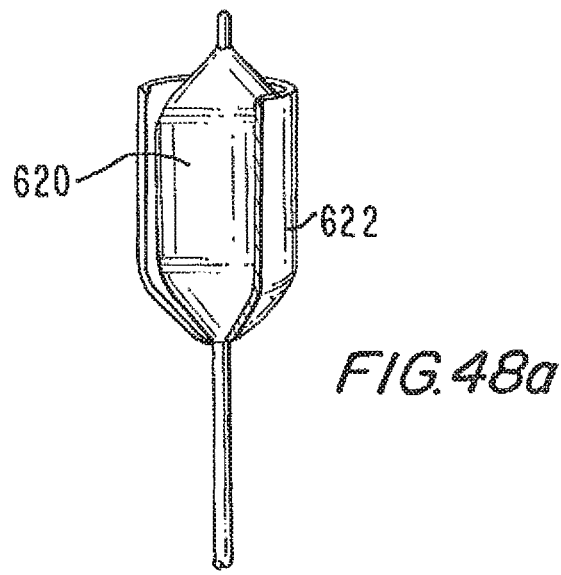
FIGS. 48a and 48b illustrate a partial cross-sectional side view and an upper cross-sectional view of an inflating balloon in accordance with another preferred embodiment of the present invention.
Figure 48B:
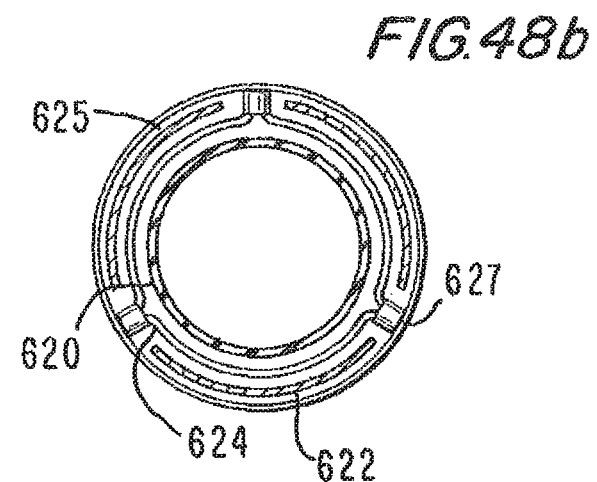

FIGS. 48a and 48b illustrate a partial cross-sectional side view and an upper cross sectional view of an inflating balloon in accordance with another preferred embodiment of the present invention. The inflating balloon comprises of a central inflating balloon 620 and three protection sheets 622. In the lateral cross-section shown in FIG. 48b, the parts of inflated assembly 625 are clearly shown, protection sheets 622 protects the pericardial leaflets 624 from being pushed against the frame 625 when the device is inflated. The advantage of this arrangement is in the protection of the pericardial leaflets.

The preferred embodiments representing an implantable prosthetic valve in accordance with the present invention are relatively easy to manufacture as they are generally flat throughout most of the production process and only at the final stage of mounting the other elements of the valve assembly on the support frame, a three dimensional form is established.

A typical size of an aortic prosthetic valve is from about 19 to about 25 mm in diameter. A maximal size of a catheter inserted into the femoral artery should be no more than 8 mm in diameter. The present invention introduces a device, which has the ability to change its diameter from about 4 mm to about 25 mm. Artificial valves are not new; however, artificial valves in accordance with the present invention posses the ability to change shape and size for the purpose of delivery and as such are novel. These newly designed valves require new manufacturing methods and technical inventions and improvements, some of which were described herein.

As mentioned earlier, the material of which the valve is made from can be either biological or artificial. In any case new technologies are needed to create such a valve.

To attach the valve to the body, the blood vessels determine the size during delivery, and the requirements for it to work efficiently, there is a need to mount it on a collapsible construction which can be crimped to a small size, be expanded to a larger size, and be strong enough to act as a support for the valve function. This construction, which is in somewhat similar to a large "stent", can be made of different materials such as Nitinol, biocompatible stainless steel, polymeric material or a combination of all. Special requirement for the stent are a subject of some of the embodiments discussed herein.

The mounting of the valve onto a collapsible stent is a new field of problems. New solutions to this problem are described herein.

Another major aspect of the design of the valve of the present invention is the attachment to the body.

In the traditional procedure the valve is sutured in place by a complicated suturing procedure. In the case of the percutaneous procedure there is no direct access to the implantation site therefore different attachment techniques are needed.

Another new problem that is dealt herein is the delivery procedure, which is new and unique. Positioning of the device in the body in an accurate location and orientation requires special marking and measuring methods of the device and surgical site as was disclosed herein.

Artificial polymer valves require special treatment and special conditions when kept on a shelf, as well as a special sterilization procedure. One of the consequences of the shelf treatment is the need to crimp the valve during the implantation procedure. A series of devices and inventions to allow the crimping procedure are disclosed herein.

It should be clear that the description of the embodiments and attached Figures set forth in this specification serves only for a better understanding of the invention, without limiting its scope as covered by the following claims.

It should also be clear that a person skilled in the art, after reading the present specification could make adjustments or amendments to the attached Figures and above described embodiments that would still be covered by the following claims.

What is claimed is:

1. A method of deploying a prosthetic heart valve at the natural aortic valve position in a patient, comprising:
   advancing a guide wire into a femoral artery;
   advancing a catheter over the guide wire, the catheter having a prosthetic heart valve disposed along a distal end portion thereof, the prosthetic heart valve comprising a radially collapsible and expandable annular support frame and three pairs of parallel support bars mounted radially inwardly of the support frame, each support bar provided with a plurality of preformed bores, the prosthetic heart valve further comprising a valve assembly anchored within the support frame at least in part by stitching that extends through the bores of the support bars and portions of the valve assembly;
   radially expanding the prosthetic heart valve at the natural aortic valve position; and
   withdrawing the catheter over the guide wire and removing the catheter and guide wire from the patient.

2. The method of claim 1, wherein the valve assembly comprises three pericardial leaflets.

3. The method of claim 2, wherein a gap is provided between each pair of parallel support bars through which a respective pair of adjacent end portions of the pericardial leaflets extend.

4. The method of claim 1, wherein a balloon is inflated for radially expanding the prosthetic heart valve.

5. The method of claim 1, wherein the annular support frame is made from a shape memory alloy.

6. The method of claim 5, wherein the shape memory alloy is nickel titanium.

7. The method of claim 1, wherein an inlet of the valve assembly is sutured to an inlet end of support frame.

8. The method of claim 1, wherein the support bars are not co-extensive with a height of the support frame.

9. The method of claim 8, wherein the support bars extend only along an outlet end portion of the support frame.

10. The method of claim 2, wherein each end portion of each pericardial leaflet wraps at least partially around one of the support bars.

11. A method for deploying a prosthetic heart valve at the natural aortic valve position at the entrance to the left ventricle of a myocardium of a patient, comprising:
    radially collapsing an implantable prosthetic heart valve having a collapsible and expandable support frame and a plurality of longitudinal support bars coupled to the support frame, the prosthetic heart valve also having a collapsible and expandable valve assembly, wherein each support bar includes a plurality of preformed bores formed therein for allowing the valve assembly to be sutured to the support bars, wherein the plurality of support bars are arranged in three pairs of parallel support bars, wherein the valve assembly comprises three valve leaflets, each leaflet having opposing end portions, each end portion being paired with an adjacent end portion of an adjacent leaflet to form a commissure of the leaflet assembly, each commissure extending through a respective pair of parallel support bars, wherein at each pair of parallel support bars, the end portion of one leaflet is folded partially around and stitched to one of the support bars of the respective pair of parallel support bars and the end portion of the adjacent leaflet is folded partially around and stitched to the other support bar of the respective pair of parallel support bars;
    advancing the prosthetic heart valve through the patient's vasculature towards the natural aortic valve position via a catheterization technique;
    positioning the prosthetic heart valve such that the support frame is located substantially within an annulus of a natural aortic valve; and
    radially expanding the prosthetic heart valve such that the support frame engages leaflets of the natural aortic valve;
    wherein, after implantation, the valve assembly allows blood to flow in a first direction and prevents blood from flowing in a second direction.

12. The method of claim 11, wherein the support frame is made from a shape memory, nickel titanium alloy.

13. The method of claim 11, wherein the pairs of parallel support bars are positioned along a top portion of the valve assembly.

14. The prosthetic heart valve assembly of claim 13, wherein a bottom portion of the valve assembly is stitched to an inlet end portion of the support frame along a circumference of the support frame inlet end portion.

15. The prosthetic heart valve assembly of claim 14, wherein the valve assembly comprises a middle slack portion between the top portion and the bottom portion, wherein the middle slack portion can collapse away from the support frame toward a center of the prosthetic heart valve assembly.

* * * * *